(12) United States Patent
Angehrn et al.

(10) Patent No.: US 6,294,668 B1
(45) Date of Patent: *Sep. 25, 2001

(54) VINYLPYRROLIDINONE CEPHALOSPORIN DERIVATIVES

(75) Inventors: Peter Angehrn, Böckten (CH); Ingrid Heinze-Krauss, Schliengen; Hans G. F. Richter, Grenzach-Wyhlen, both of (DE)

(73) Assignee: Hoffman-La Roche Inc., Nutley, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/964,640

(22) Filed: Nov. 5, 1997

(30) Foreign Application Priority Data

Nov. 6, 1996 (EP) .................................. 96117710
Sep. 15, 1997 (EP) .................................. 97115996

(51) Int. Cl.[7] .................. C07D 501/24; A61P 31/04; A61K 31/546

(52) U.S. Cl. .................. 540/222; 540/224; 540/225; 540/226; 540/227

(58) Field of Search .................. 540/224, 225, 540/226, 227, 222

(56) References Cited

U.S. PATENT DOCUMENTS

| 4,255,423 | 3/1981 | Beattie et al. | 544/16 |
|---|---|---|---|
| 4,307,233 | 12/1981 | Farge et al. | 544/16 |
| 5,275,816 | 1/1994 | Branch et al. | 514/221 |
| 5,504,076 | 4/1996 | Branch et al. | 514/206 |
| 5,523,400 | 6/1996 | Wei et al. | 514/202 |

FOREIGN PATENT DOCUMENTS

| 0 408 034 | 1/1991 | (EP) . |
|---|---|---|
| 0 620 225 | 10/1994 | (EP) . |
| 0 699 681 | 3/1996 | (EP) . |

(List continued on next page.)

OTHER PUBLICATIONS

1 VPAC Namng Rules, 1965, Rule c81.1, pp. 60,65,142,143.

(List continued on next page.)

*Primary Examiner*—Mark L. Berch
(74) *Attorney, Agent, or Firm*—George W. Johnston; Patricia S. Rocha-Tramaloni; Eileen M. Ebel

(57) ABSTRACT

The present invention relates to cephalosporin derivatives of the general formula

I where
 $R^1$ is halogen, lower alkyl, phenyl, benzyl, styryl, naphthyl or heterocyclyl; the lower alkyl, phenyl, benzyl, styryl, naphthyl and heterocyclyl being optionally substituted by at least one of halogen, hydroxy, optionally substituted lower alkyl, optionally substituted lower alkoxy, optionally substituted phenyl, amino, lower alkylamino, di-lower alkylamino, carboxy, lower alkylcarboxy, carbamoyl or lower alkylcarbamoyl;
 $R^4, R^5$ independently are hydrogen, lower alkyl or phenyl;
 X is S, O, NH or $CH_2$;
 n is 0,1 or 2;
 m is 0 or 1;
 s is 0 or 1;
 $R^2$ is hydrogen, hydroxy, $-CH_2-CONHR^6$, lower alkyl-$Q_r$, cycloalkyl-$Q_r$, lower alkoxy, lower alkenyl, cycloalkenyl-$Q_r$, lower alkynyl, aralkyl-$Q_r$, aryl-$Q_r$, aryloxy, aralkoxy, a heterocyclic ring or a heterocyclyl-$Q_r$, the lower alkyl, cycloalkyl, lower alkoxy, lower alkenyl, cycloalkenyl, lower alkynyl, aralkyl, aryl, aryloxy, aralkoxy and the heterocyclic ring may be substituted with at least one group selected from carboxy, amino, nitro, cyano, $-SO_2NHR^6$, optionally fluoro substituted lower alkyl, lower alkoxy, hydroxy, halogen, $-CONR^6R^7$, $-CH_2CONR^6R^7$, $-N(R^7)COOR^8$, $R^7CO-$, $R^7OCO-$, $R^7COO-$, $-C(R^7R^9)CO_2R^8$, $-C(R^7R^9)CONR^7R^{10}$, wherein
 $R^6$ is hydrogen, lower alkyl, cycloalkyl or aryl;
 $R^7$ and $R^9$ are independently hydrogen or lower alkyl;
 $R^8$ is hydrogen, lower alkyl, lower alkenyl or a carboxylic acid protecting group; and
 $R^{10}$ is hydrogen, ωhydroxy-alkyl, phenyl, naphthyl or heterocyclyl, the phenyl, naphthyl or heterocyclyl being unsubstituted or substituted with at least one of the groups of optionally protected hydroxy, halogen, optionally substituted lower alkyl or ω-hydroxyalkyl, optionally substituted lower alkoxy and/or cyano, or $R^7$ and $R^{10}$ form together group of formula Q is $-CHR-$, $-CO-$ or $-SO_2-$;
r is 0 or 1;
R is hydrogen or lower alkyl; and
$R^3$ is hydroxy, $-O^-$, lower-alkoxy, or $-OM$ and M represents an alkali metal;
as well as readily hydrolyzable esters thereof, pharmaceutically acceptable salts of said compounds and hydrates of the compounds of formula I and of their esters and salts, as well as the preparation of such compounds, their use for the treatment of infectious diseases and pharmaceutical preparations containing such compounds.

25 Claims, No Drawings

FOREIGN PATENT DOCUMENTS

| | | |
|---|---|---|
| 0 723 965 | 7/1996 | (EP) . |
| 0 727 426 | 8/1996 | (EP) . |
| 0 761 673 | 3/1997 | (EP) . |
| 0 774 466 | 5/1997 | (EP) . |
| 0 812 846 | 12/1997 | (EP) . |
| 0 831 093 | 3/1998 | (EP) . |
| WO 92/04353 | 3/1992 | (WO) . |
| WO 94/10177 | 5/1994 | (WO) . |
| WO 96/26943 | 9/1996 | (WO) . |
| WO 97/03990 | 2/1997 | (WO) . |

OTHER PUBLICATIONS

Green, T., "Protective Groups in Organic Synthesis", Chapter 7, pp. 218–287 (1981).

English, J. Med. Chem 33, 344 (1990).

Ikeda, Chem. Pharm Bull 36 (1) 218 (1988).

Baltza, J. Antibiotics 33, 1183 (10/80).

Heinze–Krauss, et al., Synthesis and Structure–Activity Relationship of (Lactamylvinyl)cephalosporins Exhibiting Activity against Staphylococci, Pneumococci, and Enterococci, J. Med. Chem., vol. 39, pp. 1864–1871 (1996).

VINYLPYRROLIDINONE CEPHALOSPORIN DERIVATIVES

BACKGROUND OF THE INVENTION

This invention is in the field of antibacterial agents which are cephalosporin derivatives.

Certain cephalosporin derivatives are disclosed in PCT International Publication No.WO 96/26943, published Sep. 6, 1996 (F. Hoffmann-La Roche A G); U.S. Pat. No. 5,523,400, issued Jun. 4, 1996 (Wei et al.); European Patent Publication No. EP 0 699 681 A1, published Mar. 6, 1996 (Bristol-Myers Co.); and European Patent Publication No. EP 0 727 426 A2, published Aug. 21, 1996 (Bristol-Myers Co.).

SUMMARY OF THE INVENTION

The present invention provides cephalosporin derivatives of the formula

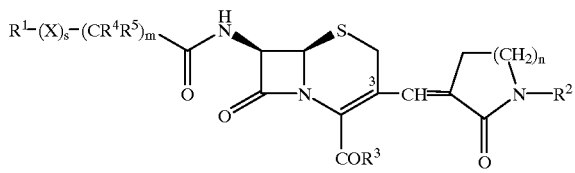

I where
- $R^1$ is halogen, lower alkyl, phenyl, benzyl, styryl, naphthyl or heterocyclyl; the lower alkyl, phenyl, benzyl, styryl, naphthyl and heterocyclyl being optionally substituted by at least one of halogen, hydroxy, optionally substituted lower alkyl, optionally substituted lower alkoxy, optionally substituted phenyl, amino, lower alkylamino, di-lower alkylamino, carboxy, lower alkylcarboxy, carbamoyl or lower alkylcarbamoyl;
- $R^4$, $R^5$ independently are hydrogen, lower alkyl or phenyl;
- X is S, O, NH or $CH_2$;
- n is 0, 1 or 2;
- m is 0 or 1;
- s is 0 or 1;
- $R^2$ is hydrogen, hydroxy, $-CH_2-CONHR^6$, lower alkyl-$Q_r$, cycloalkyl-$Q_r$, lower alkoxy, lower alkenyl, cycloalkenyl-$Q_r$, lower alkynyl, aralkyl-$Q_r$, aryl-$Q_r$, aryloxy, aralkoxy, a heterocyclic ring or a heterocyclyl-$Q_r$, the lower alkyl, cycloalkyl, lower alkoxy, lower alkenyl, cycloalkenyl, lower alkynyl, aralkyl, aryl, aryloxy, aralkoxy and the heterocyclic ring may be substituted with at least one group selected from carboxy, amino, nitro, cyano, $-SO_2NHR^6$, optionally fluoro substituted lower alkyl, lower alkoxy, hydroxy, halogen, $-CONR^6R^7$, $-CH_2CONR^6R^7$, $-N(R^7)COOR^8$, $R^7CO-$, $R^7OCO-$, $R^7COO-$, $-C(R^7R^9)CO_2R^8$, $-C(R^7R^9)CONR^7R^{10}$, wherein
- $R^6$ is hydrogen, lower alkyl, cycloalkyl or aryl;
- $R^7$ and $R^9$ are independently hydrogen or lower alkyl;
- $R^8$ is hydrogen, lower alkyl, lower alkenyl or a carboxylic acid protecting group; and
- $R^{10}$ is hydrogen, ω-hydroxy-alkyl, phenyl, naphthyl or heterocyclyl, the phenyl, naphthyl or heterocyclyl being unsubstituted or substituted with at least one of the groups of optionally protected hydroxy, halogen, optionally substituted lower alkyl or ω-hydroxyalkyl, optionally substituted lower alkoxy and/or cyano, or $R^7$ and $R^{10}$ form together group of formula

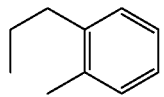

Q is $-CHR-$, $-CO-$ or $-SO_2-$;
r is 0 or 1;
R is hydrogen or lower alkyl; and
$R^3$ is hydroxy, $-O^-$, lower-alkoxy, or $-OM$ and M represents an alkali metal;
as well as readily hydrolyzable esters thereof, pharmaceutically acceptable salts of said compounds and hydrates of the compounds of formula I and of their esters and salts.

The compounds of formula I possess antibacterial activity against beta-lactam sensitive and resistant gram-positive bacteria, such as staphylococci, pneumococci, and enterococci. These compounds are useful both in vivo in the treatment of infectious diseases caused by such bacteria, as well as ex vivo as a disinfectant.

This invention also provides a process for producing a compound of the formula

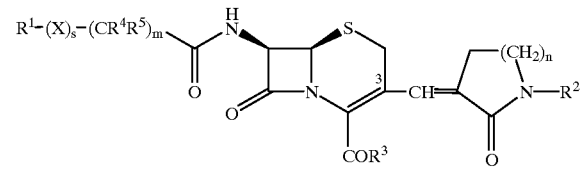

I wherein
- $R^1$ is halogen, lower alkyl, phenyl, benzyl, styryl, naphthyl or heterocyclyl; the lower alkyl, phenyl, benzyl, styryl, naphthyl and heterocyclyl being optionally substituted by at least one of halogen, hydroxy, optionally substituted lower alkyl, optionally substituted lower alkoxy, optionally substituted phenyl, amino, lower alkylamino, di-lower alkylamino, carboxy, lower alkylcarboxy, carbamoyl or lower alkylcarbamoyl;
- $R^4$, $R^5$ independently are hydrogen, lower alkyl or phenyl;
- X is S, O, NH or $CH_2$;
- n is 0, 1 or 2;
- m is 0 or 1;
- s is 0 or 1;
- $R^2$ is hydrogen, hydroxy, $-CH_2-CONHR^6$, lower alkyl-$Q_r$, cycloalkyl-$Q_r$, lower alkoxy, lower alkenyl, cycloalkenyl-$Q_r$, lower alkynyl, aralkyl-$Q_r$, aryl-$Q_r$, aryloxy, aralkoxy, a heterocyclic ring or a heterocyclyl-$Q_r$, the lower alkyl, cycloalkyl, lower alkoxy, lower alkenyl, cycloalkenyl, lower alkynyl, aralkyl, aryl, aryloxy, aralkoxy and the heterocyclic ring is optionally substituted with at least one group selected from carboxy, amino, nitro, cyano, $-SO_2NHR^6$, optionally fluoro substituted lower alkyl, lower alkoxy, hydroxy, halogen, $-CONR^6R^7$, $-CH_2CONR^6R^7$, $-N(R^7)COOR^8$, $R^7CO-$, $R^7OCO-$, $R^7COO-$, $-C(R^7R^9)CO_2R^8$, $-C(R^7R^9)CONR^7R^{10}$, wherein
- $R^6$ is hydrogen, lower alkyl, cycloalkyl or aryl;
- $R^7$ and $R^9$ are independently hydrogen or lower alkyl;

$R^8$ is hydrogen, lower alkyl, lower alkenyl or a carboxylic acid protecting group; and $R^{10}$ is hydrogen, ω-hydroxy-alkyl, phenyl, naphthyl or heterocyclyl, the phenyl, naphthyl or heterocyclyl being unsubstituted or substituted with at least one of the groups of optionally protected hydroxy, halogen, optionally substituted lower alkyl or ω-hydroxyalkyl, optionally substituted lower alkoxy and/or cyano, or $R^7$ and $R^{10}$ form together group of formula

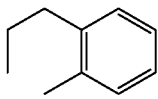

Q is —CHR—, —CO— or —SO$_2$—;

r is 0 or 1;

R is hydrogen or lower alkyl; and $R^3$ is hydroxy or —O$^-$;

which process comprises treating a compound of the formula

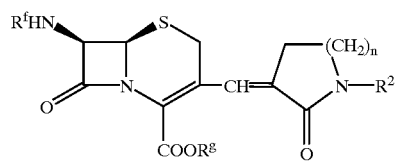

II in which $R^f$ is hydrogen or trimethylsilyl; and $R^g$ is hydrogen, benzhydryl, p-methoxybenzyl, t-butyl, trimethylsilyl or allyl or salt thereof, with a reagent of the formula

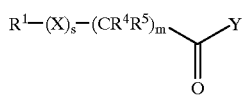

III in which Y is —OH or a reactive functional derivative thereof, and then removing $R^g$ when $R^g$ is benzhydryl, p-methoxybenzyl, t-butyl, trimethylsilyl or allyl or a salt thereof, thereby producing the compound of formula I.

DETAILED DESCRIPTION OF THE INVENTION

This invention provides a compound of the formula

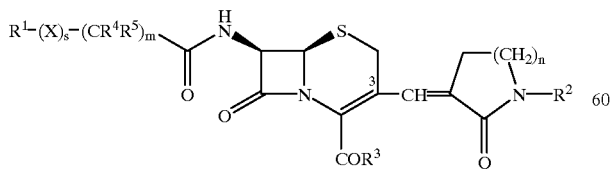

I wherein $R^1$ is halogen, lower alkyl, phenyl, benzyl, styryl, naphthyl or heterocyclyl; the lower alkyl, phenyl, benzyl, styryl, naphthyl and heterocyclyl being optionally substituted by at least one of halogen, hydroxy, optionally substituted lower alkyl, optionally substituted lower alkoxy, optionally substituted phenyl, amino, lower alkylamino, di-lower alkylamino, carboxy, lower alkylcarboxy, carbamoyl or lower alkylcarbamoyl;

$R^4$, $R^5$ independently are hydrogen, lower alkyl or phenyl;

X is S, O, NH or CH$_2$;

n is 0, 1 or 2;

m is 0 or 1;

s is 0 or 1;

$R^2$ is hydrogen, hydroxy, —CH$_2$—CONHR$^6$, lower alkyl-Q$_r$, cycloalkyl-Q$_r$, lower alkoxy, lower alkenyl, cycloalkenyl-Q$_r$, lower alkynyl, aralkyl-Q$_r$, aryl-Q$_r$, aryloxy, aralkoxy, a heterocyclic ring or a heterocyclyl-Q$_r$, the lower alkyl, cycloalkyl, lower alkoxy, lower alkenyl, cycloalkenyl, lower alkynyl, aralkyl, aryl, aryloxy, aralkoxy and the heterocyclic ring is optionally substituted with at least one group selected from carboxy, amino, nitro, cyano, —SO$_2$NHR$^6$, optionally fluoro substituted lower alkyl, lower alkoxy, hydroxy, halogen, —CONR$^6$R$^7$, —CH$_2$CONR$^6$R$^7$, —N(R$^7$)COOR$^8$, R$^7$CO—, R$^7$OCO—, R$^7$COO—, —C(R$^7$R$^9$)CO$_2$R$^8$, —C(R$^7$R$^9$)CONR$^7$R$^{10}$, wherein $R^6$ is hydrogen, lower alkyl, cycloalkyl or aryl;

$R^7$ and $R^9$ are independently hydrogen or lower alkyl;

$R^8$ is hydrogen, lower alkyl, lower alkenyl or a carboxylic acid protecting group; and $R^{10}$ is hydrogen, ω-hydroxy-alkyl, phenyl, naphthyl or heterocyclyl, the phenyl, naphthyl or heterocyclyl being unsubstituted or substituted with at least one of the groups of optionally protected hydroxy, halogen, optionally substituted lower alkyl or ω-hydroxyalkyl, optionally substituted lower alkoxy and/or cyano, or $R^7$ and $R^{10}$ form together group of formula

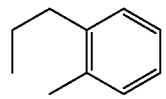

Q is —CHR—, —CO— or —SO$_2$—;

r is 0 or 1;

R is hydrogen or lower alkyl; and $R^3$ is hydroxy, —O$^-$, lower-alkoxy, or —OM and M is an alkali metal;

a readily hydrolyzable ester thereof, a pharmaceutically acceptable salt thereof, or a hydrate thereof, or a hydrate of said ester or said salt.

In above compounds of formula I the substituent in position 3 can be present in the E-form:

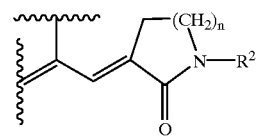

or in the Z-form:

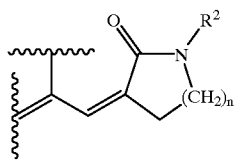

Compounds of formula I i.e. wherein the substituent in position 3 is in the E-form are generally preferred.

In a particular embodiment of the compounds of formula I n is 1.

The term "halogen" or "halo" used herein refers to all four forms, that is chlorine or chloro; bromine or bromo; iodine or iodo; and fluorine or fluoro, unless specified otherwise.

As used herein, the terms "alkyl" and "lower alkyl" refer to both straight and branched chain saturated hydrocarbon groups having 1 to 8, and preferably 1 to 4, carbon atoms, for example, methyl, ethyl, n-propyl, isopropyl, t-butyl and the like.

By the term "optionally substituted lower alkyl" is meant a "lower alkyl" moiety as defined above substituted by, for example, halogen, amino, hydroxy, cyano, carboxy etc., such as carboxymethyl, 2-fluoroacetyl, trifluoromethyl, 2,2, 2-trifluoroethyl, 2-chloroethyl, 2-hydroxyethyl and like.

As used herein, the term "lower alkoxy" refers to a straight or branched chain hydrocarbonoxy group wherein the "alkyl" portion is a lower alkyl group as defined above. Examples include methoxy, ethoxy, n-propoxy and the like. The "alkyl" portion may be substituted as defined above.

As used herein, "alkenyl" and "lower alkenyl" refer to unsubstituted or substituted hydrocarbon chain radical having from 2 to 8 carbon atoms, preferably from 2 to 4 carbon atoms, and having at least one olefinic double bond, e.g. allyl, vinyl etc.

As used herein, "lower alkynyl" refers to unsubstituted or substituted hydrocarbon chain radical having from 2 to 8 carbon atoms, preferably 2 to 4 carbon atoms, and having at least one triple bond.

By the term "cycloalkyl" is meant a 3–7 membered saturated carbocyclic moiety, e.g., cyclopropyl, cyclobutyl, cyclohexyl, etc.

As used herein, "cycloalkenyl" refers to a carbocyclic ring radical having at least one olefinic double bond.

By the term "aryl" is meant a radical derived from an aromatic hydrocarbon by the elimination of one atom of hydrogen and can be substituted or unsubstituted. The aromatic hydrocarbon can be mononuclear or polynuclear. Examples of aryl of the mononuclear type include phenyl, tolyl, xylyl, mesityl, cumenyl, and the like. Examples of aryl of the polynuclear type include naphthyl, anthryl, phenanthryl, and the like. The aryl group can have at least one substituent selected from, as for example, halogen, hydroxy, cyano, carboxy, nitro, amino, lower alkyl, lower alkoxy, carbamoyl, such as in 2,4-difluorophenyl, 4-carboxyphenyl, 4-nitrophenyl, 4-aminophenyl, 4-methoxyphenyl.

By the term "aralkyl" is meant an alkyl group containing an aryl group. It is a hydrocarbon group having both aromatic and aliphatic structures, that is, a hydrocarbon group in which a lower alkyl hydrogen atom is substituted by a monocyclic aryl group, e.g., phenyl, tolyl, etc.

As used herein, "aryloxy" is an oxygen radical having an aryl substituent (i.e., —O-aryl).

As used herein, "aralkoxy" is an oxygen radical having an aralkyl substituent.

As used herein, the term "lower alkylamino and di-lower alkylamino" refers to mono and dialkylamino residues wherein lower alkyl is as defined above, for example, N-methylamino, N-ethylamino, N,N-dimethylamino, N,N-diethylamino and the like.

As used herein, "heterocyclic ring" refers to an unsaturated or saturated, unsubstituted or substituted 4-, 5-, 6-, or 7-membered heterocyclic ring containing at least one hetero atom selected from the group consisting of oxygen, nitrogen, or sulfur. Exemplary heterocyclic rings include, but are not limited to, for example, the following groups: azetidinyl, pyridyl, pyrazinyl, piperidyl, piperidino, N-oxido-pyridyl, pyrimidyl, piperazinyl, pyrrolidinyl, pyridazinyl, N-oxide-pyridazinyl, pyrazolyl, triazinyl, imidazolyl, thiazolyl, 1,2, 3-thiadiazolyl, 1,2,4-thiadiazolyl, 1,3,4-thiadiazolyl, 1,2,3-oxadiazolyl, 1,2,4-oxadiazolyl, 1,3,4-oxadiazolyl, 1,2,3-triazolyl, 1,2,4-triazolyl, 1H-tetrazolyl, 2H-tetrazolyl; furyl, 1H-azepinyl, thiophenyl, tetrahydrothiophenyl, isoxazolyl, isothiazolyl, oxazolidinyl, etc. Substituents for the heterocyclic ring include, for example, lower alkyls such as methyl, ethyl, propyl, etc., lower alkoxys such as methoxy, ethoxy, etc., halogens such as fluorine, chlorine, bromine, etc., halogen substituted alkyls such as trifluoromethyl, trichloroethyl, etc., amino, mercapto, hydroxyl, carbamoyl, or carboxyl groups. A further substituent is oxo, such as in 2-oxo-oxazolidin-3-yl, 1,1-dioxo-tetrahydrothiophen-3-yl. Further examples of substituted heterocycles are 6-methoxy-pyridin-3-yl, 5-methyl-isoxazol-3-yl, 1-methyl-pyridinium-2-yl, -3-yl, -4-yl, 1-carbamoylmethyl-pyridinium-2-yl, 1-carbamoylmethyl-pyridinium-3-yl, 1-carbamoylmethyl-pyridinium-2-yl, -3-yl, -4-yl, 1-[N-(3-fluoro-4-hydroxy)phenyl]-carbamoylmethyl-pyridinium-2-yl.

By the term "substituted phenyl" is meant phenyl mono or di-substituted by halogen, optionally substituted lower alkyl, optionally protected hydroxy or amino, nitro or trifluoromethyl.

The term "optionally protected hydroxy" refers to hydroxy or hydroxy protected, for example with t-butyloxycarbonyl, trimethylsilyl, t-butyl-dimethylsilyl, tetrahydropyranyl, trifluoroacetyl, and the like, or refers to an ester group, for example, phosphate or sulfonate.

The term "optionally protected amino" refers to amino or amino protected with, for example, BOC [t-butoxycarbonyl; other name: (1,1-dimethylethoxy)carbonyl], benzyloxycarbonyl and allyloxycarbonyl.

As used herein the term "pharmaceutically acceptable salts" means salts derived from metals, the ammonium salt, quaternary ammonium salts derived from organic bases and amino acid salts. Examples of preferred metal salts are those derived from the alkali metals, for example, lithium ($Li^+$), sodium ($Na^+$) and potassium ($K^+$). Examples of quaternary ammonium salts derived from organic bases include tetramethylammonium ($N^+(CH_3)_4$), tetraethylammonium ($N^+(CH_2CH_3)_4$), benzyltrimethylammonium ($N^+(C_6H_5CH_2)(CH_3)_3$), phenyltriethylammonium ($N^+(C_6H_5)(CH_2CH_3)_3$), and the like, etc. Those salts derived from amines include salts with N-ethylpiperidine, procaine, dibenzylamine, N,N'-dibenzylethylenediamine, alkylamines or dialkylamines as well as salts with amino acids such as, for example, salts with arginine or lysine. Especially preferred are hydrochlorides, sulfates, phosphates, lactates, mesylates or the inner salt.

The term "amino protecting groups" refers to protecting groups conventionally used to replace an acidic proton of an amino group. Examples of such groups are described in Green, T., Protective Groups in Organic Synthesis, Chapter 7, John Wiley and Sons, Inc. (1981), pp. 218–287, herein incorporated by reference. Preferably these examples include carbamates, e.g fluorenylmethyl, 2,2,2-trichloroethyl, 2-haloethyl, 2-(trimethylsilyl)ethyl, t-butyl, allyl, benzyl. Further protecting groups are 3,5- dimethoxybenzyl, p-nitro-benzyl, diphenylmethyl, triphenylmethyl, benzyl, formyl, acetyl, trifluoroacetyl, chloroacetyl, the cyclic imides of N-phthaloyl, N-trimethylsilyl, N-benzenesulfonyl, N-toluenesulfonyl, N-p-methylbenzyl-sulfonyl. Preferred is BOC [t-butoxycarbonyl, other name (1,1-dimethylethoxy) carbonyl], benzyloxycarbonyl and allyloxycarbonyl.

The term "carboxylic acid protecting group" refers to protecting groups conventionally used to replace the acidic proton of a carboxylic acid. Examples of such groups are described in Greene, T., Protective Groups in Organic Synthesis, Chapter 5, pp. 152–192 (John Wiley and Sons, Inc. 1981), incorporated herein by reference. Preferably these examples include methoxymethyl, methylthiomethyl, 2,2,2-trichloroethyl, 2-haloethyl, 2-(trimethylsilyl)ethyl, t-butyl, allyl, benzyl, triphenylmethyl (trityl), benzhydryl, p-nitrobenzyl, p-methoxybenzyl, trimethylsilyl, triethylsilyl, t-butyldimethylsilyl, i-propyl-dimethylsilyl. Preferred are benzyhydryl, t-butyl, p-nitrobenzyl, p-methoxybenzyl and allyl.

The term "hydroxy protecting group" refers to protecting groups as conventionally used in the art such as trimethylsilyl, t-butyl-dimethylsilyl, dimethylphenylsilyl, triphenylmethyl, lower alkanoyl, acetyl, tetrahydro-pyranyl, benzyl, p-nitrobenzyl or t-butyloxycarbonyl.

As readily hydrolyzable esters of the compounds of formula I there are to be understood compounds of formula I, the carboxy group(s) of which (for example, the 2-carboxy group) is/are present in the form of readily hydrolyzable ester groups. As used herein, "readily hydrolyzable esters" means the lower alkanoyloxy-alkyl esters (e.g., the acetoxymethyl, pivaloyloxymethyl, 1-acetoxyethyl and 1-pivaloyloxyethyl ester); the lower alkoxycarbonyloxy-alkyl esters (e.g., the methoxycarbonyloxymethyl, 1-ethoxycarbonyloxyethyl and 1-isopropoxycarbonyloxyethyl ester); the lactonyl esters (e.g., the phthalidyl and thiophthalidyl ester); the lower alkoxymethyl esters (e.g., the methoxymethyl ester); the lower alkanoylanminomethyl esters (e.g., the acetamidomethyl ester); the benzyl and cyanomethyl esters; 2,2-dimethyl-1-oxopropoxy)methyl ester; 2-[(2-methylpropoxy) carbonyl]-2-pentenyl ester; 1-[[(1-methylethoxy)-carbonyl] oxy] ethyl ester; 1-(acetyloxy) ethyl ester; (5-methyl-2-oxo-1,3-dioxol-4-yl) methyl ester; 1-[[(cyclohexyloxy)carbonyl] oxy] ethyl ester; and 3,3-dimethyl-2-oxobutyl ester. It will be appreciated by those of ordinary skill in the art that the readily hydrolyzable esters of the compounds of the present invention can be formed at a free carboxy group of the compound.

4-trifluoromethylphenyl, 4-methoxyphenyl, 4-hydroxymethylphenyl, 3,4-dimethoxyphenyl, 4-methyl-1, 2,4-triazol-5-yl, 1-methyl-tetrazol-5-yl, pyrimidin-2-yl, optionally substituted pyridinium-1-yl, 2-yl, -3-yl or -4-yl, benzimidazol-2-yl, 2-benzthiazolyl, 4-pyridinyl, (2-amino)-thiazol-4-yl, 2-naphthyl, benzyl. In another preferred embodiment, both when n is 0, 1 or 2 and when n is 1, $R^2$ is methylcyclopropyl, 2-, 3- or 4-hydroxybenzyl, pyrrolidin-3-yl or a group of formula

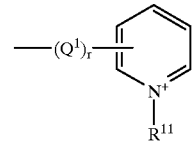

wherein $Q^1$ is —$CH_2$— r is 0 or 1;

$R^{11}$ is hydrogen, lower alkyl, ω-hydroxy alkyl, benzyl or alkyl-heterocyclyl, the benzyl and the heterocyclyl group being unsubstituted or substituted with at least one of the groups cyano, carboxy or hydroxy; or is —$CH_2CONR^7R^{10}$; wherein $R^7$ and $R^{10}$ are as defined above.

In a still more preferred embodiment, both $R^1$ and $R^2$ are as defined in the preceding paragraph.

The compounds of formula I as well as their salts and readily hydrolyzable esters can be hydrated. The hydration can be effected in the course of the manufacturing process or can occur gradually as a result of hygroscopic properties of an initially anhydrous product.

Especially preferred compounds of formula I are (E)-(6R, 7R)-3-[1-[1-[(4-Hydroxy-phenylcarbamoyl)-methyl]-pyridin-1-ium-4-ylmethyl]-2-oxo-pyrrolidin-3-ylidenemethyl]-8-oxo-7-[2-(2,4,5-trichloro-phenyl-sulfanyl)-acetylamino]-5-thia-1-aza-bicyclo[4.2.0]oct-2-ene-2-carboxylate

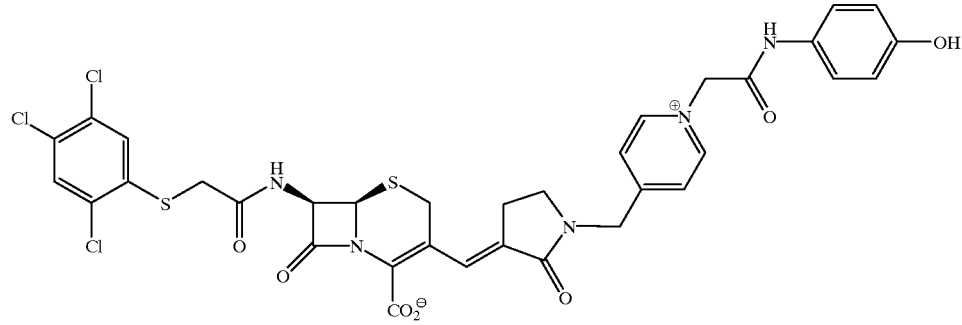

Examples of salts of the compounds of formula I are defined under "pharmaceutically acceptable salts" above.

In the compounds of formula I described herein, both when n is 0, 1 or 2 and when n is 1, in one preferred embodiment $R^1$ is selected from the groups phenyl, 2,4,5-trichlorophenyl, 3,4-dichlorophenyl, 2,5-dichlorophenyl, (E)-(6R,7R)-3-[1-[1-[(4-Hydroxy-phenylcarbamoyl)-methyl]-pyridin-1-ium-4-ylmethyl]-2-oxo-pyrrolidin-3-ylidenemethyl]-8-oxo-7-[2-(1-benzothiazol-2-yl-sulfanyl)-acetylamino]-5-thia-1-aza-bicyclo[4.2.0]oct-2-ene-2-carboxylate

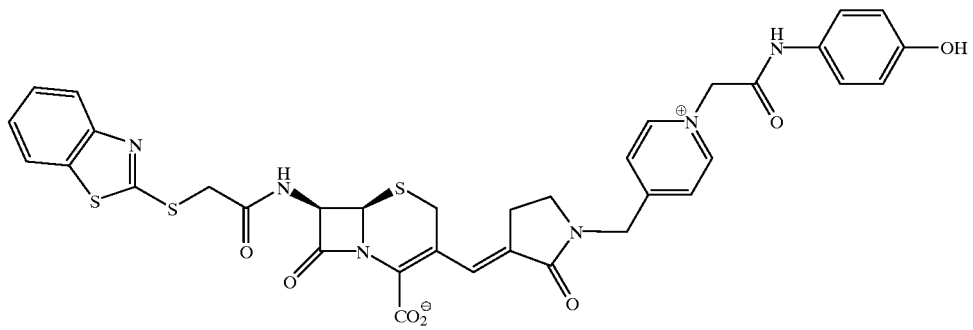

(E)-(6R,7R)-3-(1-Cyclopropylmethyl-2-oxo-pyrrolidin-3-ylidenemethyl)-8-oxo-7-[2-(2,4,5-trichloro-phenylsulfanyl)-acetylamino]-5-thia-1-aza-bicyclo[4.2.0]oct-2-ene-2-carboxylic acid

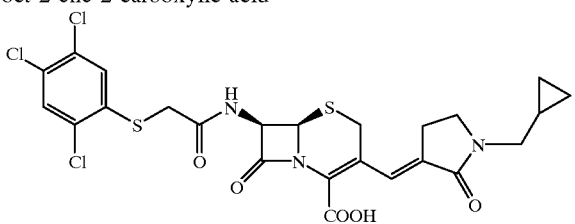

(E)-(6R,7R)-7-[2-(Benzothiazol-2-ylsulfanyl)-acetylamino]-3-(1-cyclopropylmethyl-2-oxo-pyrrolidin-3-ylidenemethyl)-8-oxo-5-thia-1-aza-bicyclo[4.2.0]oct-2-ene-2-carboxylic acid

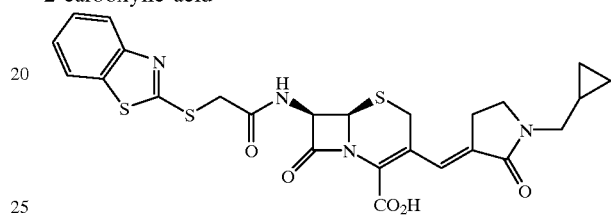

(E)-(6R,7R)-3-[1-[1-[(4-Hydroxy-phenylcarbamoyl)-methyl]-pyridin-1-ium-4-ylmethyl]-2-oxo-pyrrolidin-3-ylidenemethyl]-8-oxo-7-[2-(pyridin-4-ylsulfanyl)-acetylamino]-5-thia-1-aza-bicyclo[4.2.0]oct-2-ene-2-carboxylate

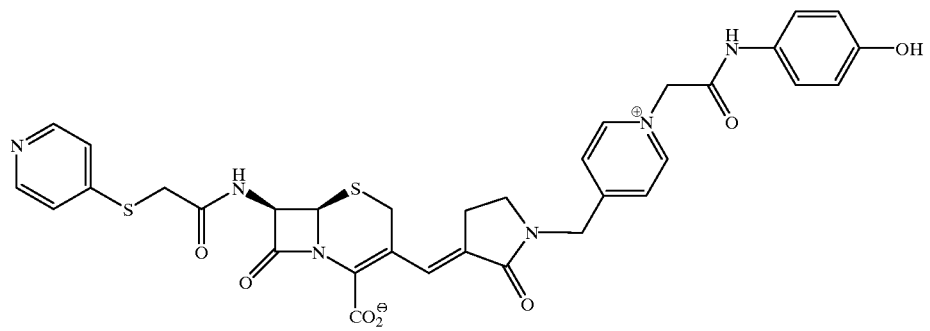

(E)-(6R,7R)-3-[1-[1-[(3-Fluoro-4-hydroxy-phenylcarbamoyl)-methyl]-pyridin-1-ium-4-ylmethyl]-2-oxo-pyrrolidin-3-ylidenemethyl]-8-oxo-7-(2,4,5-trichlorophenylsulfanyl)-acetylamino)-5-thia-1-aza-bicyclo[4.2.0]oct-2-ene-2-carboxylate

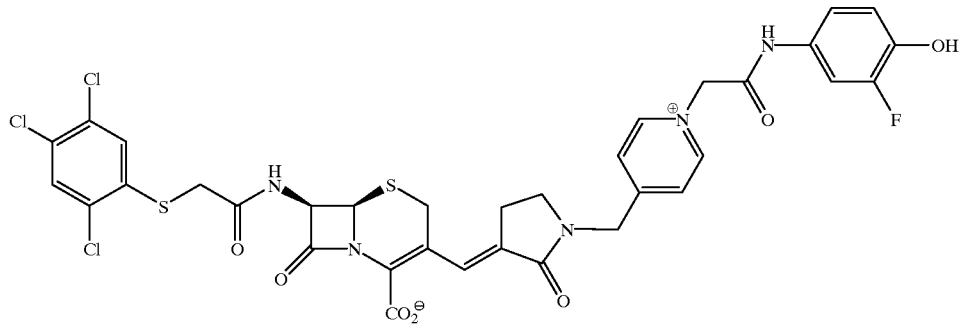

(E)-(6R,7R)-3-[1-[1-((4-Hydroxy-phenylcarbamoyl)-methyl]-pyridin-1-ium-4-ylmethyl]-2-oxo-pyrrolidin-3-ylidenemethyl]-8-oxo-7-(2-phenylsulfanyl-acetyl-amino)-5-thia-1-aza-bicyclo[4.2.0]oct-2-ene-2-carboxylate

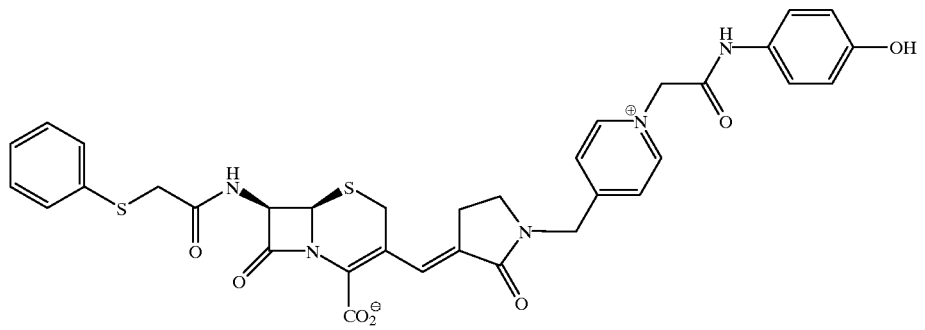

(E)-(6R,7R)-3-[1-[1-[(3-Fluoro-4-hydroxy-phenylcarbamoyl)-methyl]-pyridin-1-ium-4-ylmethyl]-2-oxo-pyrrolidin-3-ylidenemethyl]-7-[2-(naphthalen-2-yl-sulfanyl)-acetylamino]-8-oxo-5-thia-1-aza-bicyclo[4.2.0]oct-2-ene-2-carboxylate

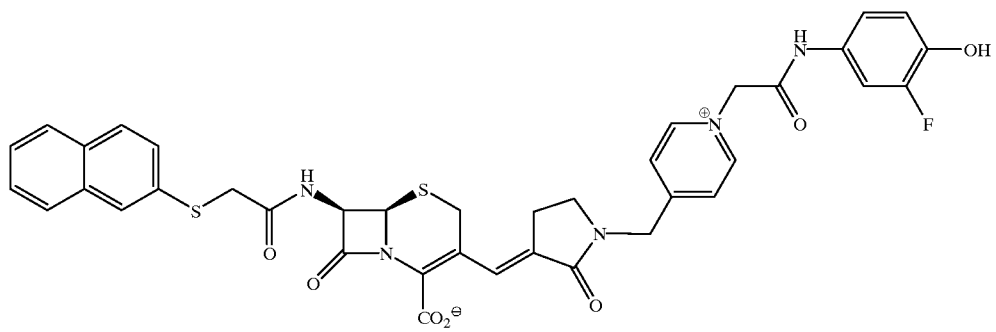

(E)-(6R,7R)-7-[(2-(3,4-Dichloro-phenylsulfanyl)-acetylamino]-3-[1-[1-[(3-fluoro-4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate

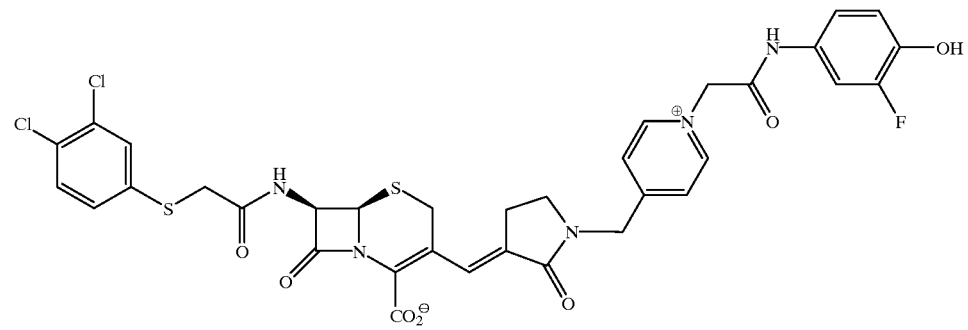

(E)-(6R,7R)-3-[1-(3-Hydroxy-benzyl)-2-oxo-pyrrolidin-3-ylidenemethyl]-8-oxo-7-[2-(2,4,5-trichloro-phenylsulfanyl)-acetylamino]-5-thia-1-aza-bicyclo[4.2.0]oct-2-ene-2-carboxylic acid

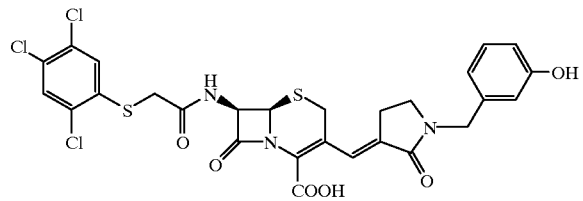

(E)-(6R,7S)-3-[1-(3-Hydroxy-benzyl)-2-oxo-pyrrolidin-3-ylidenemethyl]-8-oxo-7-[2-naphthalen-2-ylsulfanyl)-acetylamino]-5-thia-1-aza-bicyclo[4.2.0]oct-2-ene-2-carboxylic acid

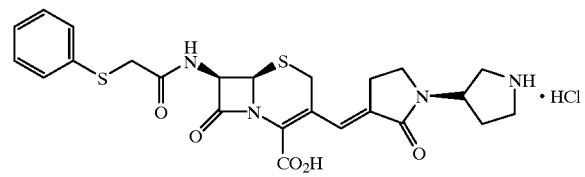

(E)-(6R,7R)-3-[1-[1-[(3-Fluoro-4-hydroxy-phenylcarbamoyl)-methyl]-pyridin-1-ium-4-ylmethyl]-2-oxo-pyrrolidin-3-ylidenemethyl]-8-oxo-7-(2-phenylsulfanyl-acetylamino)-5-thia-1-aza-bicyclo[4.2.0]oct-2-ene-2-carboxylate

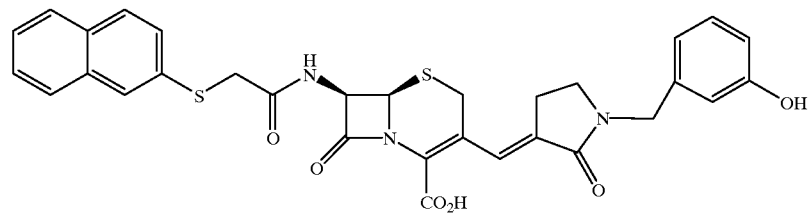

Mixture of (E)-(6R,7R)-8-oxo-3-[(R)- and -[(S)-2-oxo-[1,3']Bipyrrolidinyl-3-ylidenemethyl]-8-oxo-7-[2-(2,4,5-trichloro-phenylsulfanyl)-acetylamino]-5-thia-1-aza-bicyclo[4.2.0]oct-2-ene-2-carboxylic acid hydrochloride

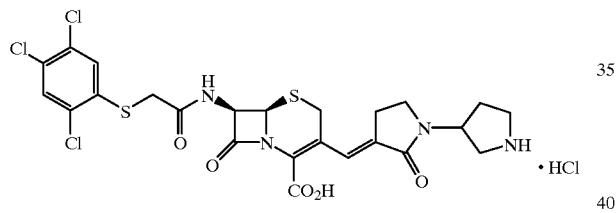

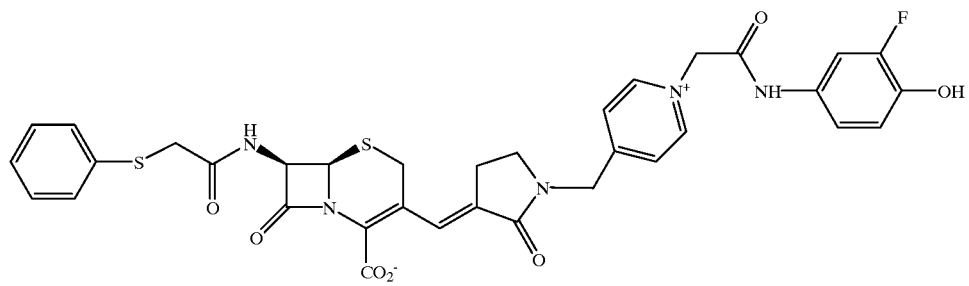

E)-(6R,7R)-8-Oxo-3-[(R)-2-oxo-[1,3']bipyrrolidinyl-3-ylidenemethyl]-7-(2-henylsulfanyl-acetylamino)-5-thia-1-aza-bicyclo[4.2.0]oct-2-ene-2-carboxylicacid hydrochloride (1:1)

(E)-(6R,7R)-7-[2-(2,5-Dichloro-phenylsulfanyl)-acetylamino]-3-[1-[(3-fluoro-4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate

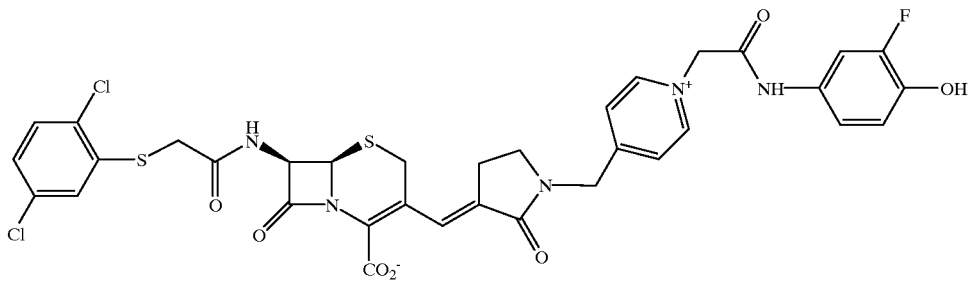

(E)-(6R,7R)-3-(1-Cyclopropyl-2-oxo-pyrrolidin-3-ylidenemethyl)-7-[2-(naphthalen-1-ylsulfanyl)-acetylamino]-8-oxo-5-thia-1-aza-bicyclo[4.2.0]oct-2-ene-2-carboxylic acid imidazole salt (1:1)

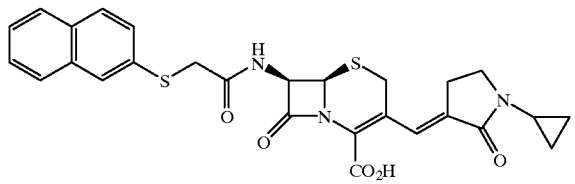

The compounds of the present invention are useful as antibiotics against beta-lactam sensitive and resistant gram-positive bacteria, such as staphylococci (e.g. methicillin-resistent staphylococci (MRSA)), pneumococci, and enterococci. The products in accordance with the invention can be used as medicaments, for example, in the form of pharmaceutical preparations for parenteral administration, and for this purpose are preferably made into preparations as lyophilisates or dry powders for dilution with customary agents, such as water or isotonic common salt solution. This invention provides a pharmaceutical composition containing a compound of any of the embodiments of formula I described herein in a daily dosage amount or single dose amount as described in the following paragraph, and a therapeutically inert carrier. This invention also provides a method of preventing (prophylaxis) and/or treating a gram-positive bacteria-related infectious disease in a mammalian subject which comprises administering to the subject a compound of any of the embodiments of formula I described herein in a daily dosage amount or single dose amount as described in the following paragraph.

Depending on the nature of the pharmacologically active compound the pharmaceutical preparations can contain the compound for the prevention and treatment of infectious diseases in mammals, human and non-human, a daily dosage of about 10 mg to about 4000 mg, especially about 50 mg to about 3000 mg, is usual, with those of ordinary skill in the art appreciating that the dosage will depend also upon the age, conditions of the mammals, and the kind of diseases being prevented or treated. The daily dosage can be administered in a single dose or can be divided over several doses. An average single dose of about 50 mg, 100 mg, 250 mg, 500 mg, 1000 mg, and 2000 mg can be contemplated.

Representative compounds (A to I, below) of the present invention were tested. In vitro activity was determined by minimum inhibitory concentration in a microorganism spectrum by the agar dilution method in Mueller Hinton agar, inoculum=$10^4$ CFU/spot.

A: (E)-(6R,7R)-3-[1-[1-[(4-Hydroxy-phenylcarbamoyl)-methyl]-pyridin-1-ium-4-ylmethyl]-2-oxo-pyrrolidin-3-ylidenemethyl]-8-oxo-7-[2-(2,4,5-trichloro-phenylsulfanyl)-acetylamino]-5-thia-1-aza-bicyclo[4.2.0]oct-2-ene-2-carboxylate B: (E)-(6R,7R)-3-[1-[1-[(4-Hydroxy-phenylcarbamoyl)-methyl]-pyridin-1-ium-4-ylmethyl]-2-oxo-pyrrolidin-3-ylidenemethyl]-8-oxo-7-[2-(1-benzothiazol-2-ylsulfanyl)-acetylamino]-5-thia-1-aza-bicyclo[4.2.0]oct-2-ene-2-carboxylate C: (E)-(6R,7R)-7-[2-(Benzothiazol-2-ylsulfanyl)-acetylamino]-3-(1-cyclopropyl-methyl-2-oxo-pyrrolidin-3-ylidenemethyl)-8-oxo-5-thia-1-aza-bicyclo[4.2.0]oct-2-ene-2-carboxylic acid D: (E)-(6R,7R)-3-[1-(1-[(4-Hydroxy-phenylcarbamoyl)-methyl]-pyridin-1-ium-4-ylmethyl]-2-oxo-pyrrolidin-3-ylidenemethyl-8-oxo-7-[2-(pyridin-4-ylsulfanyl)-acetylamino]-5-thia-1-aza-bicyclo[4.2.0]oct-2-ene-2-carboxylate E: (E)-(6R,7R)-3-[1-[1-[(3-Fluoro-4-hydroxy-phenylcarbamoyl)-methyl]-pyridin-1-ium-4-ylmethyl]-2-oxo-pyrrolidin-3-ylidenemethy]-7-[2-(naphthalen-2-ylsulfanyl)-acetylamino]-8-oxo-5-thia-1-aza-bicyclo[4.2.0]oct-2-ene-2-carboxylate F: (E)-(6R,7R)-3-[1-(3-Hydroxy-benzyl)-2-oxo-pyrrolidin-3-ylidenemethyl)-8-oxo-7-[2-(2,4,5-trichloro-phenylsulfanyl)-acetylamino]-5-thia-1-aza-bicyclo[4.2.0]oct-2-ene-2-carboxylic acid G: (E)-(6R,7S)-3-[1-(3-Hydroxy-benzyl)-2-oxo-pyrrolidin-3-ylidenemethyl]-8-oxo-7-[2-naphthalen-2-ylsulfanyl)-acetylamino]-5-thia-1-aza-bicyclo[4.2.0]oct-2-ene-2-carboxylic acid H: Mixture (1:1) of (E)-(6R,7R)-8-oxo-3-1(R)- and -[(S)-2-oxo-[1,3']Bipyrrolidinyl-3-ylidenemethyl]-8-oxo-7-[2-(2,4,5-trichloro-phenylsulfanyl)-acetylaminol-5-thia-1-aza-bicyclo[4.2.0]oct-2-ene-2-carboxylic acid hydrochloride I: (E)-(6R,7R)-3-[1-[1-[(3-Fluoro-4-hydroxy-phenylcarbamoyl)-methyl]-pyridin-1-ium-4-ylmethyl]-2-oxo-pyrrolidin-3-ylidenemethyl]-8-oxo-7-(2-phenylsulfanyl-acetylamino)-5-thia-1-aza-bicyclo[4.2.0]oct-2-ene-2-carboxylate In Vitro Activity Against Sensitive and Resistant *S. Aureus* MIC [μg/m]

|  | A | B | C | D | E | F | G | H | I |
|---|---|---|---|---|---|---|---|---|---|
| MIC S. aureus 6538 (MSSA) | ≦0.06 | 0.12 | 0.25 | 0.5 | 0.25 | 0.12 | 0.12 | ≦0.06 | ≦0.06 |
| MIC S. aureus 270A (MRSA) | 1 | 1 | 2 | 4 | 1 | 2 | I | 1 | 1 |

Agar Dilution Method on Mueller-Hinton Agar, Inoculum: $10^4$ CFU/spot

This invention also provides compounds of formula I according to each of the embodiments thereof described hereinabove, when prepared according to each of the embodiments of the process described below.

This invention provides a process for producing a compound of the formula

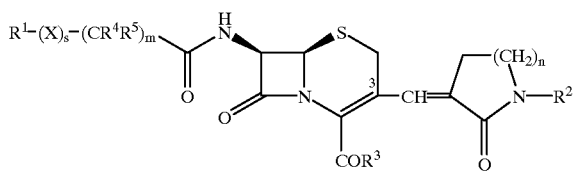

I wherein
- $R^1$ is halogen, lower alkyl, phenyl, benzyl, styryl, naphthyl or heterocyclyl; the lower alkyl, phenyl, benzyl, styryl, naphthyl and heterocyclyl being optionally substituted by at least one of halogen, hydroxy, optionally substituted lower alkyl, optionally substituted lower alkoxy, optionally substituted phenyl, amino, lower alkylamino, di-lower alkylamino, carboxy, lower alkylcarboxy, carbamoyl or lower alkylcarbamoyl;
- $R^4$, $R^5$ independently are hydrogen, lower alkyl or phenyl;
- X is S, O, NH or $CH_2$;
- n is 0, 1 or 2;
- m is 0 or 1;
- s is 0 or 1;
- $R^2$ is hydrogen, hydroxy, —$CH_2$—$CONHR^6$, lower alkyl-$Q_r$, cycloalkyl-$Q_r$, lower alkoxy, lower alkenyl, cycloalkenyl-$Q_r$, lower alkynyl, aralkyl-$Q_r$, aryl-$Q_r$, aryloxy, aralkoxy, a heterocyclic ring or a heterocyclyl-$Q_r$, the lower alkyl, cycloalkyl, lower alkoxy, lower alkenyl, cycloalkenyl, lower alkynyl, aralkyl, aryl, aryloxy, aralkoxy and the heterocyclic ring is optionally substituted with at least one group selected from carboxy, amino, nitro, cyano, —$SO_2NHR^6$, optionally fluoro substituted lower alkyl, lower alkoxy, hydroxy, halogen, —$CONR^6R^7$, —$CH_2CONR^6R^7$, —$N(R^7)$ $COOR^8$, $R^7CO$—, $R^7OCO$—, $R^7COO$—, —$C(R^7R^9)$ $CO_2R^8$, —$C(R^7R^9)CONR^7R^{10}$, wherein
  - $R^6$ is hydrogen, lower alkyl, cycloalkyl or aryl;
  - $R^7$ and $R^9$ are independently hydrogen or lower alkyl;
  - $R^8$ is hydrogen, lower alkyl, lower alkenyl or a carboxylic acid protecting group; and
  - $R^{10}$ is hydrogen, ω-hydroxy-alkyl, phenyl, naphthyl or heterocyclyl, the phenyl, naphthyl or heterocyclyl being unsubstituted or substituted with at least one of the groups of optionally protected hydroxy, halogen, optionally substituted lower alkyl or ω-hydroxyalkyl, optionally substituted lower alkoxy and/or cyano, or $R^7$ and $R^{10}$ form together group of formula

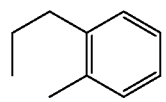

- Q is —CHR—, —CO— or —$SO_2$—;
- r is 0 or 1;
- R is hydrogen or lower alkyl; and
- $R^3$ is hydroxy or —$O^-$;

which process comprises treating a compound of the formula

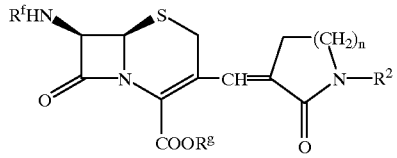

II in which
- $R^f$ is hydrogen or trimethylsilyl; and
- $R^g$ is hydrogen, benzhydryl, p-methoxybenzyl, t-butyl, trimethylsilyl or allyl or salt thereof, with a reagent of the formula

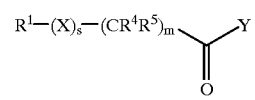

III in which Y is —OH or a reactive functional derivative thereof, and then removing $R^g$ when $R^g$ is benzhydryl, p-methoxybenzyl, t-butyl, trimethylsilyl or allyl or a salt thereof, thereby producing the compound of formula I.

This invention also provides an esterification of the product of the process described above, namely, a process for producing a compound of the formula

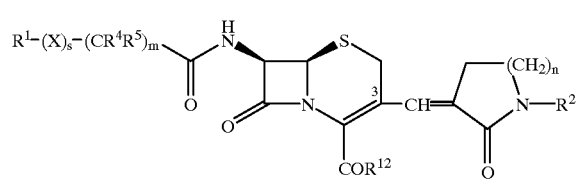

V wherein
- $R^1$ is halogen, lower alkyl, phenyl, benzyl, styryl, naphthyl or heterocyclyl; the lower alkyl, phenyl, benzyl, styryl, naphthyl and heterocyclyl being optionally substituted by at least one of halogen, hydroxy, optionally substituted lower alkyl, optionally substituted lower alkoxy, optionally substituted phenyl, amino, lower alkylamino, di-lower alkylamino, carboxy, lower alkylcarboxy, carbamoyl or lower alkylcarbamoyl;

$R^4$, $R^5$ independently are hydrogen, lower alkyl or phenyl;

X is S, O, NH or $CH_2$;

n is 0, 1 or 2;

m is 0 or 1;

s is 0 or 1;

$R^2$ is hydrogen, hydroxy, —$CH_2$—$CONHR^6$, lower alkyl-$Q_r$, cycloalkyl-$Q_r$, lower alkoxy, lower alkenyl, cycloalkenyl-$Q_r$, lower alkynyl, aralkyl-$Q_r$, aryl-$Q_r$, aryloxy, aralkoxy, a heterocyclic ring or a heterocyclyl-$Q_r$, the lower alkyl, cycloalkyl, lower alkoxy, lower alkenyl, cycloalkenyl, lower alkynyl, aralkyl, aryl, aryloxy, aralkoxy and the heterocyclic ring is optionally substituted with at least one group selected from carboxy, amino, nitro, cyano, —$SO_2NHR^6$, optionally fluoro substituted lower alkyl, lower alkoxy, hydroxy, halogen, —$CONR^6R^7$, —$CH_2CONR^6R^7$, —$N(R^7)COOR^8$, $R^7CO$—, $R^7OCO$—, $R^7COO$—, —$C(R^7R^9)CO_2R^8$, —$C(R^7R^9)CONR^7R^{10}$, wherein $R^6$ is hydrogen, lower alkyl, cycloalkyl or aryl;

$R^7$ and $R^9$ are independently hydrogen or lower alkyl;

$R^8$ is hydrogen, lower alkyl, lower alkenyl or a carboxylic acid protecting group; and $R^{10}$ is hydrogen, ω-hydroxy-alkyl, phenyl, naphthyl or heterocyclyl, the phenyl, naphthyl or heterocyclyl being unsubstituted or substituted with at least one of the groups of optionally protected hydroxy, halogen, optionally substituted lower alkyl or ω-hydroxyalkyl, optionally substituted lower alkoxy and/or cyano, or $R^7$ and $R^{10}$ form together group of formula

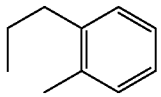

Q is —CHR—, —CO— or —$SO_2$—;

r is 0 or 1;

R is hydrogen or lower alkyl; and $R^{12}$ is lower alkoxy;

which process comprises treating a compound produced by the process of claim 10 with a halide of the formula $R^{12}$-U wherein U is a halogen, thereby producing the compound of formula V.

This invention provides a process for producing a compound of the general formula

I

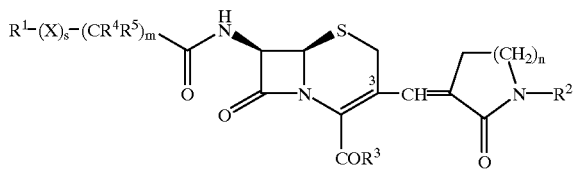

wherein $R^1$ is halogen, lower alkyl, phenyl, benzyl, styryl, naphthyl or heterocyclyl; the lower alkyl, phenyl, benzyl, styryl, naphthyl and heterocyclyl being optionally substituted by at least one of halogen, hydroxy, optionally substituted lower alkyl, optionally substituted lower alkoxy, optionally substituted phenyl, amino, lower alkylamino, di-lower alkylamino, carboxy, lower alkylcarboxy, carbamoyl or lower alkylcarbamoyl;

$R^4$, $R^5$ independently are hydrogen, lower alkyl or phenyl;

X is S, O, or NH;

n is 0, 1 or 2;

m is 0 or 1;

s is 0 or 1;

$R^2$ is hydrogen, hydroxy, —$CH_2$—$CONHR^6$, lower alkyl-$Q_r$, cycloalkyl-$Q_r$, lower alkoxy, lower alkenyl, cycloalkenyl-$Q_r$, lower alkynyl, aralkyl-$Q_r$, aryl-$Q_r$, aryloxy, aralkoxy, a heterocyclic ring or a heterocyclyl-$Q_r$, the lower alkyl, cycloalkyl, lower alkoxy, lower alkenyl, cycloalkenyl, lower alkynyl, aralkyl, aryl, aryloxy, aralkoxy and the heterocyclic ring is optionally substituted with at least one group selected from carboxy, amino, nitro, cyano, —$SO_2NR^6$, optionally fluoro substituted lower alkyl, lower alkoxy, hydroxy, halogen, —$CONR^6R^7$, —$CH_2CONR^6R^7$, —$N(R^7)COOR^8$, $R^7CO$—, $R^7OCO$—, $R^7COO$—, —$C(R^7R^9)CO_2R^8$, —$C(R^7R^9)CONR^7R^{10}$, wherein $R^6$ is hydrogen, lower alkyl, cycloalkyl or aryl;

$R^7$ and $R^9$ are independently hydrogen or lower alkyl;

$R^8$ is hydrogen, lower alkyl, lower alkenyl or a carboxylic acid protecting group; and $R^{10}$ is hydrogen, ω-hydroxy-alkyl, phenyl, naphthyl or heterocyclyl, the phenyl, naphthyl or heterocyclyl being unsubstituted or substituted with at least one of the groups of optionally protected hydroxy, halogen, optionally substituted lower alkyl or ω-hydroxyalkyl, optionally substituted lower alkoxy and/or cyano, or $R^7$ and $R^{10}$ form together group of formula

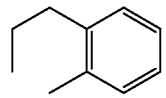

Q is —CHR—, —CO— or —$SO_2$—;

r is 0 or 1;

R is hydrogen or lower alkyl; and $R^3$ is hydroxy or —$O^-$, which process comprises treating a compound having the formula IV

IV

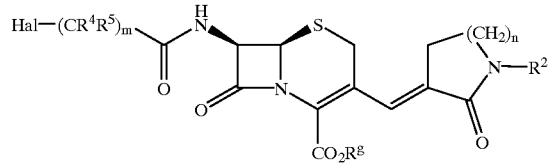

wherein Hal is halogen, with a thiol of the formula $R^1$—SH or a thiolate of the formula $R^1$—$S^-Na^+$ to produce a compound of formula I wherein X is S; with an alcohol of the formula $R^1$—OH or an alcoholate of the formula $R^1$—$O^-Na^+$ to produce a compound of formula I wherein X is O; or with an amine of the formula $R^1$—$NH_2$ to produce a compound of formula I wherein X is NH, thereby producing the compound of general formula I.

This invention also provides an esterification of the product of the process described above, namely a process for producing a compound of the formula

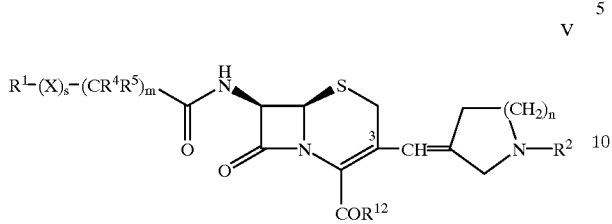

V wherein
- $R^1$ is halogen, lower alkyl, phenyl, benzyl, styryl, naphthyl or heterocyclyl; the lower alkyl, phenyl, benzyl, styryl, naphthyl and heterocyclyl being optionally substituted by at least one of halogen, hydroxy, optionally substituted lower alkyl, optionally substituted lower alkoxy, optionally substituted phenyl, amino, lower alkylamino, di-lower alkylamino, carboxy, lower alkylcarboxy, carbamoyl or lower alkylcarbamoyl;
- $R^4$, $R^5$ independently are hydrogen, lower alkyl or phenyl;
- X is S, O, or NH;
- n is 0, 1 or 2;
- m is 0 or 1;
- s is 0 or 1;
- $R^2$ is hydrogen, hydroxy, —$CH_2$—$CONHR^6$, lower alkyl-$Q_r$, cycloalkyl-$Q_r$, lower alkoxy, lower alkenyl, cycloalkenyl-$Q_r$, lower alkynyl, aralkyl-$Q_r$, aryl-$Q_r$, aryloxy, aralkoxy, a heterocyclic ring or a heterocyclyl-$Q_r$, the lower alkyl, cycloalkyl, lower alkoxy, lower alkenyl, cycloalkenyl, lower alkynyl, aralkyl, aryl, aryloxy, aralkoxy and the heterocyclic ring is optionally substituted with at least one group selected from carboxy, amino, nitro, cyano, —$SO_2NHR^6$, optionally fluoro substituted lower alkyl, lower alkoxy, hydroxy, halogen, —$CONR^6R^7$, —$CH_2CONR^6R^7$, —$N(R^7)COOR^8$, $R^7CO$—, $R^7OCO$—, $R^7COO$—, —$C(R^7R^9)CO_2R^8$, —$C(R^7R^9)CONR^7R^{10}$, wherein
- $R^6$ is hydrogen, lower alkyl, cycloalkyl or aryl;
- $R^7$ and $R^9$ are independently hydrogen or lower alkyl;
- $R^8$ is hydrogen, lower alkyl, lower alkenyl or a carboxylic acid protecting group; and
- $R^{10}$ is hydrogen, ω-hydroxy-alkyl, phenyl, naphthyl or heterocyclyl, the phenyl, naphthyl or heterocyclyl being unsubstituted or substituted with at least one of the groups of optionally protected hydroxy, halogen, optionally substituted lower alkyl or ω-hydroxyalkyl, optionally substituted lower alkoxy and/or cyano, or $R^7$ and $R^{10}$ form together group of formula

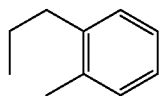

Q is —CHR—, —CO— or —$SO_2$—;
r is 0 or 1;
R is hydrogen or lower alkyl; and
$R^{12}$ is lower alkoxy, which process comprises treating a compound produced by the process of claim 12 with a halide of the formula $R^{12}$—U wherein U is a halogen, thereby producing the compound of formula V.

More particularly the compounds of the formula I in accordance with the invention as well as their pharmaceutical acceptable salts, hydrates, or readily hydrolyzable esters can be manufactured in accordance with the invention by a) treating a compound having the formula II

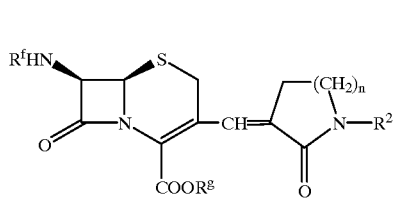

II in which
- $R^2$ and n are defined above;
- $R^f$ is hydrogen or trimethylsilyl; and
- $R^g$ is hydrogen, benzhydryl, p-methoxybenzyl, t-butyl, trimethylsilyl or allyl or salt thereof, with a carboxylic acid of the general formula III

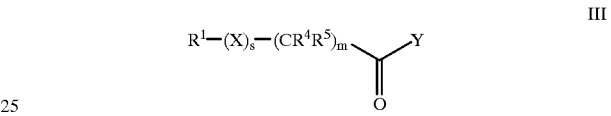

III in which $R^1$, X, s, $R^4$, $R^5$ and m are as defined above and Y is —OH, or a reactive functional derivative thereof wherein Y is, for example a halogen as chloride or bromide, or 1-imidazolyl, 2-mercaptobenzotriazolyl, 1-hydroxbenzotriazolyl or pivaloyloxy, or an activating agent as HBTU (ortho-Benzotriazol-1-yl-N,N,N',N'-tetramethyluronium-hexafluorophosphat), DCC (N,N'-dicylohexylcarbodiimid), CDI (1,1'-carbonyl-diimidazole), CDT (1,1'-carbonyl-1,2,4-ditriazole) or thionylchloride and the like.

for compounds of formula I wherein X is S, O or NH, by treating a compound having the formula IV

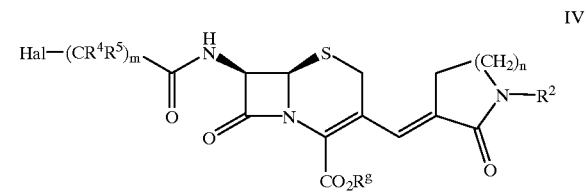

IV wherein $R^4$, $R^5$, m, n, $R^2$ and $R^g$ are as defined above and Hal stands for halogen as bromine or chlorine or iodide preferably bromine, with an appropriate thiol or thiolate or an appropriate alcohol or alcoholate r an appropriate amine in the presence of a base, c) for the manufacture of a readily hydrolysable ester of a compound of formula I subjecting a carboxylic acid of formula I to a corresponding esterification or (d) for the manufacture of salt or hydrates of a compound of formula I or hydrates of said salts converting a compound of formula I into a salt or hydrate or into a hydrate of said salts.

Compounds of formula II may be prepared as described in U.S. Pat. No. 5,523,400 and WO 96126943. Compounds of formula III may be prepared as described in EP 0 727 426 and EP 0 699 681.

The reaction of a compound of formula II prepared according to embodiment (a) with a compound of formula III, or a reactive derivative thereof can be carried out in a manner known per se. The carboxy groups in compounds of formula II (carboxy group in position 2 and/or carboxy groups optionally present in $R^2$) in compounds of formula III (carboxy groups optionally present in $R^1$) can be protected intermediatly or in situ, for example, by esterification to form readily cleavable esters such as a silyl ester (e.g. trimethylsilylester), a p-methoxy-benzylester or benzhydryl ester.

Furthermore the amino groups present in compounds of formula II (in position 7 and/or optionally present in $R^2$) and/or optionally present in $R^1$ of compounds of formula III can be protected, for example, with protecting groups which are cleavable by acid hydrolysis (e.g. the t-butoxycarbonyl or triphenylmethyl groups), by basic hydrolysis (e.g. the trifluoroacetyl group), by hydrazinolysis (e.g. the phthalimido group) or by catalytic cleavage in presence of Pd (the allyloxycarbonyl group). Preferred protecting groups are the t-butyloxy-carbonyl, allyloxycarbonyl, the chloroacetyl, bromoacetyl and iodoacetyl groups, especially the chloroacetyl group. These last-mentioned protecting groups can be cleaved off by treatment with thiourea. Another preferred protecting group is phenylacetyl which can be cleaved off by treatment with $PCl_5$ or enzymatic.

The 7-amino group in compounds II can be protected in situ, for example, by a silyl protecting group such as the trimethylsilyl group.

In reacting a 7-amino compound of formula II with a carboxylic acid of formula III or a reactive functional derivative thereof, for example, a free carboxylic acid can be reacted with an aforementioned ester of a compound of formula II in the presence of a carbodiimide such as dicyclohexylcarbodiimide in an inert solvent such as ethyl acetate, acetonitrile, dioxane, chloroform, methylene chloride, benzene, dimethylformamide or dimethylacetamide, and subsequently the ester group can be cleaved off.

Prepared according to another embodiment, a salt of an acid of formula II (e.g. a trialkylammonium salt such as the triethylammonium salt) is reacted with a reactive functional derivative of a carboxylic acid of formula III in an inert solvent (e.g. dimethylformamide, dimethylacetamide, dimethylsulfoxide and the like).

The reaction of a 7-amino compound of formula II with the carboxylic acid of formula III or a reactive derivative thereof can conveniently be carried out at a temperature between about $-40°$ C. and $+60°$ C., e.g. at room temperature.

Embodiment (b) of the process of the present invention involves treating a compound of formula IV with an appropriate thiol or thiolate or an appropriate alcohol or alcoholate or an appropriate amine in presence of a base, for example, trialkylamine such as trimethylamine, triethylamin sodium bicarbonate, DBU (1,8-diazabicyclo[5,4,0]undec-7-en(1, 5—5) to form the corresponding thioether, ether or amine. Optionally present amino, hydroxy or carboxyl groups can be intermediatly protected with groups as described above.

Deprotection (removal) of protected amino, hydroxy or carboxylic groups present in a compound of formulae II, III and IV can be carried out as follows:

Removal of Amino Protecting Groups

Possible amino-protecting groups are those employed in peptide chemistry, such as the protecting groups mentioned above. Preferably these examples include carbamates, e.g. fluorenylmethyl, 2,2,2-trichloroethyl, t-butyl, triphenylmethyl, allyl, benzyl. Further protecting groups are p-nitro-benzyl, diphenylmethyl, triphenylmethyl, benzyl, formyl, trifluoroacetyl, chloro-acetyl, the cyclic imides of N-phthaloyl, N-trimethylsilyl, N-benzenesulfonyl, N-toluenesulfonyl. Preferred is BOC tt-butoxycarbonyl; other name: (1,1-dimethylethoxy)carbonyl], benzyloxycarbonyl, allyloxy-carbonyl or trimethylsilyl The amino protecting groups may be cleaved off by acid hydrolysis (e.g. the t-butoxycarbonyl or triphenylmethyl group), e.g. aqueous formic acid, trifluoroacetic acid or by basic hydrolysis (e.g. the trifluoroacetyl group). The chloroacetyl, bromoacetyl and iodoacetyl groups are cleaved off by treatment with thiourea. The trimethylsilyl group is cleaved off by hydrolysis or alcoholysis.

Amino-protecting groups which are cleavable by acid hydrolysis are preferably removed with the aid of a lower alkanecarboxylic acid which may be halogenated. In particular, formic acid or trifluoroacetic acid is used. The reaction is carried out in the acid or in the presence of a co-solvent such as a halogenated lower alkane, e.g. methylene chloride. The acid hydrolysis is generally carried out at room temperature, although it can be carried out at a slightly higher or slightly lower temperature (e.g. a temperature in the range of about $-30°$ C. to $+40°$ C.). Protecting groups which are cleavable under basic conditions are generally hydrolyzed with dilute aqueous caustic alkali at $0°$ C. to $30°$ C. The chloroacetyl, bromoacetyl and iodoacetyl protecting groups can be cleaved off using thiourea in acidic, neutral or alkaline medium at about $0°$ C.–$30°$ C. The phthalimido group can be cleaved off with hydrazine at $-20°$ C. to $+50°$ C.

Removal of Hydro Protecting Groups

Possible hydroxy protecting groups are such as are commonly known in the art, such as trimethylsilyl, t-butyl-dimethylsilyl, dimethylphenylsilyl, triphenylmethyl, lower alkanoyl, acetyl, trifluoroacetyl, tetrahydropyranyl, benzyl, p-nitrobenzyl or t-butoxycarbonyl. These groups are removed in the presence of acidic solvents, weak organic acids or weak inorganic bases like sodium bicarbonate, respectively.

Removal of Protecting Groups at the Carboxy Function

As carboxyl protecting groups one may utilize an ester form which can be easily converted into a free carboxyl group under mild conditions, for example, benzhydryl, t-butyl, p-nitrobenzyl, p-methoxybenzyl, allyl, etc.

These protecting groups may be removed as follows:

| | |
|---|---|
| benzhydryl | trifluoroacetic acid with anisol, phenol, cresol or triethylsilane at about $-40°$ C. to room temperature; hydrogen with Pd/C in an alcohol such as ethanol or in tetrahydrofuran; $BF_3$-etherate in acetic acid at about 0 to $50°$ C.; |
| t-butyl | formic acid or trifluoroacetic acid with or without anisol, phenol, cresol or triethylsilane and a solvent such as dichloromethane at about $-10°$ C. to room temperature; |

-continued

| | |
|---|---|
| p-nitrobenzyl | sodium sulfide in acetone/water at about 0 to room temperature; or hydrogen with Pd/C in an alcohol such as ethanol or in tetrahydrofuran; |
| p-methoxybenzyl | formic acid at about 0 to 50° C.; or trifluoroacetic acid and anisol, phenol or triethylsilane at about −40° C. to room temperature; |
| allyl | palladium(O) catalyzed transalkylation reaction in the presence of sodium or potassium salt of 2-ethyl hexanoic acid, see for example J. Org. Chem. 1982, 47, 587. |
| trimethylsilyl | by hydrolysis or alcoholysis at room temperature. |

In order to manufacture a readily hydrolyzable ester of the carboxylic acids of formula I in accordance with embodiment (c) of the process provided by the present invention, a carboxylic acid of formula I is preferably reacted with a corresponding halide, preferably an iodide, containing the desired ester group. The reaction can be accelerated with the aid of a base such as an alkali metal hydroxide, an alkali metal carbonate or an organic amine such as triethylamine. The esterification is preferably carried out in an inert organic solvent such as dimethylacetamide, hexamethylphosphoric acid triamide, dimethyl sulfoxide or, especially, dimethylformamide. The reaction is preferably carried out at a temperature in the range of about 0–40° C.

The manufacture of the salts and hydrates of the compounds of formula I or the hydrates of said salts in accordance with embodiment (d) of the process provided by the present invention can be carried out in a manner known per se; for example, by reacting a carboxylic acid of formula I or a salt thereof with an equivalent amount of the desired base, conveniently in a solvent such as water or an organic solvent (e.g. ethanol, methanol, acetone and the like). Correspondingly, salt formation is brought about by the addition of an organic or inorganic salt or an acid. The temperature at which the salt formation is carried out is not critical. The salt formation is generally carried out at room temperature, but it can be carried out at a temperature slightly above or below room temperature, for example in the range of 0° C. to +50° C.

The manufacture of the hydrates usually takes place automatically in the course of the manufacturing process or as a result of the hygroscopic properties of an initially anhydrous product. For the controlled manufacture of a hydrate, a completely or partially anhydrous carboxylic acid of formula I or salt thereof can be exposed to a moist atmosphere (e.g. at about +10° C. to +40° C.).

Exemplary of the process for obtaining products in accordance with the invention are the following reaction schemes 1 and 2 below.

Scheme 1, Embodiment (a)

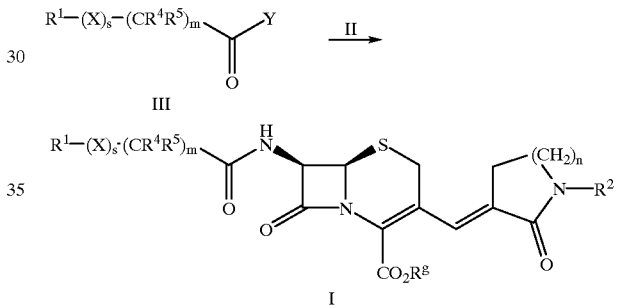

wherein X is —CH$_2$—, O, S or NH and the remaining symbols are as defined above.

Scheme 2, Embodiment (b)

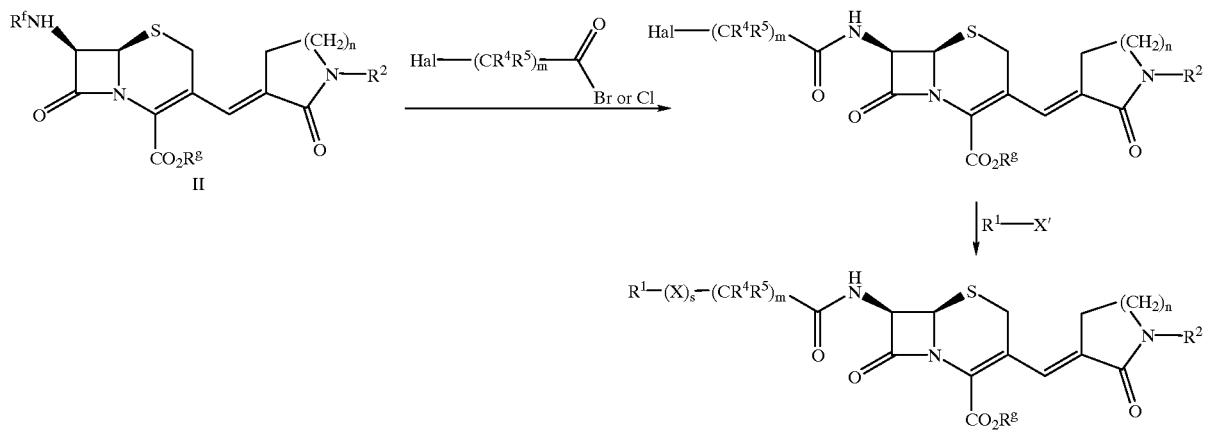

wherein X is O, S, NH and X' accordingly OH or O⁻, SH or S⁻ or $NH_2$ and the remaining substituent are as defined above.

The experimental examples which follow illustrate, but do not limit in any, way, the invention which is defined in the claims which follow thereafter.

EXAMPLES

Method A

Example A1

(E)-(6R,7R)-3-[1-[1-1(4-Hydroxy-phenylcarbamoyl)-methyl]-pyridin-1-ium-4-yl-methyl]-2-oxo-pyrrolidin-3-ylidenemethyl]-8-oxo-7-[2-(2,4,5-trichloro-phenylsulfanyl)-acetylamino]-5-thia-1-aza-bicyclo[4.2.0]oct-2-ene-2-carboxylate To a solution of 68.4 mg (0.25 mmol) (2,4,5-trichloro-phenylsulfanyl)-acetic acid in 3 ml N,N-dimethylacetamide were added under stirring and Argon atmosphere 40.9 mg (0.25 mmol) 1,1'-carbonyldiimidazole. After 30 min, 136.4 mg (0.21 mmol) (E)-(6R,7R)-7-amino-3-[1-[1-[(4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate trifluoroacetate was added in a single portion. After 3 h the reaction mixture was poured on diethyl ether. The solid material was collected by filtration and triturated with ethyl acetate.

Yield: 112.0 mg (67.5%) beige powder; IR(KBr): 1770, 1678, 1642 cm⁻¹; MS(ISP): 790.2 (M⁺).

According to the procedure in example A1 the following additional compounds were prepared:

Example A2

(E)-(6R,7R)-3-[1-[1-[(4-Hydroxy-phenylcarbamoyl)-methyl]-pyridin-1-ium-4-ylmethyl]-2-oxo-pyrrolidin-3-ylidenemethyl]-8-oxo-7-[2-(1-benzothiazol-2-ylsulfanyl)-acetylamino]-5-thia-1-aza-bicyclo[4.2.0]oct-2-ene-2-carboxylate

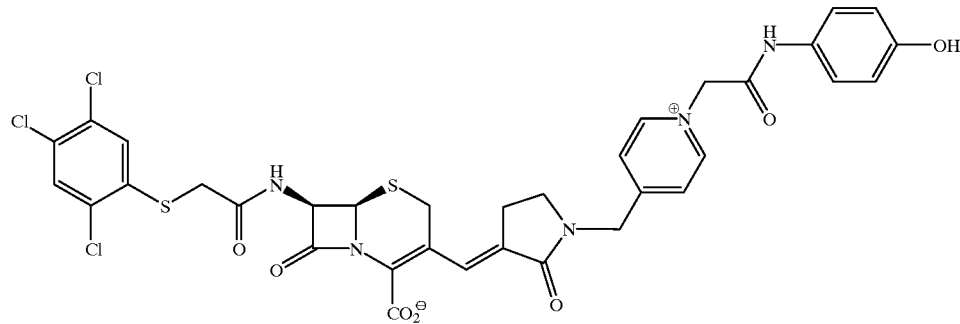

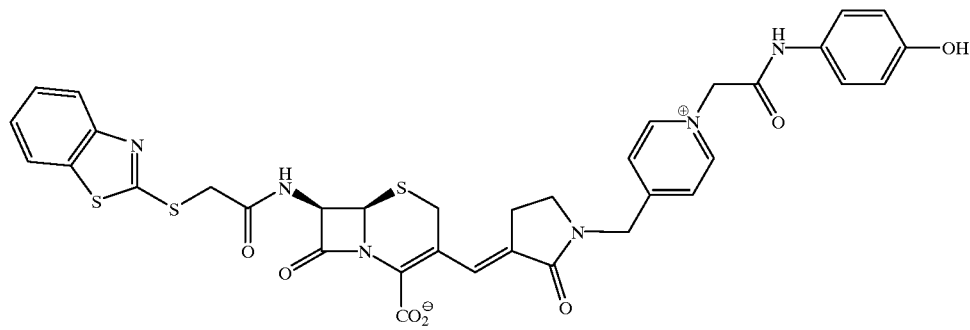

With 70.0 mg (0.43 mmol) 1,1'-carbonyldiimidazole, 96.0 mg (0.43 mmol) (benzothiazol-2-ylsulfanyl)-acetic acid and 233.8 mg (0.36 mmol) (E)-(6R,7R)-7-amino-3-[1-[1-[(4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate trifluoroacetate in 4 ml N,N-dimethylacetamide.

Yield: 92.0 mg (34.4%) yellow powder; IR(KBr): 1769, 1679, 1643, 1625 cm$^{-1}$; MS(ISP): 743.3 (M+H$^+$).

Example A3
(E)-(6R,7R)-3-(1-Cyclopropylmethyl-2-oxo-pyrrolidin-3-ylidenemethyl)-8-oxo-7-[2-(2,4,5-trichloro-phenylsulfanyl)-acetylaminol-5-thia-1-aza-bicyclo[4.2.0]oct-2-ene-2-carboxylic acid

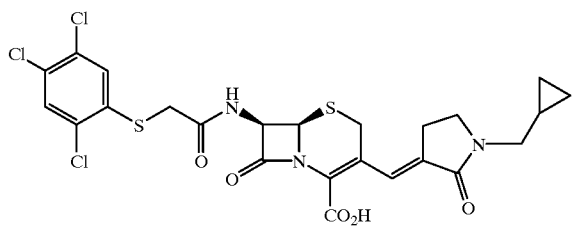

With 180.0 mg (1.11 mmol) 1,1'-carbonyldiimidazole, 301.4 mg (1.11 mmol) 2,4,5-trichloro-phenylsulfanyl)-acetic acid and 323.2 mg (0.92 mmol) (E)-6R,7R)-7-amino-3-(1-cyclopropylmethyl-2-oxo-pyrrolidin-3-ylidenemethyl)-8-oxo-5-thia-1-azabicyclo[4.2.0]oct-2-ene-2-carboxylic acid in 8 ml N,N-dimethylformamide.

Yield: 337.0 mg (60.4%) brown powder; IR(KBr): 1773, 1668, 1621 cm$^{31\ 1}$; MS(ISP): 602.2 (M+H$^+$);

Example A4
(E)-(6R,7R)-7-[2-(Benzothiazol-2-ylsulfanyl)-acetylamino]-3-(1-cyclopropylmethyl-2-oxo-pyrrolidin-3-ylidenemethyl)-8-oxo-5-thia-1-aza-bicyclo[4.2.0]oct-2-ene-2-carboxylic acid

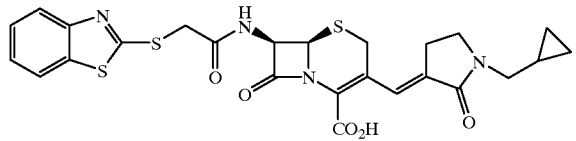

With 220.0 mg (1.35 mmol) 1,1'-carbonyldiimidazole, 304.1 mg (1.35 mmol) (benzothiazol-2-ylsulfanyl)-acetic acid and 394.8 mg (1.13 mmol) (E)-(6R,7R)-7-amino-3-(1-cyclopropylmethyl-2-oxo-pyrrolidin-3-ylidenemethyl)-8-oxo-5-thia-1-azabicyclo[4.2.0]oct-2-ene-2-carboxylic acid in 7 ml N,N-dimethylformamide.

Yield: 173.0 mg (27.5%) orange powder; IR(KBr): 1772, 1665, 1623 cm$_{-1}$; MS(ISP): 557.1 (M+H$^+$);

Example A5
(E)-(6R,7R)-3-(1-Cyclopropylmethyl-2-oxo-pyrrolidin-3-ylidenemethyl)-8-oxo-7-(2-phenylsulfanyl-acetylamino)-5-thia-1-aza-bicyclo[4.2.0]oct-2-ene-2-carboxylic acid

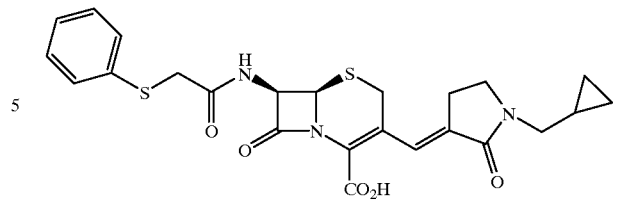

With 167.0 mg (1.03 mmol) 1,1'-carbonyldiimidazole, 173.0 mg (1.03 mmol) 2-(phenylthio)acetic acid and 300.0 mg (0.86 mmol) (E)-(6R,7R)-7-amino-3-(1-cyclopropylmethyl-2-oxo-pyrrolidin-3-ylidenemethyl)-8-oxo-5-thia-l-azabicyclo[4.2.0]oct-2-ene-2-carboxylic acid in 6 ml N,N-dimethylformamide.

Yield: 271.5 mg (63.1%) brown powder; IR(KBr): 1773, 1662, 1624 cm$^{-1}$; MS(ISP): 500.3 (M+H$^+$).

Example A6
(E)-(6R,7R)-3-(1-Cyclopropylmethyl-2-oxo-pyrrolidin-3-ylidenemethyl)-8-oxo-7-(2-pyridin-4-ylsulfanyl-acetylamino)-5-thia-1-aza-bicyclo[4.2.0]oct-2-ene-2-carboxylic acid

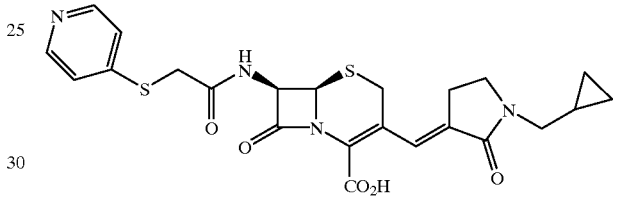

With 111.0 mg (0.68 mmol) 1,1'-carbonyldiimidazole, 116.0 mg (0.68 mmol) (pyridin-4-ylsulfanyl)-acetic acid and 200.0 mg (0.57 mmol) ) (E)-(6R,7R)-7-amino-3-(1-cyclopropylmethyl-2-oxo-pyrrolidin-3-ylidenemethyl)-8-oxo-5-thia-1-azabicyclo[4.2.0]oct-2-ene-2-carboxylic acid in 4 ml N,N-dimethylformamide.

Yield: 79.0 mg (27.5%) beige solid; IR(KBr): 1769, 1667, 1624; MS(ISP): 501.1 (M+H$^+$).

Example A7
(E)-(6R,7R)-3-(1-Cyclopropylmethyl-2-oxo-pyrrolidin-3-ylidenemethyl)-7-[2-(naphthalen-2-ylsulfanyl)-acetylamino]-8-oxo-5-thia-1-aza-bicyclo[4.2.0]oct-2-ene-2-carboxylic acid

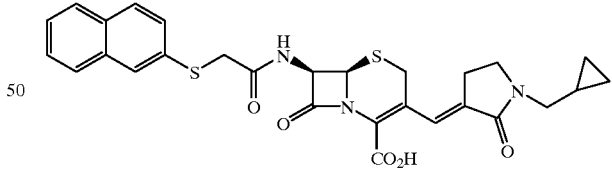

With 167.0 mg (1.03 mmol) 1,1'-carbonyldiimidazole, 225.0 mg (1.03 mmol (naphthalen-2-ylsulfanyl)-acetic acid and 300.0 mg (0.86 mmol) (E)-(6R,7R)-7-amino-3-(1-cyclopropylmethyl-2-oxo-pyrrolidin-3-ylidenemethyl)-8-oxo-5-thia-1-azabicyclo[4.2.0]oct-2-ene-2-carboxylic acid in 4 ml N,N-dimethylformamide.

Yield: 320.0 mg (62%) brown powder; IR(KBr): 1769, 1662, 1623 cm$^{-1}$; MS(ISP): 550.2 (M+H$^+$).

Example A8
(E)-(6R,7R)-7-[2-(2-Amino-thiazol-4-yl)-acetylamino]-3-[1-[1-[(4-hydroxyphenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate

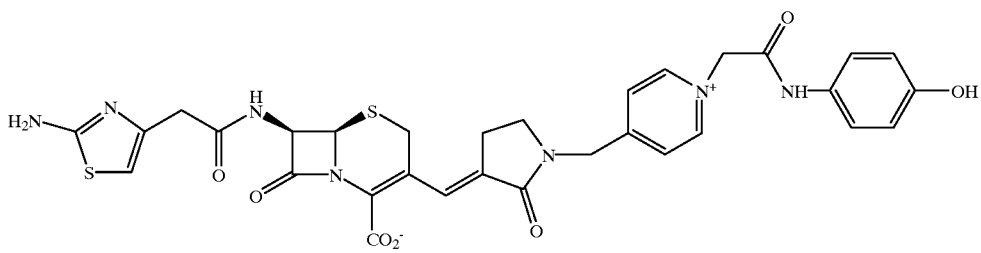

With 54.5 mg (0.34 mmol) 1,1'-carbonyldiimidazole, 53.0 mg (0.34 mmol) (2-aminothiazole-4-yl)-acetic acid and 182.0 mg (0.28 mmol) (E)-(6R,7R)-7-amino-3-[1-[1-[(4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate trifluoroacetate in 4 ml N,N-dimethylformamide. The resulting solid was purified by reversed phase chromatography (RP-18 LiChro-Prep gel, water:acetonitrile=9:1). The organic solvent was stripped off at a rotary evaporator and the aqueous phase was freeze-dried.

Yield: 49.0 mg (24.7%) beige lyophilisate; IR(KBr): 1775, 1680, 1650 cm$^{-1}$; MS(ISP): 676.2 (M$^+$).

Prep gel, water:acetonitrile=9:1). The organic solvent was stripped off at a rotary evaporator and the aqueous phase was freeze-dried.

Yield: 120.0 mg (28.6%) beige lyophilisate; IR(KBr): 1769, 1664, 1620 cm$^{-1}$; MS(ISP): 490.2 (M+H$^+$).

Example A10

(E)-(6R,7R)-3-[1-[1-[(4-Hydroxy-phenylcarbamoyl)-methyl]-pyridin-1-ium-4-ylmethyl]-2-oxo-pyrrolidin-3-ylidenemethyl]-8-oxo-7-[2-(pyridin-4-ylsulfanyl)-acetylamino]-5-thia-1-aza-bicyclo[4.2.0]oct-2-ene-2-carboxylate

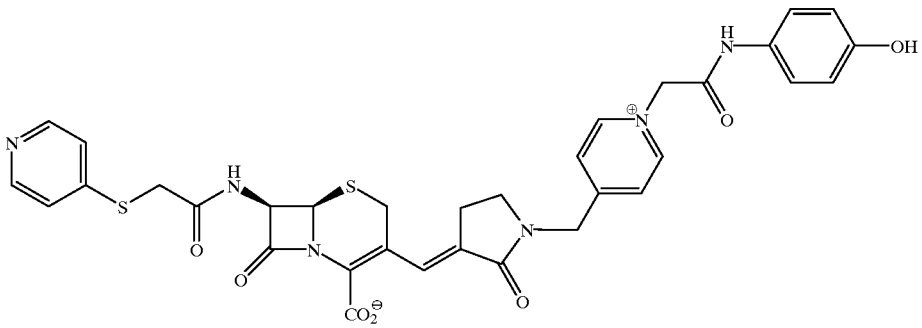

Example A9

(E)-(6R,7R)-7-[2-(2-Amino-thiazol-4-yl)-acetylamino]-3-(1-cyclopropylmethyl-2-oxo-pyrrolidin-3-ylidenemethyl)-8-oxo-5-thia-1-aza-bicyclo[4.2.0]oct-2-ene-2-carboxylic acid

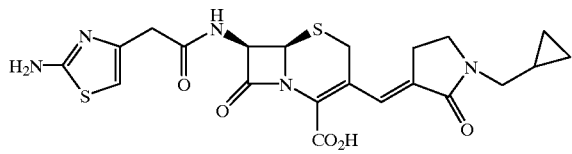

With 167.0 mg (1.03 mmol) 1,1'-carbonyldiimidazole, 163.0 mg (1.03 mmol) (2-aminothiazole-4-yl)-acetic acid and 300.0 mg (0.86 mmol) (E)-(6R,7R)-7-amino-3-(1-cyclopropylmethyl-2-oxo-pyrrolidin-3-ylidenemethyl)-8-oxo-5-thia-1-azabicyclo[4.2.0]oct-2-ene-2-carboxylic acid in 6 ml N,N-dimethylformamide. The resulting solid was purified by reversed phase chromatography (RP-18 LiChro- With 70.0 mg (0.43 mmol) 1,1'-carbonyldiimidazole, 72.8 mg (0.43 mmol) (pyridin-4-ylsulfanyl)-acetic acid and 232.8 mg (0.36 mmol) (E)-(6R,7R)-7-amino-3-[1-[1-[(4-hydroxy-phenylcarbamoyl)-methyl]-pyridin- 1-ium-4-ylmethyl]-2-oxo-pyrrolidin-3 -ylidenemethyl]-8-oxo-5-thia-1-aza-bicyclo [4.2.0]oct-2-ene-2-carboxylate trifluoroacetate in 4 ml ml N,N-dimethylacetamide. The brown solid was purified by column chromatography on MCI gel (75–150μ, Mitsubishi Kasei Corporation) with a gradient of water:acetonitrile (1:0, 4:1, 3:1, 2:1, 1:1). The organic solvent was stripped off at a rotary evaporator and the aqueous phase was freeze-dried.

Yield: 58.0 mg (30.0%) beige lyophilisate; IR(KBr): 1772, 1670, 1625 cm$^{-1}$; MS(ISP): 687.3 (M+H$^+$).

Example A1

(E)-(6R,7R)-3-[1-[1-[(4-Hydroxy-phenylcarbamoyl)-methyl]-pyridin-1-ium-4-ylmethyl]-2-oxo-pyrrolidin-3-ylidenemethyl]-8-oxo-7-(2-phenylsulfanylacetylamino)-5-thia-1-aza-bicyclo[4.2.0]oct-2-ene-2-carboxylate

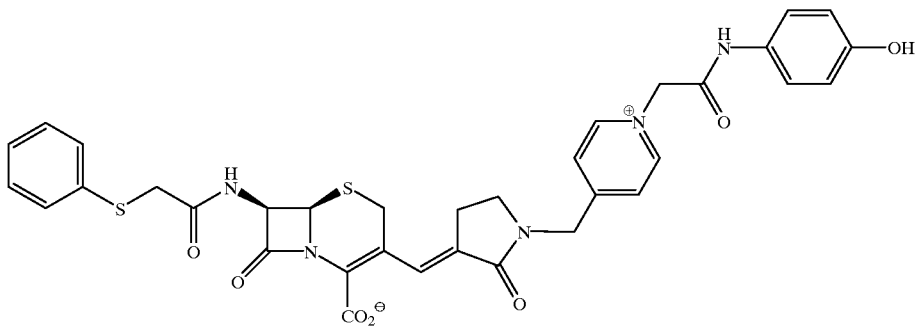

With 70.0 mg (0.43 mmol) 1,1'-carbonyldiimidazole, 71.0 mg (0.43 mmol) 2-(phenylthio)acetic acid and 188.4 mg (0.29 mmol) (E)-(6R,7R)-7-amino-3-[1-[1-[(4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate trifluoroacetate in 4 ml ml N,N-dimethylacetamide. The resulting solid was suspended in 6 ml water:acetonitrile (1:1) and HCl was added until all compound dissolved. After column chromatography on MCI gel (75–150μ, Mitsubishi Kasei Corporation) with a gradient of water:acetonitril (1:0, 4:1, 3:1, 2:1, 1:1) the organic solvent was stripped off at a rotary evaporator and the aqueous phase was freeze-dried.

Yield: 105.6 mg (64.4%) beige lyophilisate; IR(KBr): 1770, 1680, 1643 cm$^{-1}$; MS(ISP): 686.3 (M+H$^+$).

Example A12

(E)-(6R,7R)-3-[1-1l-[(3-Fluoro-4-hydroxy-phenylcarbamoyl)-methyl]-pyridin-1-ium-4-ylmethyl]-2-oxo-pyrrolidin-3-ylidenemethyl]-7-[2-(naphthalen-2-yl-sulfanyl)-acetylamino]-8-oxo-5-thia-1-aza-bicyclo[4.2.0]oct-2-ene-2-carboxylate 200.0 mg (0.30 mmol) (E)-(6R,7R)-7-amino-3-[1-[1-[(3-fluoro-4-hydroxy-phenylcarbamoyl)-methyl]- pyridin-1-ium-4-ylmethyl]-2-oxo-pyrrolidin-3-ylidenemethyl]-8-oxo-5-thia-1-aza-bicyclo[4.2.0]oct-2-ene-2-carboxylate trifluoroacetate in 4 ml N,N-dimethylacetamide. The resulting solid was purified by column chromatography on MCI gel (75–150μ, Mitsubishi Kasei Corporation) with a gradient of water:acetonitrile (1:0, 4:1, 3:1, 2:1, 1:1). The organic solvent was stripped off at a rotary evaporator and the aqueous phase was freeze-dried.

Yield: 55.0 mg (24.0%) beige lyophilisate; IR(KBr): 1770, 1680, 1650, 1628 cm$^{-1}$; MS(ISP): 754.3 (M+H$^+$).

Example A13

(E)-(6R,7R)-7-[2-(3,4-Dichloro-phenylsulfanyl)-acetylamino]-3-[1-[1-[(3-fluoro-4-hydroxy-phenylcarbamoyl)-methyl]-pyridin-1-ium-4-ylmethyl]-2-

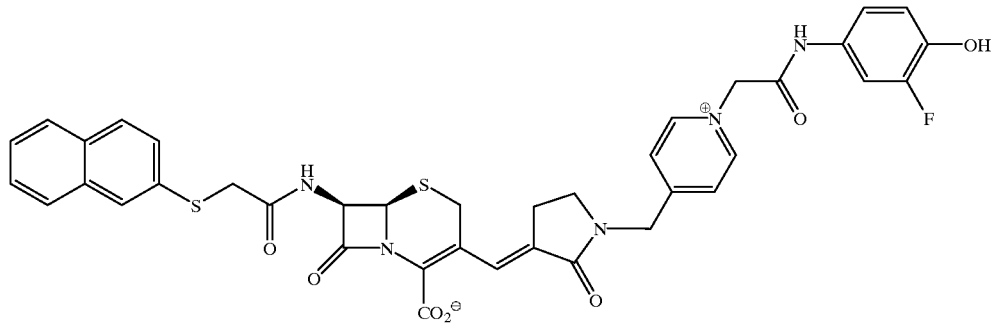

With 58.3 mg (0.36 mmol) 1,1'-carbonyldiimidazole, 78.5 mg (0.36 mmol) (naphthalen-2-ylsulfanyl)-acetic acid and oxo-pyrrolidin-3-ylidenemethyl]-8-oxo-5-thia-1-aza-bicyclo[4.2.0]oct-2-ene-2-carboxylate

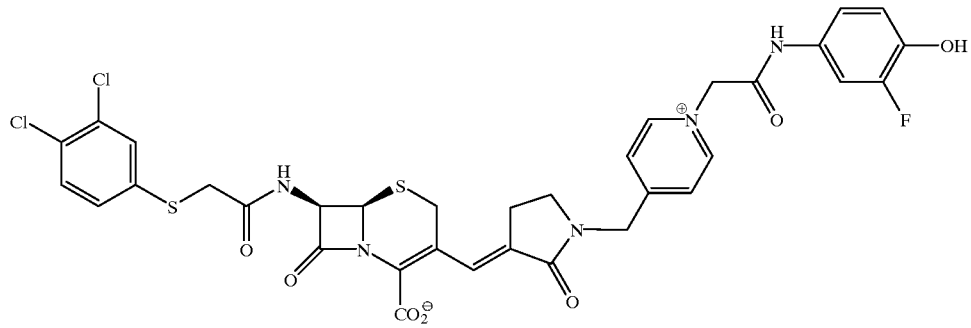

With 60.0 mg (0.36 mmol) 1,1'-carbonyldiimidazole, 85.0 mg (0.36 mmol) [(3,4-dichlorophenyl)thio]acetic acid and 200.0 mg (0.30 mmol) (E)-(6R,7R)-7-amino-3-[1-[1-[(3-fluoro-4-hydroxy-phenylcarbamoyl)-methyl]-pyridin-1-ium-4-ylmethyl]- 2-oxo-pyrrolidin-3-ylidenemethyl]-8-oxo-5-thia-1-aza-bicyclo[4.2 .0]oct-2-ene-2-carboxylate trifluoroacetate in 4 ml N,N-dimethylacetamide. The resulting solid was purified by column chromatography on MCI gel (75–150μ, Mitsubishi Kasei Corporation) with a gradient of water: acetonitrile (1:0, 4:1, 3:1, 2:1, 1:1). The organic solvent was stripped off at a rotary evaporator and the aqueous phase was freeze-dried.

Yield: 70.0 mg (30.2%) beige lyophilisate; IR(KBr): 1772, 1680, 1642, 1617 cm$^{-1}$; MS(ISP): 772.3 (M+H$^+$).

Example A14
(E)-(6R,7R)-3-[1-(3-Hydroxy-benzyl)-2-oxo-pyrrolidin-3-ylidenemethyl]-8-oxo-7-[2-(2,4,5-trichloro-phenylsulfanyl)-acetylamino]-5-thia-1-aza-bicyclo[4.2.0]oct-2-ere-2-carboxylic acid

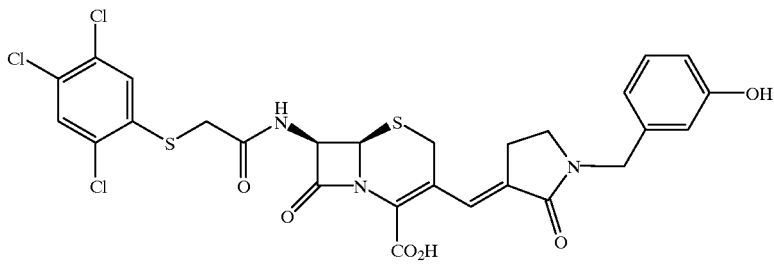

With 146.0 mg (0.90 mmol) 1,1'-carbonyldiimidazole, 244.4 mg (0.90 mmol) (2,4,5-trichloro-phenylsulfanyl)-acetic acid and 301.0 mg (0.73 mmol) (E)-(6R,7R)-7-amino-3-[1-(3-hydroxy-benzyl)-2-oxo-pyrrolidin-3-ylidenemethyl]-8-oxo-5-thia-1-aza-bicyclo[4.2.0]oct-2-ene-2-carboxylic acid trifluoroacetate in 5 ml N,N-dimethylacetamide.

Yield: 180.0 mg (37.7%) beige powder; IR(KBr): 1767, 1664, 1614 cm$^{-1}$; MS(ISP): 654.1 (M+H$^+$).

Example A15

(E)-(6R,7S)-3-[1-(3-Hydroxy-benzyl)-2-oxo-pyrrolidin-3-ylidenemethyl]-8-oxo-7-[2-naphthalen-2-ylsulfanyl)-acetylamino]-5-thia-1-aza-bicyclo[4.2.0]oct-2-ene-2-carboxylic acid

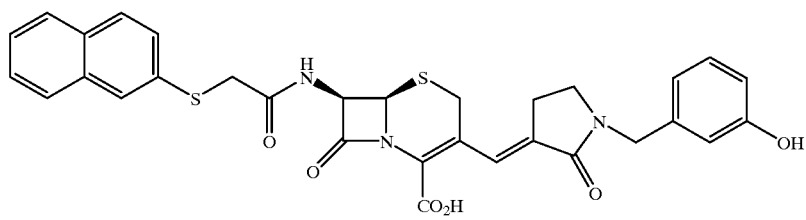

With 146.0 mg (0.90 mmol) 1,1'-carbonyldiimidazole, 196.5 mg (0.90 mmol) (naphthalen-2-ylsulfanyl)-acetic acid and 301.0 mg (0.73 mmol) (E)-(6R,7R)-7-amino-3-[1-(3-hydroxy-benzyl)-2-oxo-pyrrolidin-3-ylidenemethyl]-8-oxo-5-thia-1-aza-bicyclo[4.2.0]oct-2-ene-2-carboxylic acid trifluoroacetate in 5 ml N,N-dimethylacetamide. The resulting solid was purified by column chromatography on MCI gel (75–150μ, Mitsubishi Kasei Corporation) with a gradient of water: acetonitrile (1:0, 4:1, 3:1, 2:1, 1:1). The organic solvent was stripped off at a rotary evaporator and the aqueous phase was freeze-dried.

Yield: 65.0 mg (14.6%) beige lyophilisate; IR(KBr): 1771, 1663, 1589 cm$^{-1}$; MS(ISP): 602.2 (M+H$^+$).

Example A16

Mixture of (E)-(6R,7R)-8-oxo-3-[(R)- and -[(S)-2-oxo-[1,3']bipyrrolidinyl-3-ylidenemethyl]-8-oxo-7-[2-(2,4,5-trichloro-phenylsulfanyl)-acetylamino]-5-thia-1-aza-bicyclo[4.2.0]oct-2-ene-2-carboxylic acid hydrochloride

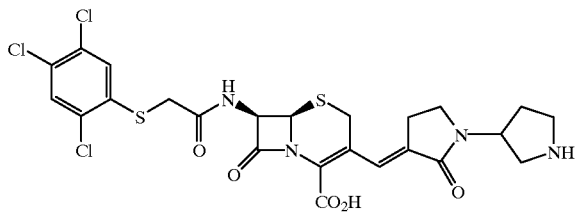

Step a: Mixture of (E)-(6R,7R)-3-[(R)- and -[(S)-1'-allyloxycarbonyl-2-oxo-[1,3']-bipyrrolidinyl-3-ylidenemethyl]-8-oxo-7-[2-(2,4,5-trichloro-phenylsulfanyl)-acetacetylamino]-5-thia-1-aza-bicyclo[4.2.0]oct-2-ene-2-carboxylic acid With 115.2 mg (0.71 mmol) 1,1'-carbonyldiimidazole, 193.4 mg (0.71 mmol) (2,4,5-trichloro-phenylsulfanyl)-acetic acid and 329.1 mg (0.59 mmol) of a mixture of (E)-(6R,7R)-3-[(R)- and -[(S)-1'-allyloxycarbonyl-2-oxo-[1,3']bipyrrolidin-3-ylidenemethyl]-7-amino-8-oxo-5-thia-1-aza-bicyclo[4.2.0]oct-2-ene-2-carboxylic acid trifluoroacetate in 6 ml N,N-dimethylacetamide Prepared according to example A1.

Yield: 220.0 mg (66.0%) beige powder IR(KBr): 1774, 1678, 1624 cm$^{-1}$; MS(ISP): 703.2 (M+H$^+$).

Step b: Mixture of (E)-(6R,7R)-8oxo-3-[(R)- and -[(S)-2-oxo-[1,3']bipyrrolidinyl-3-ylidenemethyl]-8-oxo-7-[2-(2,4,5-trichloro-phenylsulfanyl)-acetylamino]-5-thia-1-aza-bicyclo[4.2.0]oct-2-ene-2-carboxylic acid hydrochloride The product prepared in step a (220.0 mg, 0.31 mmol) was suspended in 12 ml dichloromethane and 124 μl (0.50 mmol) N,O-bis-(trimethylsilyl)-acetamide was added. After a clear solution had formed, 5.60 mg (8.56 mol) palladium-bis-(triphenylphosphine)-dichloride, 0.36 ml (6.30 mmol) acetic acid and 0.8 ml (3.0 mmol) tributyltinhydride were added. After 45 min 40 μl water was added to the suspension and the reaction mixture was poured under stirring on 200 ml diethyl ether, containing 2 ml of a hydrochloric acid-saturated diethyl ether solution. The solid was collected by filtration and triturated with 40 ml ethyl acetate.

Yield: 180.0 mg (87.8%) beige powder; IR(KBr): 1771, 1661, 1582 cm$^{-1}$; MS(ISP): 619.1 (M+H$^+$).

Example A17

(E)-(6R,7R)-3-[1-[1-[(3-Fluoro-4-hydroxy-phenylcarbamoyl)-methyl]-pyridin-1-ium-4-ylmethyl]-2-oxo-pyrrolidin-3-ylidenemethyl]-8-oxo-7-(2-phenylsulfanyl-acetylamino)-5-thia-1-aza-bicyclo[4.2.0]oct-2-ene-2-carboxylate

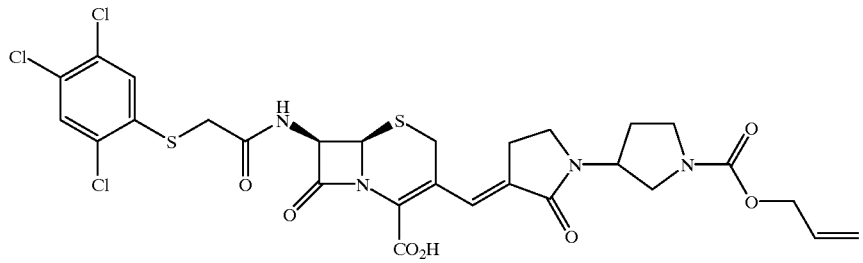

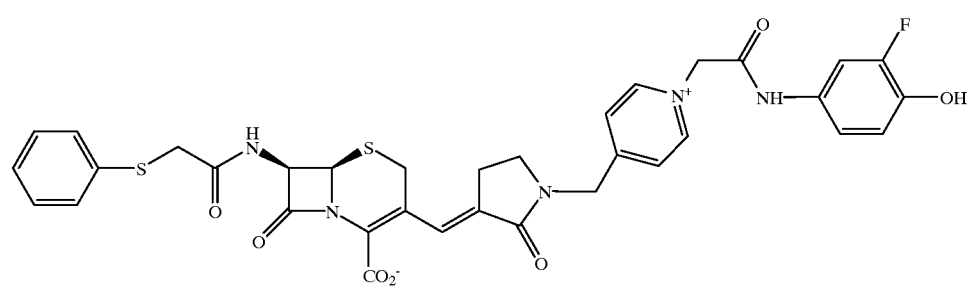

With 175.0 mg (1.08 mmol) 1,1'-carbonyldiimidazole, 182.0 mg (1.08 mmol) 2-(phenylthio)acetic acid and 500.0 mg (0.75 mmol) (E)-(6R,7R)-7-amino-3-[1-[1-[(3-fluoro-4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate trifluoroacetate in 4 ml N,N-dimethylacetamide. The resulting solid was purified by column chromatography on MCI gel (75–150µ, Mitsubishi Kasei Corporation) with a gradient of water:acetonitrile (1:0, 4:1, 3:1, 2:1). The organic solvent was stripped off at a rotary evaporator and the aqueous phase was freeze-dried.

Yield: 90.0 mg (20.6%) beige lyophilisate; IR(KBr): 1772, 1680, 1648 cm$^{-1}$; MS(ISP): 704.4 (M $^+$).

Example A18

(E)-(6R,7R)-3-[1-[1-[(3-Fluoro-4-hydroxy-phenylcarbamoyl)-methyl]-pyridin-1-ium-4-ylmethyl]-2-oxo-pyrrolidin-3-ylidenemethyl]-8-oxo-7-[2-(4-trifluoromethyl-phenylsulfanyl)-acetylamino)-5-thia-1-aza-bicyclo[4.2.0]oct-2-ene-2-carboxylate

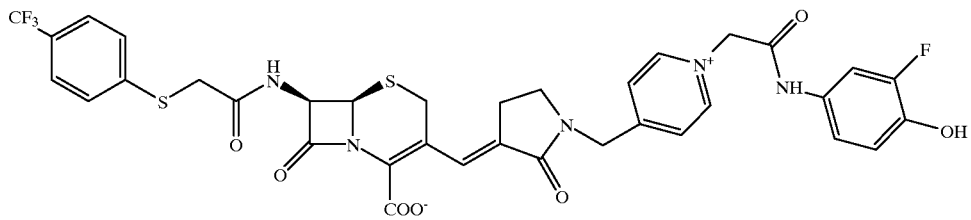

With 66.8 mg (0.41 mmol) 1,1,-carbonyldiimidazole, 97.3 mg (0.41 mmol) 2-[4-(trifluoromethyl) phenylthiolacetic acid and 250.0 mg (0.37 mmol) (E)-(6R,7R)-7-amino-3-[1-[1-[(3-fluoro-4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate trifluoroacetate in 4 ml N,N-dimethylacetamide. The resulting solid was purified by column chromatography on MCI gel (75–150µ, Mitsubishi Kasei Corporation) with a gradient of water:acetonitrile (1:0, 4:1, 3:1, 2:1, 1:1). The organic solvent was stripped off at a rotary evaporator and the aqueous phase was freeze-dried.

Yield: 89.0 mg (30.8%) pale yellow lyophilisate; IR(KBr): 1777, 1678, 1650 cm$^{-1}$; MS(ISP): 772.3 (M+H$^+$).

Example A19

(E)-(6R,7R)-7-[2-(2,5-Dichloro-phenylsulfanyl)-acetylaminol-3-[1-[(3-fluoro-4-hydroxy-phenylcarbamoyl)-methyl]-pyridin-1-ium-4-ylmethyl-2-oxo-pyrrolidin-3-ylidenemethyl]-8-oxo-5-thia-1-aza-bicyclo[4.2.0]oct-2-ene-2-carboxylate

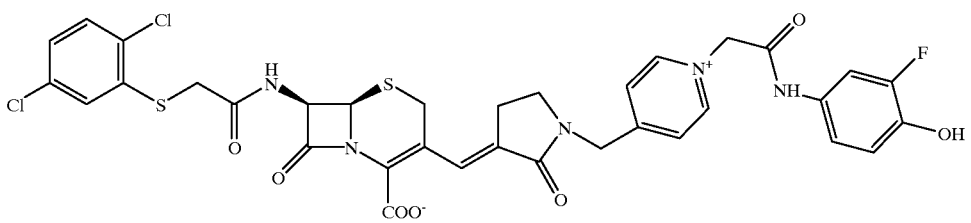

With 72.9 mg (0.45 mmol) 1,1,-carbonyldiimidazole, 106.5 mg (0.45 mmol) (2,5-dichloro-phenylsulfanyl)acetic acid and 250.0 mg (0.37 mmol) (E)-(6R,7R)-7-amino-3-[1-[1-[(3-fluoro-4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate trifluoroacetate in 4 ml N,N-dimethylacetamide. The resulting solid was purified by column chromatography on MCI gel (75–150µ, Mitsubishi Kasei Corporation) with a gradient of water:acetonitrile (1:0, 4:1, 3:1, 2:1, 1:1). The organic solvent was stripped off at a rotary evaporator and the aqueous phase was freeze-dried.

Yield: 74.5 mg (21.3%) beige lyophilisate; IR(KBr): 1772, 1680, 1650 cm$^{-1}$; MS(ISP): 772.3 (M+H $^+$).

Example A20

(E)-(6R,7R)-3–11-(3-Hydroxy-benzyl)-2-oxo-pyrrolidin-3-ylidenemethyl]-8-oxo-7-(2-phenylsulfanyl-acetylamino)-5-thia-1-aza-bicyclo[4.2.0]oct-2-ene-2-carboxylic acid

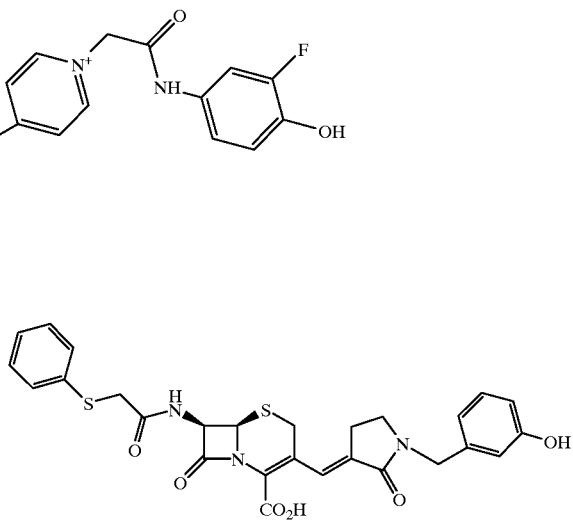

With 121.1 mg (0.75 mmol) 1,1,-carbonyldiimidazole, 125.6 mg (0.75 mmol) (phenylthio)acetic acid and 250.0 mg (0.62 mmol) (E)-(6R,7R)-7-amino-3-[1-(3-hydroxy-benzyl)-2-oxo-pyrrolidin-3-ylidenemethyl]-8-oxo-5-thia-1-aza-bicyclo-[4.2.0]oct-2-ene-2-carboxylic acid trifluoroacetate in 4 ml N,N-dimethyl-acetamide. The resulting solid was purified by column chromatography on MCI gel (75–150µ, Mitsubishi Kasei Corporation) with a gradient of water:acetonitrile (1:0, 4:1, 3:1). The organic solvent was stripped off at a rotary evaporator and the aqueous phase was freeze-dried.

Yield: 189.5 mg (55.2%) yellow lyophilisate; IR(KBr): 1764,1664,1612 cm$^{-1}$; MS(ISP): 552.2 (M+H$^+$).

Example A21

(E)-(6R,7R)-7-[2-(3,4-Dimethoxy-phenylsulfanyl)-acetylamino]-3-[1-(3-hydroxy-benzyl)-2-oxo-pyrrolidin-3-ylidenemethyl]-8-oxo-5-thia-1-aza-bicyclo[4.2.0]oct-2-ene-2-carboxylic acid

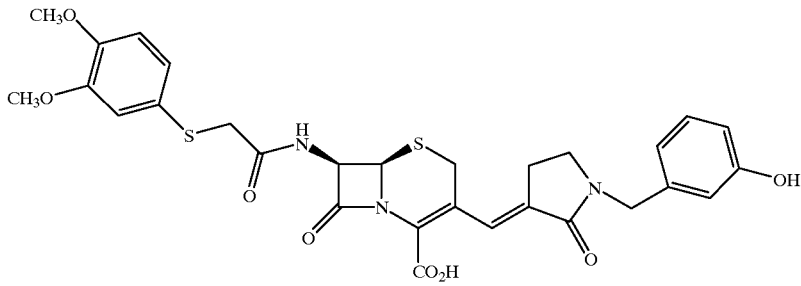

With 121.1 mg (0.75 mmol) 1,1,-carbonyldiimidazole, 170.6 mg (0.75 mmol) 2-(3,4-dimethoxyphenylthio)acetic acid and 250.0 mg (0.62 mmol) (E)-(6R,7R)-7-amino-3-[1-(3-hydroxy-benzyl)-2-oxo-pyrrolidin-3-ylidenemethyl]-8-oxo-5-thia- 1-aza-bicyclo[4.2.0]oct-2-ene2-carboxylic acid trifluoroacetate in 4 ml N,N-dimethylacetamide. The resulting solid was purified by column chromatography on MCI gel (75–150μ, Mitsubishi Kasei Corporation) with a gradient of water:acetonitrile (1:0, 4:1, 3:1). The organic solvent was stripped off at a rotary evaporator and the aqueous phase was freeze-dried.

Yield: 175.6 mg (46.1%) pale yellow lyophilisate; IR(KBr): 1766, 1664, 1588 cm$^{-1}$; MS(ISP): 612.2 (M+H $^+$).

Example A22

(E)-(6R,7R)-3-[1-[1-[(3-Fluoro-4-hydroxy-phenylcarbamoyl)-methyl]-pyridin-1-ium-4-ylmethyl]-2-oxo-pyrrolidin-3-ylidenemethyl]-8-oxo-7- [2-(2,4,5-trichlorophenylsulfanyl)-acetylamino]-5-thia-1-aza-bicyclo[4.2.0]oct-2-ene-2-carboxylate

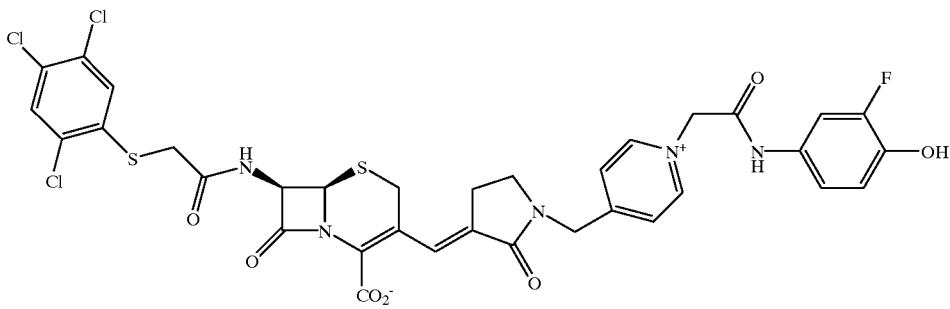

With 60.0 mg (0.36 mmol) 1,1,-carbonyldiimidazole, 99.0 mg (0.36 mmol) (2,4,5-trichloro-phenylsulfanyl)-acetic acid and 200.0 mg (0.30 mmol) (E)-(6R,7R)-7-amino-3 -[1-[1-[(3-fluoro-4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate trifluoroacetate in 4 ml N,N-dimethylacetamide. The resulting solid was purified by column chromatography on MCI gel (75–150μ, Mitsubishi Kasei Corporation) with a gradient of water: acetonitril (2:1, 1:1). The organic solvent was stripped off at a rotary evaporator and the aqueous phase was freeze-dried.

Yield: 140.0 mg (57.8%) beige lyophilisate; IR(KBr): 1763, 1666, 1645 cm$^{-1}$; MS(ISP): 806.3,808.3 (M+H)$^+$.

The following compounds were prepared according to Example A1

Example A23

(E)-(6R,7R)-7-[2-(Benzothiazol-2-ylsulfanyl)-acetylamino]-3-[1-(4-hydroxybenzyl)-2-oxo-pyrrolidin-3-ylidenemethyl]-8-oxo-5-thia-1-aza-bicyclo[4.2.0]oct-2-ene-2-carboxylic acid imidazole salt (1:1)

Yield: 66.0% beige solid; MS(ISP): 609.4 (M+H)$^+$; IR(KBr): 1772, 1669, 1613 cm$^{-1}$.

Example A24

(E)-(6R,7R)-3-[1-(1H-Benzoimidazol-2-ylmethyl)-2-oxo-pyrrolidin-3-ylidenemethyl]-8-oxo-7-(phenylsulfanylcarbonylmethyl-amino)-5-thia- 1-aza-bicyclo[4.2.0]oct-2-ene-2-carboxylic acid imidazol salt (1:1)

Yield: 91.6% brown solid; MS(ISP): 576.1 (M+H)$^+$; IR(KBr): 1770, 1673, 1625 cm$^{-1}$.

Example A25

(E)-(6R,7R)-3-(1-Cyclopropyl-2-oxo-pyrrolidin-3-ylidenemethyl)-7-[2-(naphthalen-1-ylsulfanyl)-acetylamino]-8-oxo-5-thia-1-aza-bicyclo[4.2.0]oct-2-ene-2-carboxylic acid imidazole salt (1:1)

Yield: 41.6% beige solid; MS(ISP): 536.3 (M+H)$^+$; IR(KBr): 1769, 1664, 1624 cm$^{-1}$.

Example A26

(E)-(6R,7R)-3-[1-(4-Hydroxy-benzyl)-2-oxo-pyrrolidin-3-ylidenemethy]-7-[2-(naphthalen-2-ylsulfanyl)-acetylamino]-8-oxo-5-thia-1-aza-bicyclo[4.2.0]oct-2-ene-2-carboxylic acid imidazole salt (1:1)

Yield: 67.7% beige solid; MS(ISP): 602.2 (M+H)$^+$; IR(KBr): 1771, 1667, 1614 cm$^{-1}$;

Example A27
(E)-(6R,7R)-7-[2-(Benzothiazol-2-ylsulfanyl)-acetylamino]-3-(1-cyclopropyl-2-oxo-pyrrolidin-3-ylidenemethyl)-8-oxo-5-thia-1-aza-bicyclo[4.2.0]oct-2-ene-2-carboxylic acid imidazole salt (1:1)

Yield: 78.5% light yellow solid; MS(ISP): 543.2 (M+H)$^+$; IR(KBr): 1769, 1665, 1624 cm$^{-1}$.

Example A28
(E)-(6R,7R)-3-(1-Cyclopropyl-2-oxo-pyrrolidin-3-ylidenemethyl)-7-[2-(3,5-dimethyl-phenylsulfanyl)-acetylamino]-8-oxo-5-thia-1-aza-bicyclo[4.2.0]oct-2-ene-2-carboxylic acid imidazole salt (1:1)

Yield: 67.0% beige solid; MS(ISP): 514.3 (M+H)$^+$; IR(KBr): 1765, 1653, 1621 cm$^{-1}$.

Example A29
(E)-(6R,7R)-7-[2-(4-Bromo-phenylsulfanyl)-acetylamino]-3-(1-cyclopropyl-2-oxo-pyrrolidin-3-ylidenemethyl)-8-oxo-5-thia-1-aza-bicyclo[4.2.0]oct-2-ene-2-carboxylic acid imidazole salt (1:1)

Yield: 75.5% light yellow solid; MS(ISP): 566.1 (M+H)$^+$; IR(KBr): 1767, 1661, 1622 cm$^{-1}$.

Example A30
(E)-(6R,7R)-7-[2-(Benzooxazol-2-ylsulfanyl)-acetylamino]-3-(1-cyclopropyl-2-oxo-pyrrolidin-3-ylidenemethyl)-8-oxo-5-thia-1-aza-bicyclo[4.2.0]oct-2-ene-2-carboxylic acid imidazole salt (1:1)

Yield: 67.2% beige solid; MS(ISP): 527.1 (M+H)$^+$; IR(KBr): 1770, 1670, 1625 cm$^{-1}$.

Example A31
(E)-(6R,7R)-7-[2-(4-Bromo-phenylsulfanyl)-acetylamino]-8-oxo-3-[2-oxo-1-(2,2,2-trifluoro-ethyl)-pyrrolidin-3-ylidenemethy]-5-thia-1-aza-bicyclo[4.2.0]oct-2-ene-2-carboxylic acid imidazole salt (1:1)

Yield: 86.3% yellow powder; MS(ISP): 608.3 (M+H)$^+$; IR(KBr): 1769, 1682, 1611 cm$^{-1}$.

Example A32
(E)-(6R,7R)-8-Oxo-3-[2-oxo-1-(2,2,2-trifluoro-ethyl)-pyrrolidin-3-ylidenemethyl]-7-(2-phenylsulfanyl-acetylamino)-5-thia-1-aza-bicyclo[4.2.0]oct-2-ene-2-carboxylic acid imidazole salt (1:1)

Yield: 78.6% yellow powder; MS(ISP): 528.3 (M+H)$^+$; IR(KBr): 1771, 1681, 1612 cm$^{-1}$.

Example A33
(E)-(6R,7R)-3-(1-Benzyl-2-oxo-pyrrolidin-3-ylidenemethyl)-8-oxo-7-(2-phenylsulfanyl-acetylamino)-5-thia-1-aza-bicyclo[4.2.0]oct-2-ene-2-carboxylic acid imidazole salt (1:1)

Yield: 85.0% brown solid; MS(ISP): 536.4 (M+H)$^+$; IR(KBr): 1767, 1667, 1622 cm$^{-1}$.

Example A34
(E)-(6R,7R)-3-[1-(4-Fluoro-benzyl)-2-oxo-pyrrolidin-3-ylidenemethyl]-8-oxo-7-(2-phenylsulfanyl-acetylamino)-5-thia-1-aza-bicyclo[4.2.0]oct-2-ene-2-carboxylic acid imidazole salt (1:1)

Yield: 91.0% beige solid; MS(ISP): 554.5 (M+H)$^+$; IR(KBr): 1766, 1665, 1622 cm$^{-1}$.

Example A35
(E)-(6R,7R)-3-[1-(4-Methoxy-benzyl)-2-oxo-pyrrolidin-3-ylidenemethyl]-8-oxo-7-(phenylsulfanyl-acetylamino)-5-thia-1-aza-bicyclo[4.2.0]oct-2-ene-2-carboxylic acid imidazole salt (1:1)

Yield: 87.1% beige solid; MS(ISP): 566.5 (M+H)$^+$; IR(KBr): 1773, 1672, 1611 cm$^{-1}$.

Example A36a
(F)-(6R,7R)-3-[1-(4-Allyloxycarbonylamino-benzyl)-2-oxo-pyrrolidin-3-ylidenemethyl]-8-oxo-7-(2-phenylsulfanyl-acetylamino)-5-thia-1-aza-bicyclo[4.2.0]oct-2-ene-2-carboxylic acid imidazole salt (1:1) RO-65–2011

Yield: 82.3% brown solid; MS(ISP): 652.5 (M+NH$_4$)$^+$; IR(KBr): 1770, 1726, 1667, 1613 cm$^{-1}$.

Example A36b
(E)-(6R,7R)-3-[1-(4-Amino-benzyl)-2-oxo-pyrrolidin-3-ylidenemethyl]-8-oxo-7-(2-phenylsulfanyl-acetylamino)-5-thia-1-aza-bicyclo[4.2.0]oct-2-ene-2-carboxylic acid (E)-(6R,7R)-3- [1-(4-allyloxycarbonylamino-benzyl)-2-oxo-pyrrolidin-3-ylidenemethyl]-8-oxo-7-(2-phenylsulfanyl-acetylamino)-5-thia-1-aza-bicyclo[4.2.0]oct-2-ene-2-carboxylic acid imidazole salt (1:1) (400.0 mg, 0.57 mmol) was suspended in 20 ml dichloromethane and treated with N,O-bis(trimethylsilyl)-trifluoroacetamide (240.7 ml, 9.11 mmol). After 15 min, bis(triphenylphosphine)palladium(II) chloride (10.0 mg, 0.014 mmol), acetic acid (0.65 ml, 11.4 mmol) and tributyltin hydride (1.53 ml, 5.70 mmol) were added. After 45 min the suspension was poured under stirring on 250 ml diethyl ether, containing 3 ml of a hydrochloric acid-saturated diethyl ether solution and was stirred for 1 h. The solid material was collected by filtration, suspended in 4 ml water: acetonitrile (1:1) and the pH was adjusted to 2 with 1M hydrochloric acid. To the suspension an equal amount of MCI gel (75–150μ, Mitsubishi Kasei Corporation) was added, the organic solvent was evaporated and the residue was chromatographed on MCI gel (75–150μ, Mitsubishi Kasei Corporation) with a gradient of water:acetonitrile (9:1, 4:1, 2:1, 1:1, 1:3). The organic solvent was evaporated and the aqueous phase was freeze-dried.

Yield: 18.0% beige lyophilisate; MS(ISP): 551.5 (M+H)$^+$; IR(KBr): 1769, 1667, 1626 cm$^{-1}$.

Example A37
(E)-(6R,7R)-3-[1-(1,1-Dioxo-tetrahydro-thiophen-3-yl)-2-oxo-pyrrolidin-3-ylidenemethyl]-8-oxo-7-(2-phenylsulfanyl-acetylamino)-5-thia-1-aza-bicyclo[4.2.0]oct-2-ene-2-carboxylic acid imidazole salt (1:1) (1:1 mixture of epimers)

Yield: 56.1% beige solid; MS(ISP): 581.4 (M+H)$^+$; IR(KBr): 1771, 1673, 1618 cm$^{-1}$.

Example A38a
(E)-(6R,7R)-3-[1-(1-Allyloxycarbonyl-azetidin-3-yl)-2-oxo-pyrrolidin-3-ylidenemethyl]-8-oxo-7-(2-phenylsulfanyl-acetylamino)-5-thia-1-aza-bicyclo[4.2.0]oct-2-ene-2-carboxylic acid imidazole salt (1:1)

Yield: 74.5% beige lyophilisate; MS(ISP): 585.5 (M+H)$^+$; IR(KBr): 1775, 1678, 1626 cm$^{-1}$.

Example A38b
(E)-6R,7R)-3-(1-Azetidin-1-ium-3-yl-2-oxo-pyrrolidin-3-ylidenemethyl)-8-oxo-7-(2-phenylsulfanyl-acetylamino)-5-thia-1-aza-bicyclo[4.2.0]oct-2-ene-2-carboxylate (E)-(6R,7R)-3-[1-(1-allyloxycarbonyl-azetidin-3-yl)-2-oxo-pyrrolidin-3-ylidenemethyl]-8-oxo-7-(2-phenylsulfanyl-acetylamino)-5-thia-1-aza-bicyclo[4.2.0]oct-2-ene-2-carboxylic acid imidazole salt (1:1) (448.0 mg, 0.69 mmol) was dissolved in 20 ml dichloromethane. Acetic acid (0.79 ml, 3.70 mmol), bis(triphenylphosphine)palladium(II) chloride (11.9 mg, 0.017 mmol) and tributyltin hydride (1.86 ml, 6.90 mmol) were added successively. After 45 min the suspension was poured under stirring on 250 ml diethyl ether, containing 3 ml of a hydrochloric acid-saturated diethyl ether solution and was stirred for 1 h. The solid material was collected by filtration, suspended in water:acetonitrile (1:1) and the pH was adjusted to 2 with 1N hydrochloric acid. To the suspension an equal amount of MCI gel (75–150μ, Mitsubishi Kasei Corporation) was added, the organic solvent was evaporated and the residue was chromatographed on MCI gel (75–150μ, Mitsubishi Kasei Corporation) with a gradient of water:acetonitrile (9:1, 4:1, 2:1, 1:1, 1:3). The organic solvent was evaporated and the aqueous phase was freeze-dried.

Yield: 23.2% beige lyophilisate; MS(ISP): 501.4 (M+H)$^+$; IR(KBr): 1766, 1673, 1620 cm$^{-1}$.

Example A39

(E)-(6R,7R)-3-[1-(4-Hydroxy-benzyl)-2-oxo-pyrrolidin-3-ylidenemethyl]-8-oxo-7-(2-phenylsulfanyl-acetylamino)-5-thia-1-aza-bicyclo[4.2.0]oct-2-ene-2-carboxylic acid imidazole salt (1:1)

Yield: 68.0% yellow solid; MS(ISP): 552.5 (M+H)$^+$; IR(KBr): 1773,1667,1614 cm$^{-1}$.

Example A40

(E)-(6R,7R)-8-Oxo-3-(2-oxo-1-phenylcarbamoylmethyl-pyrrolidin-3-ylidenemethyl)-7-(2-phenylsulfanyl-acetylamino)-5-thia-1-aza-bicyclo[4.2.0]oct-2-ene-2-carboxylic acid imidazole salt (1:1)

Yield: 52.0% brown solid; MS(ISP): 579.4 (M+H)$^+$; IR(KBr): 1770, 1665, 1599 cm$^{-1}$.

Example A41a (E)-(6R,7R)-3-[(R)-1'-Allyloxycarbonyl-2-oxo-[1,3']bipyrrolidinyl-3-ylidenemethyl]-8-oxo-7-(2-phenylsulfanyl-acetylamino)-5-thia-1-aza-bicyclo[4.2.0]oct-2-ene-2-carboxylic acid imidazole salt (1:1)

Yield: 81.3% brown solid; MS(ISP): 562.3 (M+H)$^+$; IR(KBr): 1776, 1670, 1631 cm$^{-1}$.

Example A41b (E)-(6R,7R)-8-Oxo-3-[(R)-2-oxo-[1,3'bipyrrolidinyl-3-ylidenemethyl]-7-(2-phenylsulfanyl-acetylamino)-5-thia-1-aza-bicyclo[4.2.0]oct-2-ene-2-carboxylicacid hydrochloride (1:1)

(E)-(6R,7R)-3-[(R)-1'-allyloxycarbonyl-2-oxo-[1,3']bipyrrolidinyl-3-ylidenemethyl]-8-oxo-7-(2-phenylsulfanyl-acetylamino)-5-thia-1-aza-bicyclo[4.2.0]oct-2-ene-2-carboxylic acid (370.0 mg, 0.62 mmol) was dissolved in 20 ml dichloromethane and treated successively with bis(triphenylphosphine)palladium(II) chloride (10.9 mg, 0.015 mmol), acetic acid (0.71 ml, 12.4 mmol) and tributyltin hydride (1.67 ml, 6.20 mmol). After 40 min, the suspension was poured on 250 ml diethyl ether containing 3 ml of a hydrochloric acid-saturated diethyl ether solution and stirred for 1 h. The suspension was filtered, the solid material was triturated with ethyl acetate for 1 h and dried in high vacuum.

Yield: 25.5% beige solid; MS(ISP): 515.3 (M+H)$^+$; IR(KBr): 1776, 1666, 1632 cm$^{-1}$.

Example A42

(E)-(6R,7R)-7-[2-(4-Chloro-phenylsulfanyl)-acetylamino]-3-(1-cyclopropyl-2-oxo-pyrrolidin-3-ylidenemethyl)-8-oxo-5-thia-1-aza-bicyclo[4.2.0]oct-2-ene-2-carboxylic acid imidazole salt (1:1)

Yield: 70.7% light yellow solid; MS(ISP): 520.4 (M+H)$^+$; IR(KBr): 1775, 1667, 1625 cm$^{-1}$.

The following compounds were prepared according to Example A10

Example A43

(E)-(6R,7R)-8-Oxo-3-[2-oxo-1-(2-oxo-oxazolidin-3-yl)-pyrrolidin-3-ylidenemethyl]-7-(2-phenylsulfanyl-acetylamino)-5-thia-1-aza-bicyclo[4.2.0]oct-2.-ene-2-carboxylic acid imidazole salt (1:1)

Yield: 36.0% beige lyophilisate; MS(ISP): 548.4 (M+H)$^+$; IR(KBr): 1770, 1689, 1612 cm$^{-1}$.

Example A44

(E)-(6R,7R)-8-Oxo-3-(2-oxo-1-pyridin-2-yl-pyrrolidin-3-ylidenemethyl)-7-(2-phenylsulfanyl-acetylamino)-5-thia-1-aza-bicyclo[4.2.0]oct-2-ene-2-carboxylic acid imidazole salt (1:1)

Yield: 18.0% brown lyophilisate; MS(ISP): 523.5 (M+H)$^+$; IR(KBr): 1770, 1680, 1610 cm$^{-1}$.

Example A45

(E)-(6R,7R)-3-[1-(6-Methoxy-pyridin-3-yl)-2-oxo-pyrrolidin-3-ylidenemethyl]-8-oxo-7-(2-phenylsulfanyl-acetylamino)-5-thia-1-aza-bicyclo[4.2.0]oct-2-ene-2-carboxylic acid imidazole salt (1:1)

Yield: 12.0% beige lyophilisate; MS(ISP): 553.5 (M+H)$^+$; IR(KBr): 1769, 1677, 1619 cm$^{-1}$.

Example A46

(E)-(6R,7R)-7-[2-(1H-Benzoimidazol-2-ylsulfanyl)-acetylamino]-3-[1-(4-hydrox-benzyl)-2-oxo-pyrrolidin-3-ylidenemethyl]-8-oxo-5-thia-1-aza-bicyclo[4.2.0]oct-2-ene-2-carboxylic acid imidazole salt (1:1)

Yield: 11.2% beige lyophilisate; MS(ISP): 592.5 (M+H)$^+$; IR(KBr): 1769, 1664, 1614 cm$^{-1}$.

Example A47

(E)-(6R,7R)-3-(1-Isobutyl-2-oxo-pyrrolidin-3-ylidenemethyl)-8-oxo-7-(2-phenylsulfanyl-acetylamino)-5-thia-1-aza-bicyclo[4.2.0]oct-2-ene-2-carboxylic acid imidazole salt (1:1)

Yield: 15.8% colorless lyophilisate; MS(ISP): 502.4 (M+H)$^+$; IR(KBr): 1768, 1660, 1625 cm$^{-1}$.

Example A48

(E)-(6R,7R)-3-(1-Cyclohexylmethyl-2-oxo-pyrrolidin-3-ylidenemethyl)-8-oxo-7-(2-phenylsulfanyl-acetylamino)-5-thia-1-aza-bicyclo[4.2.0]oct-2-ene-2-carboxylic acid imidazole salt (1:1)

Yield: 10.0% colorless lyophilisate; MS(ISP): 542.4 (M+H)$^+$.

Example A49

(E)-(6R,7R)-3-[1-(3-Hydroxy-benzyl)-2-oxo-pyrrolidin-3-ylidenemethyl]-8-oxo-7-(3-phenyl-propionylamino)-5-thia-1-aza-bicyclo[4.2.0]oct-2-ene-2-carboxylic acid Yield: 17.0% beige lyophilisate; MS(ISP): 534.4 (M+H)$^+$; IR(KBr): 1778, 1662, 1602 cm$^{-1}$.

Example A50

(E)-(6R,7R)-3-[(3-Hydroxy-benzyl)-oxo-pyrrolidin-3-ylidenemethyl]-7-[2-(4-hydroxymethyl-phenoxy)-acetylamino]-8-oxo-5-thia-1-aza-bicyclo[4.2.0]oct-2-ene-2-carboxylic acid imidazole salt (1:1)

Yield: 21.2% beige lyophilisate; MS(ISP): 566.4 (M+H)$^+$; IR(KBr): 1773, 1665, 1588 cm$^{-1}$.

Example A51

(E)-(6R,7R)-3-[1-[1-[(3-Fluoro-4-hydroxy-phenylcarbamoyl)-methyl-pyridin-1-ium-4-ylmethyl}]-2- oxo-pyrrolidin-3-ylidenemethyl]-7-[2-(4-hydroxymethylphenoxy)-acetylamino]-8-oxo-5-thia-1-aza-bicyclo[4.2.0]oct-2-ene-2-carboxylate Yield: 14.1% beige lyophilisate; MS(ISP): 718.3 (M+H)$^+$; ER(KBr): 1769, 1681, 1613 cm$^{-1}$.

Example A52

(E)-(6R,7R)-7-(2-Benzoylamino-acetylamino)-3-[1-(3-hydroxy-benzyl)-2-oxo-pyrrolidin-3-ylidenemethyl]-8-oxo-5-thia-1-aza-bicyclo[4.2.0]oct-2-ene-2-carboxylic acid imidazole salt (1:1)

Yield: 32% beige lyophilisate; MS(ISP): 562.0 (M+H)$^+$; IR(KBr): 1771, 1658, 1602 cm$^{-1}$.

Example A53

(E)-(6R,7R)-3-[1-(3-Hydroxy-benzyl)-2-oxo-pyrrolidin-3-ylidenemethyl]-8-oxo-7-(2-phenylamino-acetylamino)-5-thia-1-aza-bicyclo[4.2.0]oct-2-ene-2-carboxylic acid imidazole salt (1:1)

Yield: 20.5% beige lyophilisate; MS(ISP): 535.4 (M+H)$^+$; IR(KBr): 1780, 1670, 1608 cm$^{-1}$.

Example A54

(E)-(6R,7R)-3-[1-(3-Hydroxy-benzyl)-2-oxo-pyrrolidin-3-ylidenemethyl]-8-oxo-7-(2-phenoxy-acetylamino)-5-thia-1-aza-bicyclo[4.2.0]oct-2-ene-2-carboxylic acid imidazole salt (1:0.8)

Yield: 34.6% beige lyophilisate; MS(ISP): 536.2 (M+H)$^+$; IR(KBr): 1776, 1673, 1600 cm$^{-1}$.

Example A55

(6R,7R)-3-[(E)-1-(3-Hydroxy-benzyl)-2-oxo-pyrrolidin-3-ylidenemethyl]-8-oxo-7-[(Z)-2-styrylsulfanyl-acetylamino]-5-thia-1-aza-bicyclo[4.2.0]oct-2-ene-2-carboxylic acid Yield: 31.6% beige lyophilisate; MS(ISP): 578.4 (M+H)$^+$; IR(KBr): 1775, 1663, 1619 cm$^{-1}$.

Example A56

(6R,7R)-3-[(E)-1-[1-[[(3-Fluoro-4-hydroxy-phenylcarbamoyl)-methyl]-pyridin-1-ium-4-ylmethyl]-2-oxo-pyrrolidin-3-ylidenemethyl]-8-oxo-7- [(Z)-2-styrylsulfanylacetylamino]-5-thia-1-aza-bicyclo[4.2.0]oct-2-ene-2-carboxylate Yield: 14.2% beige lyophilisate; MS(ISP): 730.5 (M+H)$^+$; IR(KBr): 1769, 1677, 1642 cm$^{-1}$.

Example A57

(E)-(6R,7R)-7-[2-(4-Chloro-phenylsulfanyl)-acetylamino]-3-[1-(3-hydroxy-benzyl)-2-oxo-pyrrolidin-3-ylidenemethyl]-8-oxo-5-thia-1-aza-bicyclo[4.2.0]oct-2-ene-2-carboxylic acid imidazole salt (1:1)

Yield: 29.0% light yellow lyophilisate; MS(ISP): 586.3 (M+H)$^+$; IR(KBr): 1769, 1669, 1600 cm$^{-1}$.

Example A58

(E)-(6R,7R)-7-[2-(4-Bromo-phenylsulfanyl)-acetylamino]-3-[1-[1-[[(3-fluoro-4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate Yield: 13.3% beige lyophilisate; MS(ISP): 748.1 (M+H)$^+$; IR(KBr): 1769, 1676, 1642 cm$^{-1}$.

Example A59

(E)-(6R,7R)-7-[2-(3,5-Dimethyl-phenylsulfanyl)-acetylamino]-3-[1-[1-[[(3-fluoro-4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate Yield: 24.0% light brown lyophilisate; MS(ISP): 732.4 (M+H)$^+$; IR(KBr): 1766, 1667, 1644 cm$^{-1}$;

Example A60

(E)-(6R,7R)-3-(1-Cyclopropyl-2-oxo-pyrrolidin-3-ylidenemethyl)-8-oxo-7-[2-(pyridin-4-ylsulfanyl)-acetylamino]-5-thia-1-aza-bicyclo[4.2.0]oct-2-ene-2-carboxylic acid imidazole salt (1:1)

Yield: 46.0% light yellow lyophilisate; MS(ISP): 486.4 (M+H)$^+$; IR(KBr): 1769, 1664, 1619 cm$^{-1}$.

Example A61

(E)-(6R,7R)-3-(1-Cyclopropyl-2-oxo-pyrrolidin-3-ylidenemethyl)-8-oxo-7-[2-(pyridin-4-ylsulfanyl)-acetylaminol-5-thia-1-aza-bicyclo[4.2.0]oct-2-ene-2-carboxylic acid imidazole salt (1:1)

Yield: 41.0% light yellow lyophilisate; MS(ISP): 487.2 (M+H)$^+$; IR(KBr): 1772, 1672, 1623 cm$^{-1}$.

Example A62

(E)-(6R,7R)-7-[2-(4-Fluoro-phenylsulfanyl)-acetylamino]-8-oxo-3-(2-oxo-1-phenylcarbamoylmethyl-pyrrolidin-3-ylidenemethyl)-5-thia-1-aza-bicyclo[4.2.0]oct-2-ene-2-carboxylic acid sodium salt (1:1)

(4-Fluorophenylthio)acetic acid (102.7 mg, 0.55 mmol) was dissolved in N,N-dimethylacetamide and 1,1,-carbonyldiimidazole (89.0 mg, 0.55 mmol) was added in a single portion. The solution was stirred for 20 min, then (E)-(6R,7R)-7-amino-8-oxo-3-(2-oxo-1-phenylcarbamoylmethyl-pyrrolidin-3-ylidenemethyl)-5-thia-1-aza-bicyclo[4.2.0]oct-2-ene-2-carboxylic acid was added. After 6 h the mixture was poured on 250 ml diethyl ether and the solid material was collected by filtration. The solid was converted into its sodium salt by suspending it in 6 ml water and adjusting the pH to 7 with 1M sodium hydroxide solution. The solution was chromatographed on MCI gel (75–150μ, Mitsubishi Kasei Corporation) with a gradient of water:acetonitrile (10:1, 8:2, 7:3). The organic solvent was stripped off at a rotary evaporator and the aqueous phase was freeze-dried.

Yield: 75.2% yellow lyophilisate; MS(ISP): 597.2 (M+H)$^+$; IR(KBr): 1770, 1668, 1630 cm$^{-1}$.

The following compounds were prepared according to Example A62

Example A63

(E)-(6R,7R)-8-Oxo-3-(2-oxo-1-phenyl-pyrrolidin-3-ylidenemethyl)-7-(2-phenylsulfanyl-acetylamino)-5-thia-1-aza-bicyclo[4.2.0]oct-2-ene-2-carboxylic acid sodium salt (1:1)

Yield: 56.3% beige lyophilisate; MS(ISP): 522.2 (M+H)$^+$; IR(KBr): 1765, 1682, 1622 cm$^{-1}$.

Example A64

(E)-(6R,7R)-3-[1-(2-Methyl-allyl)-2-oxo-pyrrolidin-3-ylidenemethyl-8-oxo-7-(2-phenylsulfanyl-acetylamino)-5-thia-1-aza-bicyclo[4.2.0]oct-2-ene-2-carboxylic acid sodium salt (1:1)

Yield: 40.8% beige lyophilisate; MS(ISP): 500.2 (M+H)$^+$; IR(KBr): 1765, 1667, 1614 cm$^{-1}$.

Example A65

(E)-(6R,7R)-7-[2-(Benzooxazol-2-ylsulfanyl)-acetylamino]-3-[1-(4-hydroxy-benzyl)-2-oxo-pyrrolidin-3-ylidenemethyl]-8-oxo-5-thia-1-aza-bicyclo[4.2.0]oct-2-ene-2-carboxylic acid sodium salt (1:1)

Yield: 43.3% beige lyophilisate; MS(ISP): 593.2 (M+H)$^+$; IR(KBr): 1770, 1670, 1615 cm$^{-1}$.

Example A66

(E)-(6R,7R)-7-(2-Benzylsulfanyl-acetylamino)-3-[1-(4-hydroxy-benzyl)-2-oxo-pyrrolidin-3-ylidenemethyl]-8-oxo-5-thia-1-aza-bicyclo[4.2.0]oct-2-ene-2-carboxylic acid sodium salt (1:1)

Yield: 38.7% beige lyophilisate; MS(ISP): 583.3 (M+H)$^+$; IR(KBr): 1764, 1664, 1614 cm$^{-1}$.

Example A67

(E)-(6R,7R)-7-[2-(5-Acetylamino-[1,3,4]thiadiazol-2-ylsulfanyl)-acetylamino]-3-[1-(4-hydroxy-benzyl)-2-oxo-pyrrolidin-3-ylidenemethyl]-8-oxo-5-thia-1-aza-bicyclo[4.2.0]oct-2-ene-2-carboxylic acid sodium salt (1:1)

Yield: 40.4% yellow lyophilisate; MS(ISP): 617.2 (M+H)$^+$; IR(KBr): 1766, 1657, 1614 cm$^{-1}$.

Example A68

(E)-(6R,7R)-3-[1-(4-Hydroxy-benzyl)-2-oxo-pyrrolidin-3-ylidenemethyl]-7-(2-methylsulfanyl-acetylamino)-8-oxo-5-thia-1-aza-bicyclo[4.2.0]oct-2-ene-2-carboxylic acid sodium salt (1:1)

Yield: 43.0% beige lyophilisate; MS(ISP): 490.3 (M+H)$^+$; IR(KBr): 1764, 1664, 1614 cm$^{-1}$.

Example A69

(E)-(6R,7R)-7-[2-(4-Bromo-phenylsulfanyl)-acetylamino]-8-oxo-3-(2-oxo-1-pheny-pyrrolidin-3-ylidenemethyl)-5-thia-1-aza-bicyclo[4.2.0]oct-2-ene-2-carboxylic acid sodium salt Yield: 53.0% yellow lyophilisate; MS(ISP): 602.1 (M+H)$^+$; IR(KBr): 1764, 1673, 1618 cm$^{-1}$.

Example A70

(E)-(6R,7R)-7-12-(Naphthalen-2-ylsulfanyl)-acetylamino]-8-oxo-3-[2-oxo-1-(2,2,2-trifluoro-ethyl)-pyrrolidin-3-ylidenemethyl]-5-thia-1-aza-bicyclo[4.2.0]oct-2-ene-2-carboxylic acid sodium salt (1:1); compound with imidazole (1:0.5)

Yield: 28.3% yellow lyophilisate; MS(ISP): 578.1 (M+H)$^+$; IR(KBr): 1770, 1682, 1620 cm$^{-1}$.

The Following Compound was Prepared According to Example A1

Example A71

1:1 Mixture of (E)-(6R,7R)-8-Oxo-3-[2-oxo-1-[(R)- and -[(S)-tetrahydro-furan-2-ylmethyl]-pyrrolidin-3-ylidenemethyl]-7-(2-phenylsulfanyl-acetylamino)-5-thia-1-aza-bicyclo[4.2.0]oct-2-ene-2-carboxylic acid imidazole salt (1:1)

Yield: 88.0% yellow lyophilisate; MS(ISP): 530.2 (M+H)$^+$; IR(KBr): 1772, 1672, 1619 cm$^{-1}$.

Method B

Example B1

(E)-(6R,7R)-3-(1-Cyclopropylmethyl-2-oxo-pyrrolidin-3-ylidenemethyl)-8-oxo-7-(2-thiophen-2-yl-acetylamino)-5-thia-1-aza-bicyclo[4.2.0]oct-2-ene-2-carboxylic acid

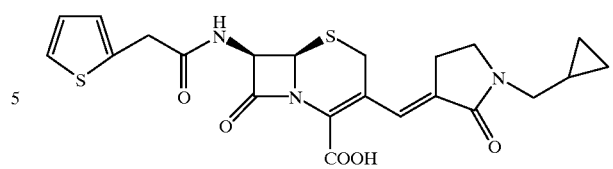

To a suspension of 300.0 mg (0.86 mmol) (E)-(6R,7R)-7-amino-3-(1-cyclopropylmethyl-2-oxo-pyrrolidin-3-ylidenemethyl)-8-oxo-5-thia-1-azabicyclo-[4.2.0]oct-2-ene-2-carboxylic acid in 8 ml N,N-dimethylformamide was added 80.0 mg (0.95 mmol) sodium bicarbonate. After cooling to 0° C. 101.0 μl (0.95 mmol) 2-thiopheneacetyl chloride were added. After 1.5 h the solvent was stripped off at a rotary evaporator and the residue was poured on diethyl ether. The solid was collected by filtration and was triturated with 25 ml ethyl acetate and 15 ml water for 1.5 h.

Yield: 150.0 mg (36.9%) beige powder; IR(KBr): 1779, 1669, 1626, 1540 cm$^{-1}$; MS(ISP): 474.2 (M+H$^+$).

Example B2

Mixture of (E)-(6R,7R)-3-(1-cyclopropylmethyl-2-oxo-pyrrolidin-3-ylidenemethyl)-7-[(R)- and [(S)-2,3-diphenyl-propionylamino)]-8-oxo-5-thia-1-aza-bicyclo[4.2.0]oct-2-ene-2-carboxylic acid

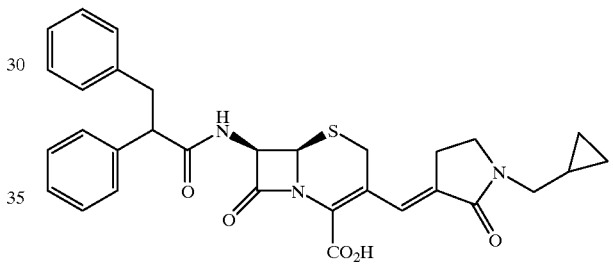

From 100.0 mg (0.29 mmol) (E)-(6R,7R)-7-amino-3-(1-cyclopropylmethyl-2-oxo-pyrrolidin-3-ylidenemethyl)-8-oxo-5-thia-1-azabicyclo [4.2.0]oct-2-ene-2-carboxylic acid, 26.4 mg (0.31 mmol) sodium bicarbonate and 77.0 mg (0.31 mmol) 2,3-diphenylpropionyl chloride in 8 ml N,N-dimethylformamide.

Yield: 82.0 mg (51.4%) yellow powder; IR(KBr): 1782, 1671 cm$^{-1}$; MS(ISP): 558.4 (M+H$^+$).

Example B3

(E)-(6R,7R)-7-[2-(4-Chloro-phenylsulfanyl)-2-methyl-propionylamino]-3-(1-cyclopropylmethyl-2-oxo-pyrrolidin-3-ylidenemethyl)-8-oxo-5-thia-1-aza-bicyclo[4.2.0]oct-2-ene-2-carboxylic acid sodium salt (1:1)

Prepared according to Example B1.

The beige solid was suspended in water and the pH was adjusted to 7 with 1M sodium hydroxide solution. The resulting solution was chromatographed on MCI gel (75–150μ, Mitsubishi Kasei Corporation) with a gradient of water:acetonitrile (9:1, 8:2, 7:3). The organic solvent was stripped off at a rotary evaporator and the aqueous phase was freeze-dried.

Yield: 56.0% beige lyophilisate; IR(KBr): 1765, 1669, 1620 cm$^{-1}$; MS(ISP): 562.3 (M+H$^+$).

Method C

Example C1a (E)-(6R,7R)-7-(2-Bromo-acetylamino)-3-(1-[1-[(3-fluoro-4-hydroxy-phenyl-carbamoyl)-methyl]-pyridin-1-ium-4- ylmethyl]-2-oxo-pyrrolidin-3-ylidene-methyl)-8-oxo-5-thia-1-aza-bicyclo[4.2.0]oct-2-ene-2-carboxylate phenylsulfanyl)-acetylamino]-8-oxo-5-thia-1-aza-bicyclo[4.2.0]oct-2-ene-2-carboxylate

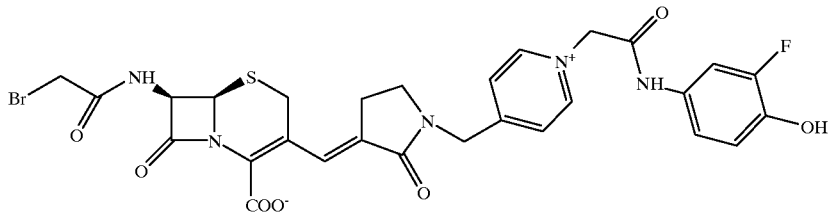

To a suspension of 280.0 mg (0.42 mmol) (E)-(6R,7R)-7-amino-3-[1-[1-[(3-fluoro-4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate trifluoroacetate in 4 ml dichloromethane were added 0.37 µl (1.40 mmol) N,O-bis-(trimethylsilyl)-trifluoroacetamide. After a clear solution had formed, 36.8 µl (0.42 mmol) bromoacetyl bromide were added and the reaction mixture was stirred for 3 h. To this solution 25.6 µl (1.42 mmol) water and 25 ml diethyl ether was added. The precipitate was filtered off and washed with diethyl ether.

Yield: 210.0 mg (77.8%) beige powder; IR(KBr): 1782, 1686, 1643 cm⁻¹; MS(ISP): 676.2 (M+H⁺).

Example C1b
(E)-(6R,7R)-3-[1-[1-[(3-Fluoro-4-hydroxy-phenylcarbamoyl)-methyl]-pyridin-1-ium-4-ylmethyl]-2-oxo-pyrrolidin-3-ylidenemethyl]-7-[2-(4-methyl-4H-[1,2,4]-triazol-3-ylsulfanyl)-acetylamino]-8-oxo-5-thia-1-aza-bicyclo[4.2.0]oct-2-ene-2-carboxylate (E)-(6R,7R)-7-(2-bromo-acetylamino)-3-[1-[1-[(3-fluoro-4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate (see ex. C1a) (300.0 mg, 0.45 mmol) was dissolved in 3 ml N,N-dimethylformamide, then 4-mercaptophenol (58.0 mg, 0.45 mmol), followed by triethylamine (62.7 ml, 0.45 mmol) was added. After 22 h the reaction mixture was poured on diethyl ether and the solid was collected by filtration. The brown solid material was suspended in water: acetonitrile (1:1) and chromatographed on MCI gel (75–150µ, Mitsubishi Kasei Corporation) with a gradient of water: acetonitrile (9:1, 4:1, 3:1). The organic solvent was stripped off at a rotary evaporator and the aqueous phase was freeze-dried.

Yield: 14.0% beige solid; MS(ISP): 720.4 (M+H)⁺; IR(KBr): 1769, 1671,1643 cm⁻¹.

Example C3
(E)-(6R,7R)-3-(1-Cyclopropylmethyl-2-oxo-pyrrolidin-3-ylidenemethyl)-8-oxo-7-[2-(thiophen-2-ylsulfanyl)-

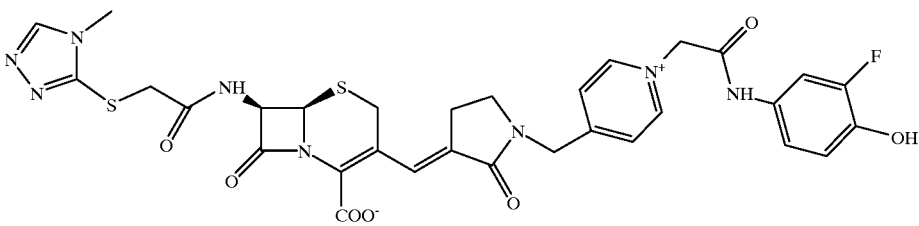

To a solution of 230.0 mg (0.34 mmol) (E)-(6R,7R)-7-(2-Bromo-acetylamino)-3-(1-[1-[(3-fluoro-4-hydroxy-phenylcarbamoyl)-methyl]-pyridin-1-ium-4-ylmethyl]-2-oxo-pyrrolidin-3-ylidenemethyl)-8-oxo-5-thia-1-aza-bicyclo[4.2.0]oct-2-ene-2-carboxylate in 5 ml N,N-dimethylformamide was added 40.0 mg (0.37 mmol) 4-methyl-4H-[1,2,4]triazole-3-thiol. After 1 h 47.0 µl (0.34 mmol) triethyl amine was added and stirring was continued for 12 h. The solution was poured on diethyl ether and the resulting solid was purified by column chromatography on MCI gel (75–150µ, Mitsubishi Kasei Corporation) with a gradient of water:acetonitrile (1:0, 4:1, 3:1, 2:1). The organic solvent was stripped off at a rotary evaporator and the aqueous phase was freeze-dried.

Yield: 48.4 mg (20.0%) beige lyophilisate; IR(KBr): 1780, 1660,1647 cm⁻¹; MS(ISP): 709.3 (M+H⁺).

Example C2
(E)-(6R,7R)-3-[1-[1-[(3-Fluoro-4-hydroxy-phenylcarbamoyl)-methyl]-pyridin-1-ium-4-ylmethyl]-2-oxo-pyrrolidin-3-ylidenemethyl]-7-[2-(4-hydroxyacetylamino]-5-thia-1-aza-bicyclo[4.2.0]oct-2-ene-2-carboxylic acid Prepared according to Example C1
Yield: 24.2% beige lyophilisate; MS(ISP): 506.2 (M+H)⁺; IR(KBr): 1781, 1719, 1667 cm⁻¹.

Example C4a
(E)-(6R,7R)-7-(2-Bromo-acetylamino)-3-(1-cyclopropyl-2-oxo-pyrrolidin-3-ylidenemethyl)-8-oxo-5-thia-1-aza-bicyclo[4.2.0]oct-2-ene-2-carboxylic acid sodium salt (1:1)
(E)-(6R,7R)-7-amino-3-[(1-cyclopropyl-2-oxo-3-pyrrolidinylidene)methyl]-8-oxo-5-thia-1-azabicyclo[4.2.0]oct-2-ene-2-carboxylic acid trifluoroacetate (1:0.25) (8.0 g, 22.0 mmol) was suspended in 100 ml dichloromethane and N-methyl-N-(trimethylsilyl)trifluoroacetamide (9.0 ml, 48.4 mmol) was added. After 45 min a solution had formed which was cooled to 0° C. and treated with bromoacetyl bromide (2.10 ml, 24.2 mmol). After 30 min the ice-bath was removed and the reaction was stirred at ambient temperature for 2.5 h. The volatile components were evaporated and the residue was converted into its sodium salt by suspending it in water and adjusting the pH to 6.5 with 1M sodium hydroxide solution. The solution was freeze-dried and the crude lyophilisate was purified by reversed phase chromatography (RP-18 LiChroPrep gel) with a gradient of water:acetonitril (10:0, 9:1). The organic solvent was evaporated and the aqueous phase was freeze-dried.

Yield: 60.0% light yellow lyophilisate; MS(ISP): 465.2 (M+H)$^+$; IR(KBr): 1766, 1672, 1620 cm$^{-1}$.

Example C4b
(E)-(6R,7R)-3-(1-Cyclopropyl-2-oxo-pyrrolidin-3-ylidenemethyl)-7-12-(1H-imidazol-2-ylsulfanyl)-acetylamino]-8-oxo-5-thia-1-aza-bicyclo[4.2.0]oct-2-ene-2-carboxylic acid sodium salt (1:1)

(E)-(6R,7R)-7-(2-bromo-acetylamino)-3-(1-cyclopropyl-2-oxo-pyrrolidin-3-ylidenemethyl)-8-oxo-5-thia-1-aza-bicyclo[4.2.0]oct-2-ene-2-carboxylic acid sodium salt (1:1) (200.0 mg, 0.42 mmol) was dissolved in 4 ml N,N-dimethylformamide and 2-mercaptoimidazole sodium salt (56.2 mg, 0.46 mmol) was added in a single portion. After 15 h the solvent was stripped off at a rotary evaporator. The residue was dissolved in water and purified by reversed phase chromatography (RP-18 LiChroPrep gel) with a gradient of water:acetonitril (13:0, 9:1, 8:2). The organic solvent was evaporated and the aqueous phase was freeze-dried.

Yield: 82.2% colorless lyophilisate; MS(ISP): 476.1 (M+H)$^+$; IR(KBr): 1764, 1664, 1620 cm$^{-1}$.

The following compounds were prepared according to Example C4

Example C5
(E)-(6R,7R)-7-[2-(4—Carboxy-phenylsulfanyl)-acetylamino]-3-(1-cyclopropyl-2-oxo-pyrrolidin-3-ylidenemethyl)-8-oxo-5-thia-1-aza-bicyclo[4.2.0]oct-2-ene-2-carboxylic acid sodium salt (1:2)

Yield: 57.6% yellowish lyophilisate; MS(ISP): 530.2 (M+H)$^+$; IR(KBr): 1755, 1658, 1589 cm$^{-1}$.

Example C6
(E)-(6R,7R)-3-(1-Cyclopropyl-2-oxo-pyrrolidin-3-ylidenemethyl)-7-[2-(4-hydroxy-phenylsulfanyl)-acetylaminol-8-oxo-5-thia-1-aza-bicyclo[4.2.0]oct-2-ene-2-carboxylic acid sodium salt (1:1)

Yield: 72.2% yellow lyophilisate; MS(ISP): 502.0 (M+H)$^+$; IR(KBr): 1764, 1661, 1620 cm$^{-1}$.

Example C7
(E)-(6R,7R)-7-[2-(1—Carboxymethyl-1H-tetrazol-5-ylsulfanyl)-acetylamino]-3-(1-cyclopropyl-2-oxo-pyrrolidin-3-ylidenemethyl)-8-oxo-5-thia-1-aza-bicyclo[4.2.0]oct-2-ene-2-carboxylic acid disodium salt Yield: 49.1% beige lyophilisate; MS(ISP): 558.2 (M+H)$^+$; IR(KBr): 1764, 1622 cm$^{-1}$.

Example C8
(E)-(6R,7R)-3-(1-Cyclopropyl-2-oxo-pyrrolidin-3-ylidenemethyl)-8-oxo-7-[2-(1-phenyl-1H-tetrazol-5-ylsulfanyl)-acetylamino]-5-thia-1-aza-bicyclo[4.2.0]oct-2-ene-2-carboxylic acid sodium salt (1:1)

Yield: 81.8% colorless lyophilisate; MS(ISP): 554.2 (M+H)$^+$; IR(KBr): 1764, 1672, 1619 cm$^{-1}$.

Example C9
(E)-(6R,7R)-3-(1-Cyclopropyl-2-oxo-pyrrolidin-3-ylidenemethyl)-8-oxo-7-[2-(2-oxo-3,7-dihydro-2H-purin-6-ylsulfanyl)-acetylamino]-5-thia-1-aza-bicyclo[4.2.0]oct-2-ene-2-carboxylic acid sodium salt (1:1)

Yield: 40.6% light beige lyophilisate; MS(ISP): 544.4 (M+H)$^+$; IR(KBr): 1762, 1625 cm$^{-1}$.

Example C10
(E)-(6R,7R)-3-(1-Cyclopropyl-2-oxo-pyrrolidin-3-ylidenemethyl)-8-oxo-7-[2-(pyrimidin-2-ylsulfanyl)-acetylamino]-5-thia-1-aza-bicyclo[4.2.0]oct-2-ene-2-carboxylic acid sodium salt (1:1)

Yield: 27.0% colorless lyophilisate; MS(ISP): 488.4 (M+H)$^+$; IR(KBr): 1763, 1671, 1618 cm$^{-1}$.

Example C11
(E)-(6R,7R)-3-(1-Cyclopropyl-2-oxo-pyrrolidin-3-ylidenemethyl)-7-[2-(1-methyl-1H-tetrazol-5-ylsulfanyl)-acetylamino]-8-oxo-5-thia-1-aza-bicyclo[4.2.0]oct-2-ene-2-carboxylic acid sodium salt (1:1)

Yield: 38.1% colorless lyophilisate; MS(ISP): 492.4 (M+H)$^+$; IR(KBr): 1764, 1678, 1618 cm$^{-1}$.

Example C12
(E)-(6R,7R)-3-(1-Cyclopropyl-2-oxo-pyrrolidin-3-ylidenemethyl)-7-[2-(4-hydroxy-pyrimidin-2-ylsulfanyl)-acetylamino]-8-oxo-5-thia-1-aza-bicyclo[4.2.0]oct-2-ene-2-carboxylic acid sodium salt (1:1)

Yield: 47.3% light yellow lyophilisate; MS(ISP): 504.4 (M+H)$^+$; IR(KBr): 1762, 1670, 1616 cm$^{-1}$.

Example C13
(E)-(6R,7R)-3-(1-Cyclopropyl-2-oxo-pyrrolidin-3-ylidenemethyl)-7-[2-[2-(3,4-dihydroxy-phenyl)-5-methyl-[1,2,4]triazolo[1,5-a]pyrimidin-7-ylsulfanyl]-acetylamino]-8-oxo-5-thia-1-aza-bicyclo[4.2.0]oct-2-ene-2-carboxylic acid sodium salt (1:1)

Yield: 27.3% colorless lyophilisate; MS(ISP): 650.4 (M+H)$^+$; IR(KBr): 1768, 1660, 1618 cm$^{-1}$.

Example C14
(E)-(6R,7R)-3-(1-Cyclopropyl-2-oxo-pyrrolidin-3-ylidenemethyl)-7-[2-(4-methyl-5-trifluoromethyl-4H-[1,2,4]triazol-3-ylsulfanyl)-acetylamino]-8-oxo-5-thia-1-aza-bicyclo[4.2.0]oct-2-ene-2-carboxylic acid sodium salt (1:1)

Yield: 48.6% light yellow lyophilisate; MS(ISP): 559.4 (M+H)$^+$; IR(KBr): 1763, 1672, 1618 cm$^{-1}$.

Example C15a
(E)-(6R,7R)-7-(2-Bromo-acetylamino)-3-(1-cyclopropylmethyl-2-oxo-pyrrolidin-3-ylidenemethyl)-8-oxo-5-thia-1-aza-bicyclo[4.2.0]oct-2-ene-2-carboxylic acid sodium salt (E)-(6R,7R)-7-amino-3-(1-cyclopropylmethyl-2-oxo-pyrrolidin-3-ylidenemethyl)-8-oxo-5-thia-1-azabicyclo[4.2.0]oct-2-ene-2-carboxylic acid (3.50 g, 10.0 mmol) was suspended in 50 ml dichloromethane and N-methyl-N-trimethylsilyltrifluoroacetamide (4.62 ml, 25.0 mmol) was added dropwise. After 1h a solution had formed which was cooled to 0° C. To this solution bromoacetyl bromide (1.04 ml, 12.0 mmol) was added. After 30 min the ice-bath was removed and the solution was stirred for 4 h at room temperature. After evaporation of the volatile components, the residue was suspended in water and the pH was adjusted to 6.8 with 1N sodium hydroxide solution and freeze-dried. The crude lyophilisate was purified by reversed phase chromatography (RP-18 LiChroPrep gel) with a gradient of water:acetonitrile (9:1, 8:2, 7:3). The organic solvent was evaporated and the aqueous phase was freeze-dried.

Yield: 67.1% yellow lyophilisate; MS(ISP): 470.0 (M+H)$^+$; IR(KBr): 1766, 1665, 1622 cm$^{-1}$.

The following compounds were prepared according to Example C4

Example C15b
(E)-(6R,7R)-3-(1-Cyclopropylmethyl-2-oxo-pyrrolidin-3-ylidenemethyl)-8-oxo-7-[2-(3H-[1,2,3]triazol-4-ylsulfanyl)-acetylamino]-5-thia-1-aza-bicyclo[4.2.0]oct-2-ene-2-carboxylic acid sodium salt (1:1)

Yield: 52.1% yellowish lyophilisate; MS(ISP): 491.4 (M+H)$^+$; IR(KBr): 1764, 1664, 1619 cm$^{-1}$.

Example C16
(E)-(6R,7R)-3-(1-Cyclopropylmethyl-2-oxo-pyrrolidin-3-ylidenemethyl)-7-[2-[2-(3,4-dihydroxy-phenyl)-5-methyl-[1,2,4]triazolo[1,5-a]pyrimidin-7-ylsulfanyl]-acetylamino]-8-oxo-5-thia-1-aza-bicyclo [4.2.0]oct-2-ene-2-carboxylic acid sodium salt (1:1)

Yield: 38.3% colorless lyophilisate; MS(ISP): 664.1 (M+H)$^+$; IR(KBr): 1766, 1665, 1593 cm$^{-1}$.

Example C17
(E)-(6R,7R)-3-(1-Cyclopropylmethyl-2-oxo-pyrrolidin-3-ylidenemethyl)-8-oxo-7- [2-(1H-[1,2,4]triazol-3-ylsulfanyl)-acetylamino]-5-thia-1-aza-bicyclo[4.2.0]oct-2-ene-2-carboxylic acid sodium salt (1:1)

Yield: 51.2% yellowish lyophilisate; MS(ISP): 491.4 (M+H)$^+$; IR(KBr): 1765, 1664, 1619 cm$^{-1}$.

Example C18
(E)-(6R,7R)-3-(1-Cyclopropylmethyl-2-oxo-pyrrolidin-3-ylidenemethyl)-8-oxo-7-[2-(1H-pyrazolo[3,4-d]pyrimidin-4-ylsulfanyl)-acetylamino]-5-thia-1-aza-bicyclo[4.2.0]oct-2-ene-2-carboxylic acid sodium salt (1:1)

Yield: 20.1% yellowish lyophilisate; MS(ISP): 542.3 (M+H)$^+$; IR(KBr): 1764, 1666, 1625 cm$^{-1}$.

Example C19
(E)-(6R,7R)-3-(1-Cyclopropylmethyl-2-oxo-pyrrolidin-3-ylidenemethyl)-7-[2-(4-methyl-5-trifluoromethyl-4H-[1,2,4]triazol-3-ylsulfanyl)-acetylamino]-8-oxo-5-thia-1-aza-bicyclo[4.2.0]oct-2-ene-2-carboxylic acid sodium salt (1:1)

Yield: 52.2% yellowish lyophilisate; MS(ISP): 573.3 (M+H)$^+$; IR(KBr): 1763, 1665, 1612 cm$^{-1}$.

Example C20
(E)-(6R,7R)-3-(1-Cyclopropylmethyl-2-oxo-pyrrolidin-3-ylidenemethyl)-7-[2-(1-methyl-1H-tetrazol-5-ylsulfanyl)-acetylamino]-8-oxo-5-thia-1-aza bicyclo[4.2.0]oct-2-ene-2-carboxylic acid sodium salt (1:1)

Yield: 50.8% yellowish lyophilisate; MS(ISP): 506.3 (M+H)$^+$; IR(KBr): 1763, 1667, 1615 cm$^{-1}$.

Example C21a
Mixture of (E)-(6R,7R)-7-[(R)- and -[(S)-2-bromo-propionylamino]-3-(1-cyclopropylmethyl-2-oxo-pyrrolidin-3-ylidenemethyl)-8-oxo-6-thia-1-aza-bicyclo[4.2.0]oct-2-ene-2-carboxylic acid sodium salt (1:1), see ex. D1a

Example C21b
Mixture of (E)-(6R,7R)-3-(1-cyclopropylmethyl-2-oxo-pyrrolidin-3-ylidenemethyl)-7-[(R)- and -[(S)-2-(4-methyl-5-trifluoromethyl-4H-[1,2,4]triazol-3-ylsulfanyl)-propionylamino]- 8-oxo-5-thia-1-aza-bicyclo[4.2.0]oct-2-ene-2-carboxylic acid sodium salt (1:1)

Prepared according to Example C4

Yield: 55.0% colorless lyophilisate; MS(ISP): 587.3 (M+H)$^+$; IR(KBr): 1765, 1670, 1618 cm$^{-1}$.

Example C22
Mixture of (E)-(6R,7R)-3-(1-cyclopropylmethyl-2-oxo-pyrrolidin-3-ylidenemethyl)-8-oxo-7-[(R)- and -[(S)-2-(3H-[1,2,3]triazol-4-ylsulfanyl)-propionylamino]-5-thia-1-aza-bicyclo[4.2.0]oct-2-ene-2-carboxylic acid sodium salt (1:1)

Yield: 63.3% beige lyophilisate; MS(ISP): 505.2 (M+H)$^+$; IR(KBr): 1764, 1657, 1621 cm$^{-1}$.

Example C23
(E)-(6R,7R)-7-[2-(1H-Benzoimidazol-2-ylsulfanyl)-acetylamino]-3-(1-cyclopropyl-2-oxo-pyrrolidin-3-ylidenemethyl)-8-oxo-5-thia-1-aza-bicyclo[4.2.0]oct-2-ene-2-carboxylic acid sodium salt (1:1)

(E)-(6R,7R)-7-(2-bromo-acetylamino)-3-(1-cyclopropyl-2-oxo-pyrrolidin-3-ylidenemethyl)-8-oxo-5-thia-1-aza-bicyclo[4.2.0]oct-2-ene-2-carboxylic acid sodium salt (1:1) (see ex. C4a) (200 mg, 0.42 mmol) was dissolved in 4 ml N,N-dimethylformamide and 2-mercaptobenzimidazole sodium salt (79.2 mg, 0.46 mmol) was added in a single portion. After completion of the reaction, the solvent was stripped off at a rotary evaporator. The residue was dissolved in water and chromatographed on MCI gel (75–150μ, Mitsubishi Kasei Corporation) with a gradient of water:acetonitril (10:1, 9:1). The organic solvent was evaporated and the aqueous phase was freeze-dried.

Yield: 57.0% beige lyophilisate; MS(ISP): 526.0 (M+H)$^+$; IR(KBr): 1763, 1668, 1617 cm$^{-1}$.

The following compounds were prepared according to Example C23

Example C24
(E)-(6R,7R)-3-(1-Cyclopropyl-2-oxo-pyrrolidin-3-ylidenemethyl)-8-oxo-7-[2-(1H-pyrazolo[3,4-d]pyrimidin-4-ylsulfanyl)-acetylamino]-5-thia-1-aza-bicyclo[4.2.0]oct-2-ene-2-carboxylic acid sodium salt (1:1)

Yield: 20.0% light yellow lyophilisate; MS(ISP): 528.4 (M+H)$^+$; IR(KBr): 1764, 1667, 1618 cm$^{-1}$.

Example C25
(E)-(6R,7R)-3-(1-Cyclopropyl-2-oxo-pyrrolidin-3-ylidenemethyl)-7-[2-(2,6-dimethyl-5-oxo-2,5-dihydro-[1,2,4]triazin-3-ylsulfanyl)-acetylamino]-8-oxo-5-thia-1-aza-bicyclo[4.2.0]oct-2-ene-2-carboxylic acid sodium salt (1:1)

Yield: 33.3% beige lyophilisate; MS(ISP): 533.4 (M+H)$^+$; IR(KBr): 1762, 1629, 1478 cm$^{-1}$.

Example C26
(E)-(6R,7R)-3-(1-Cyclopropyl-2-oxo-pyrrolidin-3-ylidenemethyl)-7-[2-(2-hydroxymethyl-5-methyl-[1,2,4]triazolo[1,5-a]pyrimidin-7-ylsulfanyl)-acetylamino]-8-oxo-5-thia-1-aza-bicyclo[4.2.0]oct-2-ene-2-carboxylic acid sodium salt (1:1)

Yield: 45.5% colorless lyophilisate; MS(ISP): 572.5 (M+H)$^+$; IR(KBr): 1765, 1668, 1598 cm$^{-1}$.

Example C27
(E)-(6R,7R)-3-(1-Cyclopropyl-2-oxo-pyrrolidin-3-ylidenemethyl)-7-[2-[2-(4-hydroxy-phenyl)-5-methyl-[1,2,4]triazolo[1,5-a]pyrimidin-7-ylsulfanyl]-acetylamino]-8-oxo-5-thia-1-aza-bicyclo[4.2.0]oct-2-ene-2-carboxylic acid sodium salt (1:1)

Yield: 22.5% colorless lyophilisate; MS(ISP): 634.4 (M+H)$^+$; IR(KBr): 1765, 1666, 1613 cm$^{-1}$.

Example C28
(E)-(6R,7R)-3-(1-Cyclopropyl-2-oxo-pyrrolidin-3-ylidenemethyl)-7-[2-(4-methyl-4H-[1,2,4]triazol-3-ylsulfanyl)-acetylamino]-8-oxo-5-thia-1-aza-bicyclo[4.2.0]oct-2-ene-2-carboxylic acid sodium salt (1:1)

Yield: 53.5% beige lyophilisate; MS(ISP): 491.4 (M+H)$^+$; IR(KBr): 1764, 1673, 1615 cm$^{-1}$.

Example C29
(E)-(6R,7R)-3-(1-Cyclopropylmethyl-2-oxo-pyrrolidin-3-ylidenemethyl)-8-oxo-7-[2-(pyrimidin-2-ylsulfanyl)-acetylamino]-5-thia-1-aza-bicyclo[4.2.0]oct-2-ene-2-carboxylic acid sodium salt (1:1)

Yield: 55.2% yellowish lyophilisate; MS(ISP): 502.1 (M+H)$^+$; IR(KBr): 1762, 1664, 1614 cm$^{-1}$.

Example C30a
Mixture of (E)-(6R,7R)-7-[(R)- and -[(S)-2-bromo-propionylamino]-3-(1-cyclopropylmethyl-2-oxo-pyrrolidin-3-ylidenemethyl)-8-oxo-5-thia-1-aza-bicyclo[4.2.0]oct-2-ene-2-carboxylic acid sodium salt, see ex. D1a The following compounds were prepared according to Example C4

Example C30b
Mixture of (E)-(6R,7R)-3-(1-cyclopropylmethyl-2-oxo-pyrrolidin-3-ylidenemethyl)-8-oxo-7-[(R)- and -[(S)-2-(1H-pyrazolo[3,4-d]pyrimidin-4-ylsulfanyl)-propionylamino]-5-thia-1-aza-bicyclo[4.2.0]oct-2-ene-2-carboxylic acid sodium salt (1:1)

Yield: 56.2% yellow lyophilisate; MS(ISP): 556.2 (M+H)$^+$; IR(KBr): 1764, 1666, 1621 cm$^{-1}$.

Example C31
Mixture of (E)-(6R,7R)-3-(1-cyclopropylmethyl-2-oxo-pyrrolidin-3-ylidenemethyl)-7-[(R)- and -[(S)-2-(4-methyl-4H-[1,2,4]triazol-3-ylsulfanyl)-propionylamino]-8-oxo-5-thia-1-aza-bicyclo[4.2.0]oct-2-ene-2-carboxylic acid sodium salt (1:1)

Yield: 64.0% beige lyophilisate; MS(ISP): 519.2 (M+H)$^+$; IR(KBr): 1764, 1667, 1619 cm$^{-1}$.

Example C32
Mixture of (E)-(6R,7R)-3-(1-cyclopropylmethyl-2-oxo-pyrrolidin-3-ylidenemethyl)-8-oxo-7-[(R)- and -[(S)-2-(2,4,5-trichloro-phenylsulfanyl)-propionylamino]-5-thia-1-aza-bicyclo[4.2.0]oct-2-ene-2-carboxylic acid sodium salt (1:1)

Yield: 60.2% colorless lyophilisate; MS(ISP): 617.0 (M+H)$^+$; IR(KBr): 1760, 1670, 1618 cm$^{-1}$.

Example C33
(E)-(6R,7R)-7-[2-[2-(3,4-Dihydroxy-phenyl)-5-methyl-[1,2,4]triazolo[1,5-a]pyrimidin-7-ylsulfanyl]-acetylamino]-3-1-[1-[(3-fluoro-4-hydroxy-phenylcarbamoyl)-methyl]-pyridin-1-ium-ylmethyl]-2-oxo-pyrrolidin-3-ylidenemethyl)-8-oxo-5-thia-1-aza-bicyclo[4.2.0]oct-2-ene-2-carboxylate (E)-(6R,7R)-7-(2-bromo-acetylamino)-3-[1-[1-[(3-fluoro-4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate (see ex. C1a) (337.0 mg, 0.50 mmol) was dissolved in 4 ml N,N-dimethylformamide and 4-[7-mercapto-5-methyl-s-triazolo[1,5-a]pyrimidin-2-yl]pyrocatechol sodium salt (162.4 mg, 0.55 mmol) was added. After 6 h the reaction mixture was poured on diethyl ether and the solid material was filtered. The brown powder was suspended in 8 ml water:acetonitrile (3:1), the pH was adjusted to 3 with 1M hydrochloric acid and the suspension was chromatographed on MCI gel (75–150µ, Mitsubishi Kasei Corporation) with a gradient of water:acetonitrile (4:1, 3:1, 2:1, 1:1 1:2, 1:3). The organic solvent was stripped off at a rotary evaporator and the aqueous phase was freeze-dried.

Yield: 12.0% brown lyophilisate; MS(ISP): 868.4 (M+H)$^+$; IR(KBr): 1774, 1680, 1644 cm$^{-1}$.

Example C34a
(E)-(6R,7R)-7-(2-Bromo-acetylamino)-3-[1-(4-hydroxy-benzyl)-2-oxo-pyrrolidin-3-ylidenemethyl]-8-oxo-5-thia-1-aza-bicyclo[4.2.0]oct-2-ene-2 carboxylic acid (E)-(6R,7R)-7-amino-3-[1-(4-hydroxy-benzyl)-2-oxo-pyrrolidin-3-ylidenemethyl]-8-oxo-5-thia-1-aza-bicyclo[4.2.0]oct-2-ene-2-carboxylic acid (736.0 mg, 1.83 mmol) was suspended in 20 ml dichloromethane and N,O-bis(trimethylsilyl)-trifluoroacetamide (1.94 ml, 7.32 mmol) was added. After 45 min bromoacetyl bromide (167 ml, 1.92 mmol) was added dropwise. After 1 h the reaction mixture was poured on 200 ml diethyl ether containing 160 ml water. After 15 min the solid material was collected by filtration, washed with diethyl ether and dried in high vacuum.

Yield: 84.1% yellowish solid; MS(ISP): 522.3 (M+H)$^+$; IR(KBr): 1779,1667, 1615 cm$^{-1}$.

Example C34b
(E)-(6R,7R)-7-[2-(4-Carboxy-phenylsulfanyl)-acetylamino]-3-[1-(4-hydroxy-benzyl)-2-oxo-pyrrolidin-3-ylidenemethyl]-8-oxo-5-thia-1-aza-bicyclo[4.2.0]oct-2-ene-2-carboxylic acid sodium salt (1:2)

4-Mercaptobenzoic acid disodium salt (83.0 mg, 0.42 mmol) was dissolved in 4 ml N,N-dimethylformamide and (E)-(6R,7R)-7-(2-bromo-acetylamino)-3-[1-(4-hydroxy-benzyl)-2-oxo-pyrrolidin-3-ylidenemethyl]-8-oxo-5-thia-1-aza-bicyclo[4.2.0]oct-2-ene-2 carboxylic acid (200.0 mg, 0.40 mmol) was added in a single portion. After 2 h the reaction mixture was poured on diethyl ether and the solid material was collected by filtration. The beige solid was suspended in water and the pH was adjusted to 7 with 1M sodium hydroxide solution. The resulting solution was chromatographed on MCI gel (75–150µ, Mitsubishi Kasei Corporation) with a gradient of water: acetonitrile (9:1, 8:2, 7:3). The organic solvent was stripped off at a rotary evaporator and the aqueous phase was freeze-dried.

Yield: 50.0% beige lyophilisate; MS(ISP): 569.1 (M+H)$^+$; IR(Nujol): 1763, 1663,11592 cm$^{-1}$.

The following compounds were prepared according to Example C34

Example C35
(E)-(6R,7R)-7-[2-[5-Carboxy-2-(3,4-dihydroxy-phenyl)-5-methyl-[1,2,4]triazolo[1,5-a]pyrimidin-7-ylsulfanyl]-acetylamino]-3-[1-[1-[(3-fluoro-4-hydroxy-phenylcarbamoyl)-methyl]-pyridin-1-ium-ylmethyl]-2-oxo-pyrrolidin-3-ylidenemethyl)-8-oxo-5-thia-1-aza-bicyclo[4.2.0]oct-2-ene-2-carboxylate sodium salt (1:1)

Yield: 20.0% beige lyophilisate; MS(ISN): 896.3 (M−Na); IR(Nujol): 1775, 1673, 1643 cm$^{-1}$.

Example C36
(E)-(6R,7R)-7-[2-(4-Carboxy-phenoxy)-acetylamino]-3-[1-[1-[(3-fluoro-4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate sodium salt (1:2)

Yield: 20.0% brown lyophilisate; MS(ISP): 748.4 (M+H)$^+$; IR(Nujol): 1766, 1668, 1643 cm$^{-1}$.

Example C37
(E)-(6R,7R)-7-[2-[2-(3,4-Dihydroxy-phenyl)-5-methyl-[1,2,4]triazolo[1,5-a]pyrimidin-7-ylsulfanyl]-acetylamino]-3-[1-(4-hydroxy-benzyl)-2-oxo-pyrrolidin-3-ylidenemethyl]-8-oxo-5-thia-1-aza-bicyclo[4.2.0]oct-2-ene-2-carboxylic acid (E)-(6R,7R)-7-(2-bromo-acetylamino)-3-[1-(4-hydroxy-benzyl)-2-oxo-pyrrolidin-3-ylidenemethyl]-8-oxo-5-thia-1-aza-bicyclo[4.2.0]oct-2-ene-2-carboxylic acid (see ex. C34a) (200.0 mg, 0.38 mmol) was dissolved in 4 ml N,N-dimethylformamide and 4-[7-mercapto-5-methyl-s-triazolo[1,5-a]pyrimidin-2-yl]pyrocatechol sodium salt (124.0 mg, 0.42 mmol) was added. After 5 h the reaction mixture was poured on diethyl ether and the suspension was filtered. The solid material was digerated with 10 ml ethyl acetate:water (1:1) for 1 h, filtered and dried in high vacuum.

Yield: 70.0% beige solid; MS(ISP): 716.3 (M+H)+; IR(KBr): 1774, 1670, 1596 cm−1.

The following compound was prepared according to Example C23

Example C38
(E)-(6R,7R)-7-[2-(4-Amino-phenylsulfanyl)-acetylamino]-3-(1-cyclopropyl-2-ox4)-pyrrolidin-3-ylidenemethyl)-8-oxo-6-thia-1-aza-bicyclo[4.2.0]oct-2-ene-2-carboxylic acid sodium salt (1:1)

Yield: 37.0% beige lyophilisate; MS(ISP): 501.2 (M+H)+; IR(KBr): 1782, 1623, 1599 cm.−1.

The following compounds were prepared according to Example C33

Example C39
(E)-(6R,7R)-7-[2-(2,6-Dichloro-phenylsulfanyl)-acetylamino]-3-[1-[1-[(3-fluoro-4-hydroxy-phenylcarbamoyl)-methyl]-pyridin-1-ium-4-ylmethyl]-2-oxo-pyrrolidin-3-ylidenemethyl]-8-oxo5-thia-1-aza-bicyclo[4.2.0]oct-2-ene-2-carboxylate Yield: 19.0% beige lyophilisate; MS(ISP): 772.3 (M+H)+; IR(KBr): 1768, 1663, 1643 cm−1.

Example C40
(E)-(6R,7R)-7-[2-(3,5-Dichloro-phenylsulfanyl)-acetylamino]-3-[1-[1-[(3-fluoro-4-hydroxy-phenylcarbamoyl)-methyl]-pyridin-1-ium-4-ylmethyl]-2-oxo-pyrrolidin-3-ylidenemethyl]-8-oxo5-thia-1-aza-bicyclo[4.2.0]oct-2-ene-2-carboxylate Yield: 19.0% beige lyophilisate; MS(ISP): 772.3 (M+H)+; IR(KBr): 1769, 1677, 1643 cm−1.

Method D

Example D1a
Mixture of (E)-(6R,7R)-7-[(R)- and -[(S)-2-bromo-propionylamino]-3-(1-cyclopropylmethyl-2-oxo-pyrrolidin-3-ylidenemethyl)-8-oxo-5-thia-1-aza-bicyclo[4.2.0]oct-2-ene-2-carboxylic acid sodium salt

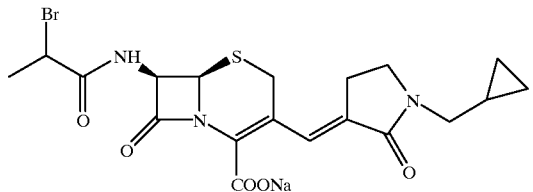

A suspension of (E)-(6R,7R)-7-amino-3-(1-cyclopropylmethyl-2-oxo-pyrrolidin-3-ylidenemethyl)-8-oxo-5-thia-1-azabicyclo[4.2.0]oct-2-ene-2-carboxylic acid (3.50 g, 10.0 mmol) in 50 ml dichloromethane was treated with N-methyl-N-trimethylsilyl-trifluoroacetamide (4.40 ml, 24.0 mmol). After 1 h a yellow solution was formed to which 2-bromo-propionyl bromide (1.30 ml, 12.0 mmol) was added dropwise at 0° C. The reaction mixture was stirred for 30 min at 0° C. and for 3 h at room temperature and then concentrated in vacuo. The oily residue was suspended in water and the pH was adjusted to 6.8 using 1 N sodium hydroxide solution. The resulting solution was purified by reversed-phase chromatography (RP-18 LiChro-Prep gel, water:acetonitrile=1:0, 4:1).

Yield: 2.80 g (55.0 %); IR(KBr): 1765, 1667 cm−1; MS(ISN): 482.1 (M—Na)+.

Example D1b
Mixture of (E)-(6R,7R)-3-(1-Cyclopropylmethyl-2-oxo-pyrrolidin-3-ylidene-methyl)-7-[(R)- and -[(S)-2-(2,5-dichloro-phenylsulfanyl)-propionylamino]-8-oxo-5-thia-1-aza-bicyclo[4.2.0]oct-2-ene-2-carboxylic acid

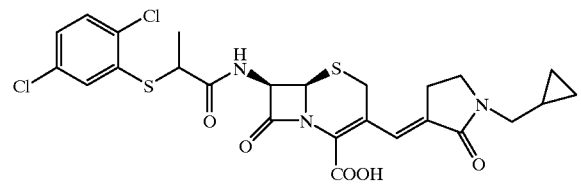

A 0.05 N solution of a mixture of (E)-(6R,7R)-7-[(R)- and -[(S)-2-bromo-propionylamino]-3-(1-cyclopropylmethyl-2-oxo-pyrrolidin-3-ylidenemethyl)- 8-oxo-5-thia-1-aza-bicyclo[4.2.0]oct-2-ene-2-carboxylic acid sodium salt in DMSO (500 µl) was treated with with a 0.05 N solution of 2,5-dichlorobenzenethiol in DMSO (500 µ) at room temperature for 24 h. MS(ISP): 599.2 (M+NH4)+.

The following compounds were synthesized according to the procedure described above:

Example D2
Mixture of (E)-(6R,7R)-3-(1-Cyclopropylmethyl-2-oxo-pyrrolidin-3-ylidene-methyl)-7-[(R)- and -[(S)-[2-(1-methyl-1H-tetrazol-5-ylsulfanyl)-propionylamino]-8-oxo-5-thia-1-aza-bicyclo[4.2.0]oct-2-ene-2-carboxylic acid sodium salt

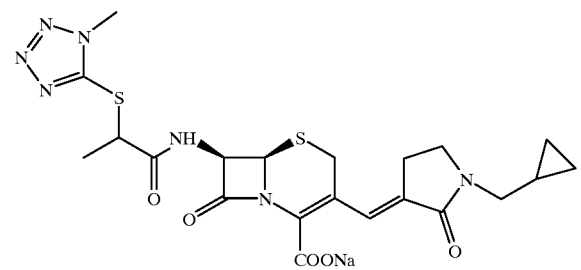

MS(ISP): 537.3 (M+NH4)+.

Example D3
Mixture of (E)-(6R,7R)-3-(1-Cyclopropylmethyl-2-oxo-pyrrolidin-3-ylidenemethyl)-8-oxo-7-[(R)- and -[(S)-[2-(pyrimidin-2-ylsulfanyl)-propionylamino]-5-thia-1-aza-bicyclo[4.2.0]oct-2-ene-2-carboxylic acid

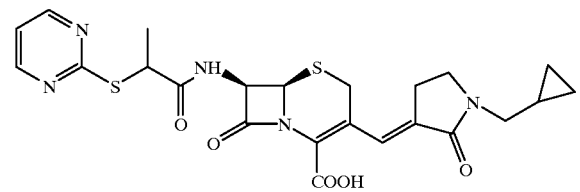

MS(ISP): 533.2 (M+NH4)+.

Example D4
Mixture of (E)-(6R,7R)-3-(1-Cyclopropylmethyl-2-oxo-pyrrolidin-3-ylidene-methyl)-7-[(R)- and -[(S)-[2-(4- methoxy-phenylsulfanyl)-propionylamino]-8-oxo-5-thia-1-aza-bicyclo[4.2.0]oct-2-ene-2-carboxylic acid

MS(ISP): 561.2 (M+NH$_4$)$^+$.

Method E

Example E1

(E)-(6R,7R)-3-[1-[1-[(4-Hydroxy-phenylcarbamoyl)-methyl]-pyridin-1-ium-4-ylmethyl]-2-oxo-pyrrolidin-3-ylidenemethyl)]-8-oxo-7-[2-(pyridin-1-ium-1-yl)-acetylamino]-5-thia-1-aza-bicyclo[4.2.0]oct-2-ene-2-carboxylate bromide To a suspension of 260.0 mg (0.40 mmol) (E)-(6R,7R)-7-amino-3-[1-[1-[(4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate trifluoroacetate in 3 ml dichloromethane were added 212 μl (0.80 mmol) N,O-bis-(trimethylsilyl)-trifluoroacetamide. After a clear solution had formed, 65 μl (0.80 mmol) pyridine and 35 μl (0.40 mmol) bromoacetyl bromide were added and the reaction mixture was stirred for 6 h. To this solution 3 ml diethyl ether and 10 μl water were added. The precipitate was filtered off, dissolved in 250 μl water:acetonitrile (3:2) and purified by reversed phase chromatography (RP-18 LiChroPrep gel, water:acetonitrile= 9:1). The organic solvent was stripped off at a rotary evaporator and the aqueous phase was freeze-dried.

Yield: 110.0 mg (45.3%) beige lyophilisate; IR(KBr): 1768, 1682, 1635, 1574 cm$^{-1}$. MS(ISP): 655.4 (M+H$^+$).

What is claimed is:

1. A compound of the formula I wherein

R$^1$ is halogen, lower alkyl, phenyl, benzyl, styryl, naphthyl or heterocyclyl; the lower alkyl, phenyl, benzyl, styryl, naphthyl and heterocyclyl being optionally substituted by at least one of halogen, hydroxy, optionally substituted lower alkyl, optionally substituted lower alkoxy, optionally substituted phenyl, amino, lower alkylamino, di-lower alkylamino, carboxy, carbamoyl, or lower alkylcarbamoyl;

R$^4$, R$^5$ independently are hydrogen, lower alkyl or phenyl;

X is S, NH or CH$_2$;

n is 0, 1 or 2;

m is 0 or 1;

s is 0 or 1;

R$^2$ is hydrogen, hydroxy, —CH$_2$—CONHR$^6$, lower alkyl-Q$_r$, cycloalkyl-Q$_r$, lower alkoxy, lower alkenyl, cycloalkenyl-Q$_r$, lower alkynyl, aralkyl-Q$_r$, aryl-Q$_r$, aryloxy, aralkoxy, a heterocyclic ring or a heterocyclyl-Q$_r$, the lower alkyl, cycloalkyl, lower alkoxy, lower alkenyl, cycloalkenyl, lower alkynyl, aralkyl, aryl, aryloxy, aralkoxy and the heterocyclic ring is optionally substituted with at least one group selected from carboxy, amino, nitro, cyano, SO$_2$NHR$^6$, optionally fluoro substituted lower alkyl, lower alkoxy, hydroxy, halogen, —CONR$^6$R$^7$, —CH$_2$CONR$^6$R$^7$, —N(R$^7$) COOR$^8$, R$^7$CO—, R$^7$OCO—, R$^7$COO—, —C(R$^7$R$^9$) CO$_2$R$^8$, —C(R$^7$R$^9$)CONR$^7$R$^{10}$, wherein R$^6$ is hydrogen, lower alkyl, cycloalkyl or aryl;

R$^7$ and R$^9$ are independently hydrogen or lower alkyl;

R$^8$ is hydrogen, lower alkyl or a lower alkenyl group; and

R$^{10}$ is hydrogen, ω-hydroxy-alkyl, phenyl, naphthyl or heterocyclyl, the phenyl, naphthyl or heterocyclyl being unsubstituted or substituted with hydroxy, halogen, optionally substituted lower alkyl or ω-hydroxyalkyl, optionally substituted lower alkoxy and/or cyano, or R$^7$ and R$^{10}$ form together group of formula Q is —CHR—, —CO— or —SO$_2$—;

r is 0 or 1;

R is hydrogen or lower alkyl; and

R$^3$ is hydroxy, —O$^-$, lower-alkoxy, or —OM and M is an alkali metal;

wherein when R$^2$ is positively charged R$^3$ is —O$^-$ and when R$^3$ is —O$^-$ R$^2$ is positively charged, wherein each heterocyclyl is independently an unsaturated or saturated, unsubstituted or substituted 4-, 5-, 6-, or 7-membered heterocyclic ring containing at least one atom selected from the group consisting of oxygen, nitrogen and sulfur;

an ester thereof which is readily hydrolyzable in vivo, a pharmaceutically acceptable salt thereof, or a hydrate thereof, or a hydrate of said ester or said salt.

2. A compound of the formula

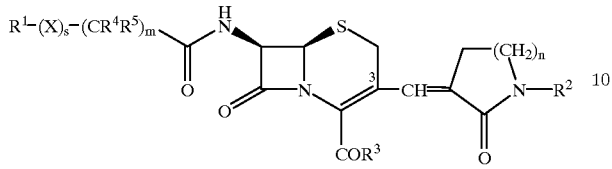

I wherein
- $R^1$ is halogen, phenyl, benzyl, naphthyl or heterocyclyl, the phenyl, benzyl, naphthyl and heterocyclyl being optionally substituted by at least one of halogen, hydroxy, optionally substituted lower alkyl or lower alkoxy, or amino, lower alkylamino, di-lower alkylamino, carboxy, or carbamoyl;
- $R^4$, $R^5$ independently are hydrogen, lower alkyl or phenyl;
- X is S, O, NH or $CH_2$;
- n is 0, 1 or 2;
- m is 0 or 1;
- S is 0 or 1;
- $R^2$ is hydrogen, hydroxy, lower alkyl-$Q_r$, cycloalkyl-$Q_r$, lower alkoxy, lower alkenyl, cycloalkenyl-$Q_r$, lower alkynyl, aralkyl-$Q_r$, aryl-$Q_r$, aryloxy, aralkoxy, a heterocyclic ring or a heterocyclyl-$Q_r$, the lower alkyl, cycloalkyl, lower alkoxy, lower alkenyl, cycloalkenyl, lower alkynyl, aralkyl, aryl, aryloxy, aralkoxy or

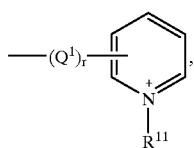

the heterocyclic ring optionally being substituted with at least one group selected from carboxy, amino, nitro, cyano, optionally fluoro substituted lower alkyl, lower alkoxy, hydroxy, halogen, $-CONR^6R^7$, $-N(R^7)$ $COOR^8$, $R^7CO-$, $R^7OCO-$, $R^7COO-$, $-C(R^7R^9)$ $CO_2R^8$, $-C(R^7R^9)CONR^7R^{10}$,
wherein
- $R^6$ is hydrogen, lower alkyl, or cycloalkyl;
- $R^7$ and $R^9$ are independently hydrogen or lower alkyl;
- $R^8$ is hydrogen, lower alkyl or a lower alkenyl; and
- $R^{10}$ is hydrogen, ω-hydroxy-alkyl, phenyl, naphthyl or heterocyclyl, the phenyl, naphthyl or heterocyclyl being unsubstituted or substituted with hydroxy, halogen, optionally substituted lower alkyl or ω-hydroxyalkyl, optionally substituted lower alkoxy and/or cyano, or $R^7$ and $R^{10}$ form together group of formula

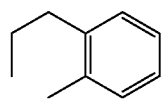

$R^{11}$ is hydrogen, lower alkyl, ω-hydroxy alkyl, benzyl or alkyl-heterocyclyl, the benzyl and the heterocyclyl group being unsubstituted or substituted with at least one of the groups cyano, carboxy or hydroxy; or is $-CH_2CONR^7R^{10}$;
- Q is $-CHR-$, $-CO-$ or $-SO_2-$;
- r is 0 or 1;
- R is hydrogen or lower alkyl; and
- $R^3$ is hydroxy, $-O^-$, lower-alkoxy, or $-OM$ and M is an alkali metal;
    wherein each heterocyclyl is independently an unsaturated or saturated, unsubstituted or substituted 4-, 5-, 6-, or 7-membered heterocyclic ring containing at least one atom selected from the group consisting of oxygen, nitrogen and sulfur;
    an ester thereof which is readily hydrolyzable in vivo, a pharmaceutically acceptable salt thereof, or a hydrate thereof, or a hydrate of said ester or said salt wherein when $R^2$ is a group of formula

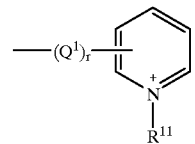

$R^3$ is $-O^-$; and when $R^3$ is $-O^-$, $R^2$ is a group of formula

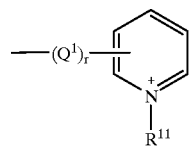

$Q^1$ is $CH_2$.

3. A compound selected from the group consisting of:
- (E)-(6R,7R)-3-[1-[1-[(4-Hydroxy-phenylcarbamoyl)-methyl]-pyridin-1-ium-4-ylmethyl]-2-oxo-pyrrolidin-3-ylidenemethyl3–8-oxo-7-[2-(2,4,5-trichloro-phenylsulfanyl)-acetylamino]-5-thia-1-aza-bicyclo[4.2.0]oct-2-ene-2-carboxylate;
- (E)-(6R,7R)-3-[1-[-[(4-Hydroxy-phenylcarbamoyl)-methyl]-pyridin-1-ium-4-ylmethyl]-2-oxo-pyrrolidin-3-ylidenemethyl]-8-oxo-7-[2-(1-benzothiazol-2-ylsulfanyl)-acetylamino]-5-thia-1-aza-bicyclo[4.2.0]oct-2-ene-2-carboxylate;
- (E)-(6R,7R)-3-[1-[1-[(4-Hydroxy-phenylcarbamoyl)-methyl]-pyridin-1-ium-4-ylmethyl]-2-oxo-pyrrolidin-3-ylidenemethyl]-8-oxo-7-[2-(pyridin-4-ylsulfanyl)-acetylamino]-5-thia-1-aza-bicyclo[4.2.0]oct-2-ene-2-carboxylate;
- (E)-(6R,7R)-3-[1-[1-[(3-Fluoro-4-hydroxy-phenylcarbamoyl)-methyl]-pyridin-1-ium-4-ylmethyl]-2-oxo-pyrrolidin-3-ylidenemethyl]-8-oxo-7-(2,4,5-trichloro-phenylsulfanyl)-acetylamino)-5-thia-1-aza-bicyclo[4.2.0]oct-2-ene-2-carboxylate;
- (E)-(6R,7R)-3-[1-[1-[(4-Hydroxy-phenylcarbamoyl)-methyl]-pyridin-1-ium-4-ylmethyl]-2-oxo-pyrrolidin-3-ylidenemethyl]-8-oxo-7-(2-phenylsulfanyl-acetylamino)-5-thia-1-aza-bicyclo[4.2.0]oct-2-ene-2-carboxylate;
- (E)-(6R,7R)-3-[1-[1-[(3-Fluoro-4-hydroxy-phenylcarbamoyl)-methyl]-pyridin-1-ium-4-ylmethyl]-2-oxo-pyrrolidin-3-ylidenemethyl]-7-[2-

(naphthalen-2-ylsulfanyl)-acetylamino]-8-oxo-5-thia-1-aza-bicyclo[4.2.0]oct-2-ene-2-carboxylate;
(E)-(6R,7R)-7-[2-(3,4-Dichloro-phenylsulfanyl)-acetylamino]-3-[1-[1-[(3-fluoro-4) hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate;
(E)-(6R,7R)-3-[1-[1-[(3-Fluoro-4-hydroxy-phenylcarbamoyl)-methyl]-pyridin-1-ium-4-ylmethyl]-2-oxo-pyrrolidin-3-ylidenemethyl]-8-oxo-7-(2-phenylsulfanyl-acetylamino)-5-thia-1-aza-bicyclo[4.2.0]oct-2-ene-2-carboxylate;
(E)-(6R,7R)-3-(1-Cyclopropylmethyl-2-oxo-pyrrolidin-3-ylidenemethyl)-8-oxo-7-[2-(2,4,5-trichloro-phenylsulfanyl)-acetylamino]-5-thia-1-aza-bicyclo[4.2.0]oct-2-ene-2-carboxylic acid;
(E)-(6R,7R)-7-[2-(Benzothiazol-2-ylsulfanyl)-acetylaminol-3-( 1-cyclopropylmethyl-2-oxo-pyrrolidin-3-ylidenemethyl)-8-oxo-5-thia-1-aza-bicyclo[4.2.0]oct-2-ene-2-carboxylic acid;
(E)-(6R,7R)-3-[1-(3-Hydroxy-benzyl)-2-oxo-pyrrolidin-3-ylidenemethyl]-8-oxo-7-[2-(2,4,5-trichloro-phenylsulfanyl)-acetylamino]-5-thia-1-aza-bicyclo[4.2.0]oct-2-ene-2-carboxylic acid;
(E)-(6R,7S)-3-[1-(3-Hydroxy-benzyl)-2-oxo-pyrrolidin-3-ylidenemethyl]-8-oxo-7-[2-naphthalen-2-ylsulfanyl)-acetylamino]-5-thia-1-aza-bicyclo[4.2.0]oct-2-ene-2-carboxylic acid;
a mixture of (E)-(6R,7R)-8-oxo-3-[(R)- and -[(S)2-oxo-[1,3']Bipyrrolidinyl-3-ylidenemethyl]-8-oxo-7-[2-(2,4,5-trichloro-phenylsulfanyl)-acetylamino]-5-thia-1-aza-bicyclo[4.2.0]oct-2-ene-2-carboxylic acid hydrochloride (1:1);
(E)-(6R,7R)-8-Oxo-3-[(R)-2-oxo-[1,3']bipyrrolidinyl-3-ylidenemethyl]-7-(2-phenylsulfanyl-acetylamino)-5-thia-1-aza-bicyclo[4.2.0]oct-2-ene-2-carboxylic acid hydrochloride (1:1);
(E)-(6R,7R)-7-[2-(2,5-Dichloro-phenylsulfanyl)-acetylamino]-3-[1-[(3-fluoro-4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate; and
(E)-(6R,7R)-3-(1-Cyclopropyl-2-oxo-pyrrolidin-3-ylidenemethyl)-7-[2-(naphthalen-1-ylsulfanyl)-acetylamino]-8-oxo-5-thia-1-aza-bicyclo[4.2.0]oct-2-ene-2-carboxylic acid imidazole salt (1:1).

4. The compound of claim 3, (E)-(6R,7R7-[2-(2,5-Dichloro-phenylsulfanyl)-acetylamino]-3-[1-[(3-fluoro-4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0)oct-2-ene-2-carboxylate.

5. The compound of claim 3, (E)-(6R,7R)-3-(1-Cyclopropyl-2-oxo-pyrrolidin-3-ylidenemethyl)-7-[2-(naphthalen-1-ylsulfanyl)-acetylamino]-8-oxo-5-thia-1-aza-bicyclo[4.2.0]oct-2-ene-2-carboxylic acid imidazole salt (1:1).

6. The compound of claim 1, wherein n is 1.

7. The compound of claim 2 wherein $R^1$ is selected from the groups phenyl, 2,4,5-trichlorophenyl, 3,4-dichlorophenyl, 2,5-dichlorophenyl, 4-trifluoromethylphenyl, 4-methoxyphenyl, 4-hydroxymethylphenyl, 3,4-dimethoxyphenyl, 4-methyl-1,2,4-triazol-5-yl, 1-methyl-tetrazol-5-yl, pyrimidin-2-yl, optionally substituted pyridinium-1-yl, 2-yl, -3-yl or -4-yl, benzimidazol-2-yl, 2-benzthiazolyl, 4-pyridinyl, (2-amino)-thiazol-4-yl, 2-naphthyl, benzyl.

8. The compound of claim 2 wherein $R^2$ is methylcyclopropyl, 2-, 3- or 4-hydroxybenzyl, pyrrolidin-3-yl or a group of formula

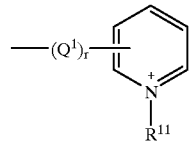

wherein
Q$^1$ is —CH$_2$—
r is 0 or 1; and
$R^{11}$ is hydrogen, lower alkyl, ω-hydroxy alkyl, benzyl or alkyl-heterocyclyl, the benzyl and the heterocyclyl group being unsubstituted or substituted with at least one of the groups cyano, carboxy or hydroxy; or is —CH$_2$CONR$^7$R$^{10}$;
wherein the heterocyclyl is an unsaturated or saturated, unsubstituted or substituted 4-, 5-, 6-, or 7-membered heterocyclic ring containing at least one atom selected from the group consisting of oxygen, nitrogen and sulfur.

9. The compound of claim 3, (E)-(6R,7R)-7-[2-(Benzothiazol-2-ylsulfanyl)-acetylamino]-3-(1-cyclopropylmethyl-2-oxo-pyrrolidin-3-ylidenemethyl)-8-oxo-5-thia-1-aza-bicyclo[4.2.0]oct-2-ene-2-carboxylic acid.

10. The compound of claim 3, (E)-(6R,7R)-3-[1-(3-Hydroxy-benzyl)-2-oxo-pyrrolidin-3-ylidenemethyl]-8-oxo-7-(2-(2,4,5-trichloro-phenylsulfanyl)-acetylamino]-5-thia-1-aza-bicyclo[4.2.0]oct-2-ene-2-carboxylic acid.

11. The compound of claim 3, (E)-(6R,7S)-3-[1-(3-Hydroxy-benzyl)-2-oxo-pyrrolidin-3-ylidenemethyl]-8-oxo-7-[2-naphthalen-2-ylsulfanyl)-acetylamino]-5-thia-1-aza-bicyclo[4.2.0]oct-2-ene-2-carboxylic acid.

12. The compound of claim 3, being a mixture of (E)-(6R,7R)-8-oxo-3-[(R)- and -[(S)-2-oxo-[1,3']Bipyrrolidinyl-3-ylidenemethyl]-8-oxo-7-[2-(2,4,5-trichloro-phenylsulfanyl)-acetylamino]-5-thia-1-aza-bicyclo[4.2.0]oct-2-ene-2-carboxylic acid hydrochloride (1:1).

13. The compound of claim 3, (E)-(6R,7R)-8-Oxo-3-[(R)-2-oxo-[1,3']bipyrrolidinyl-3-ylidenemethyl]-7-(2-phenylsulfanyl-acetylamino)-5-thia-1-aza-bicyclo[4.2.0]oct-2-ene-2-carboxylic acid hydrochloride (1:1).

14. A compound of the formula

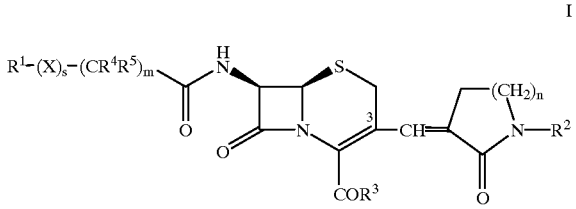

wherein
$R^1$ is phenyl, 2,4,5-trichlorophenyl, 3,4-dichlorophenyl, 2,5-dichlorophenyl, 4-trifluoromethylphenyl, 4-methoxyphenyl, 4-hydroxymethylphenyl, 3,4-dimethoxyphenyl, 4-methyl- 1,2,4-triazol-5-yl, 1-methyl-tetrazol-5-yl, pyrimidin-2-yl, pyridinium-1-yl, benzimidazol-2-yl, 2-benzthiazolyl, 4-pyridinyl, (2-amino)-thiazol-4-yl, 2-naphthyl, or benzyl;
wherein when $R^1$ is pyridinium-1-yl, $R^3$ is —O$^-$;
$R^4$, $R^5$ independently are hydrogen, lower alkyl or phenyl;
X is S, O, NH or CH$_2$;

n is 0, 1 or 2;
m is 0 or 1;
s is 0 or 1;
$R^2$ is hydrogen, hydroxy, —$CH_2$—$CONHR^6$, lower alkyl-$Q_r$, cycloalkyl-$Q_r$, lower alkoxy, lower alkenyl, cycloalkenyl-$Q_r$, lower alkynyl, aralkyl-$Q_r$, aryl-$Q_r$, aryloxy, aralkoxy, a heterocyclic ring or a heterocyclyl-$Q_r$, the lower alkyl, cycloalkyl, lower alkoxy, lower alkenyl, cycloalkenyl, lower alkynyl, aralkyl, aryl, aryloxy, aralkoxy and the heterocyclic ring is optionally substituted with at least one group selected from carboxy, amino, nitro, cyano, —$SO_2NHR^6$, optionally fluoro substituted lower alkyl, lower alkoxy, hydroxy, halogen, —$CONR^6R^7$, —$CH_2CONR^6R^7$, —$N(R^7)COOR^8$, $R^7CO$—, $R^7OCO$—, $R^7COO$—, —$C(R^7R^9)CO_2R^8$, —$C(R^7R^9)CONR^7R^{10}$, wherein
$R^6$ is hydrogen, lower alkyl, cycloalkyl or aryl;
$R^7$ and $R^9$ are independently hydrogen or lower alkyl;
$R^8$ is hydrogen, lower alkyl or a lower alkenyl group; and
$R^{10}$ is hydrogen, ω-hydroxy-alkyl, phenyl, naphthyl or heterocyclyl, the phenyl, naphthyl or heterocyclyl being unsubstituted or substituted with hydroxy, halogen, optionally substituted lower alkyl or ω-hydroxyalkyl, optionally substituted lower alkoxy and/or cyano, or $R^7$ and $R^{10}$ form together group of formula

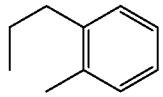

Q is —CHR—, —CO— or —$SO_2$—;
r is 0 or 1;
R is hydrogen or lower alkyl; and
$R^3$ is hydroxy, —$O^-$, lower-alkoxy, or —OM and M is an alkali metal; an ester thereof which is readily hydrolyzable in vivo, a pharmaceutically acceptable salt thereof, or a hydrate thereof, or a hydrate of said ester or said salt
wherein when $R^3$ is —$O^-$, $R^1$ is pyridinium-1-yl and when $R^1$ is pyridinium-1-yl, $R^3$ is —$O^-$;
wherein each heterocyclyl is independently an unsaturated or saturated, unsubstituted or substituted 4-, 5-, 6-, or 7-membered heterocyclic ring containing at least one atom selected from the group consisting of oxygen, nitrogen and sulfur.
15. A compound of the formula

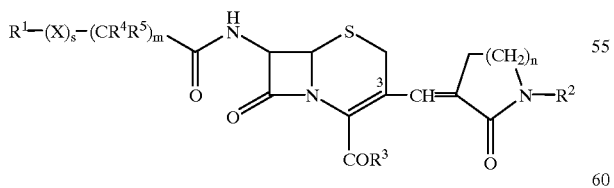

I wherein
$R^1$ is halogen, lower alkyl, phenyl, benzyl, styryl, naphthyl or heterocyclyl; the lower alkyl, phenyl, benzyl, styryl, naphthyl and heterocyclyl being optionally substituted by at least one of halogen, hydroxy, optionally substituted lower alkyl, optionally substituted lower alkoxy, optionally substituted phenyl, amino, lower alkylamino, di-lower alkylamino, carboxy, carbamoyl or lower alkylcarbamoyl;

$R^4$, $R^5$ independently are hydrogen, lower alkyl or phenyl;
X is S, O, NH or $CH_2$;
n is 0, 1 or 2;
m is 0 or 1;
s is 0 or 1;
$R^2$ is methylcyclopropyl, 2-, 3- or 4-hydroxybenzyl, pyrrolidin-3-yl or a group of formula

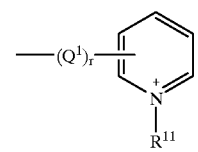

wherein
Q1 is —CH2—
r is 0 or 1;
wherein when $R^2$ is a group of formula

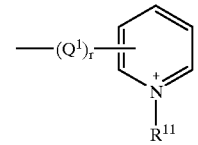

$R^3$ is —$O^-$; and
$R^{11}$ is hydrogen, lower alkyl, ω-hydroxy alkyl, benzyl or alkyl-heterocyclyl, the benzyl group being unsubstituted or substituted with at least one of the groups cyano, carboxy or hydroxy, and the heterocyclyl group being optionally further substituted with at least one of the groups cyano, carboxy or hydroxy; or is —$CH_2CONR^7R^{10}$;
wherein
$R^7$ is hydrogen or lower alkyl; and
$R^{10}$ is hydrogen, ω-hydroxy-alkyl, phenyl, naphthyl or heterocyclyl, the phenyl, naphthyl or heterocyclyl being unsubstituted or substituted with hydroxy, halogen, optionally substituted lower alkyl or ω-hydroxyalkyl, optionally substituted lower alkoxy and/or cyano, or $R^7$ and $R^{10}$ form together group of formula

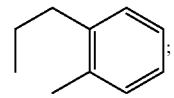;

and
$R^3$ is hydroxy, —$O^-$, lower-alkoxy, or —OM and M is an alkali metal;

an ester thereof which is readily hydrolyzable in vivo, a pharmaceutically acceptable salt thereof, or a hydrate thereof, or a hydrate of said ester or said salt wherein when R³ is —O⁻, R² is a group of formula.

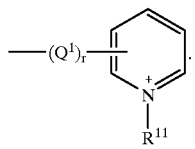

16. A. The compound of claim 1, wherein n is 1.

17. The compound of claim 3, (E)-(6R,7R)-3-[1-[1-[(4-Hydroxy-phenylcarbamoyl)-methyl]-pyridin-1-ium-4-ylmethyl]-2-oxo-pyrrolidin-3-ylidenemethyl]-8-oxo-7-[2-(2,4,5-trichloro-phenylsulfanyl)-acetylamino]-5-thia-1-aza-bicyclo[4.2.0]oct-2-ene-2-carboxylate.

18. The compound of claim 3, (E)-(6R,7R)-3-[1-[1-[(4-Hydroxy-phenylcarbamoyl)-methyl]-pyridin-1-ium-4-ylmethyl]-2-oxo-pyrrolidin-3-ylidenemethyl]-8-oxo-7-[2-(1-benzothiazol-2-ylsulfanyl)-acetylamino]-5-thia-1-aza-bicyclo[4.2.0]oct-2-ene-2-carboxylate.

19. The compound of claim 3, (E)-(6R,7R)-3-[1-[1-[(4-Hydroxy-phenylcarbamoyl)-methyl]-pyridin-1-ium-4-ylmethyl-2-oxo-pyrrolidin-3-ylidenemethyl]-8-oxo-7-[2-(pyridin-4-ylsulfanyl)-acetylamino]-5-thia-1-aza-bicyclo[4.2.0]oct-2-ene-2-carboxylate.

20. The compound of claim 3, (E)-(6R,7R)-3-[1-[1-[(3-Fluoro-4-hydroxy-phenylcarbamoyl)-methyl]-pyridin-1-ium-4-ylmethyl]-2-oxo-pyrrolidin-3-ylidenemethyl]-8-oxo-7-(2,4,5-trichloro-phenylsulfanyl)-acetylamino)-5-thia-1-aza-bicyclo[4.2.0]oct-2-ene-2-carboxylate.

21. The compound of claim 3, (E)-(6R,7R)-3-[1-[1-[(4-Hydroxy-phenylcarbamoyl)-methyl]-pyridin-1-ium-4-ylmethyl]-2-oxo-pyrrolidin-3-ylidenemethyl]-8-oxo-7-(2-phenylsulfanyl-acetylamino)-5-thia-1-aza-bicyclo[4.2.0]oct-2-ene-2-carboxylate.

22. The compound of claim 3, (E)-(6R,7R)-3-[1-[1-[(3-Fluoro-4-hydroxy-phenylcarbamoyl)-methyl]-pyridin-1-ium-4-ylmethyl]-2-oxo-pyrrolidin-3-ylidenemethyl]-7-[2-(naphthalen-2-ylsulfanyl)-acetylamino]-8-oxo-5-thia-1-aza-bicyclo[4.2.0]oct-2-ene-2-carboxylate.

23. The compound of claim 3, (E)-(6R,7R)-7-[2-(3,4-Dichloro-phenylsulfanyl)-acetylamino]-3-[1-[1-[(3-fluoro-4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate.

24. The compound of claim 3, (E)-(6R,7R)-3-[1-[1-[(3-Fluoro-4-hydroxy-phenylcarbamoyl)-methyl]-pyridin-1-ium-4-ylmethyl]-2-oxo-pyrrolidin-3-ylidenemethyl]-8-oxo-7-(2-phenylsulfanyl-acetylamino)-5-thia-1-aza-bicyclo[4.2.0]oct-2-ene-2-carboxylate.

25. The compound of claim 3, (E)-(6R,7R)-3-(1-Cyclopropylmethyl-2-oxo-pyrrolidin-3-ylidenemethyl)-8-oxo-7-[2-(2,4,5-trichloro-phenylsulfanyl)-acetylamino]-5-thia-1-aza-bicyclo[4.2.0]oct-2-ene-2-carboxylic acid.

* * * * *

UNITED STATES PATENT AND TRADEMARK OFFICE
CERTIFICATE OF CORRECTION

PATENT NO. : 6,294,668 B1
DATED : September 25, 2001
INVENTOR(S) : Angehrn et al.

It is certified that error appears in the above-identified patent and that said Letters Patent is hereby corrected as shown below:

Column 64, claim 3,
Line 44, "(E)-(6R,7R)-3-[1-[-[(4-Hydroxy" should read -- (E)-(6R,7R)-3-[1-[1-[(4-Hydroxy --.

Column 65, claim 3,
Lines 4-5, "[(3-fluoro-4) hydroxy-phenylcarbamoyl)" should read -- [(3-fluoro-4-hydroxy-phenylcarbamoyl) --.

Column 65, claim 4,
Line 48, "(E)-(6R,7R7-[2-(2,5-" should read -- (E)-(6R,7R)-7-[2-(2,5 --.

Signed and Sealed this

Twenty-sixth Day of March, 2002

Attest:

*Attesting Officer*

JAMES E. ROGAN
*Director of the United States Patent and Trademark Office*